(12) United States Patent
Merhi et al.

(10) Patent No.: US 11,071,844 B2
(45) Date of Patent: Jul. 27, 2021

(54) EMBOLIC PROTECTION DEVICE

(71) Applicant: Innovative Cardiovasular Solutions, LLC, Kalamazoo, MI (US)

(72) Inventors: William M. Merhi, Grand Rapids, MI (US); Andy Black, North Barrington, IL (US); Mark Carlson, North Barrington, IL (US); Josh Greene, North Barrington, IL (US); Kelly Jensen, North Barrington, IL (US); Andy Leopold, North Barrington, IL (US); Ben Rockwell, North Barrington, IL (US)

(73) Assignee: Innovative Cardiovascular Solutions, LLC, Kalamazoo, MI (US)

( * ) Notice: Subject to any disclaimer, the term of this patent is extended or adjusted under 35 U.S.C. 154(b) by 0 days.

(21) Appl. No.: 16/930,110

(22) Filed: Jul. 15, 2020

(65) Prior Publication Data

US 2020/0353208 A1 Nov. 12, 2020

Related U.S. Application Data

(63) Continuation of application No. PCT/US2019/020952, filed on Mar. 6, 2019.

(Continued)

(51) Int. Cl.
*A61F 2/01* (2006.01)
*A61M 25/00* (2006.01)
(Continued)

(52) U.S. Cl.
CPC ... *A61M 25/0041* (2013.01); *A61B 17/00234* (2013.01); *A61B 90/39* (2016.02);
(Continued)

(58) Field of Classification Search
CPC ........ A61F 2/0103; A61F 2/013; A61F 2/014; A61F 2002/015; A61F 2002/016;
(Continued)

(56) References Cited

U.S. PATENT DOCUMENTS 3,938,501 A 2/1976 Erikson
4,279,252 A 7/1981 Martin
(Continued)

FOREIGN PATENT DOCUMENTS

EP 0129634 A1 1/1985
EP 0154403 A1 9/1985
(Continued)

OTHER PUBLICATIONS

PCT International Search Report dated May 21, 2019 for PCT/US2019/020952.
(Continued)

*Primary Examiner* — Dianne Dornbusch
(74) *Attorney, Agent, or Firm* — Honigman LLP; Andrew N. Weber; Jonathan P. O'Brien

(57) ABSTRACT

The present invention includes an embolic protection device comprising a catheter having a self-expanding embolic filter that is disposed around the catheter proximal to a distal portion, wherein the embolic filter comprises a frame, and the frame defines an opening of the embolic filter that faces the distal end of the catheter; a deployment mechanism that is disposed around at least a portion of the catheter, wherein the deployment mechanism is longitudinally movable with respect to the catheter, the deployment mechanism is configured to contain the embolic filter in a collapsed configuration, and the embolic filter is configured to self-expand upon the longitudinal retraction of the deployment mechanism; and a wire coupled to the frame for expanding the size or diameter of the embolic filter opening.

27 Claims, 47 Drawing Sheets

Related U.S. Application Data

(60) Provisional application No. 62/639,618, filed on Mar. 7, 2018, provisional application No. 62/812,391, filed on Mar. 1, 2019.

(51) Int. Cl.
   *A61B 90/00* (2016.01)
   *A61B 17/00* (2006.01)
   *A61B 17/221* (2006.01)

(52) U.S. Cl.
   CPC ... *A61B 17/221* (2013.01); *A61B 2017/00867* (2013.01); *A61B 2017/2215* (2013.01); *A61B 2017/2217* (2013.01); *A61B 2090/3966* (2016.02); *A61F 2/013* (2013.01); *A61F 2210/0014* (2013.01)

(58) Field of Classification Search
   CPC .......... A61B 17/221; A61B 2017/2212; A61B 2017/2215; A61B 2017/2217; A61B 2017/00243; A61B 2210/0014; A61M 2205/0266; A61M 2205/0041
   See application file for complete search history.

(56) References Cited

U.S. PATENT DOCUMENTS

| | | |
|---|---|---|
| 4,406,656 A | 9/1983 | Hattler et al. |
| 4,425,908 A | 1/1984 | Simon |
| 4,531,933 A | 7/1985 | Norton et al. |
| 4,601,713 A | 7/1986 | Fuqua |
| 4,671,795 A | 6/1987 | Mulchin |
| 4,694,838 A | 9/1987 | Wijayarthna et al. |
| 4,710,181 A | 12/1987 | Fuqua |
| 4,735,620 A | 4/1988 | Ruiz |
| 4,738,666 A | 4/1988 | Fuqua |
| 4,878,495 A | 11/1989 | Grayzel |
| 4,958,634 A | 9/1990 | Jang |
| 4,961,731 A | 10/1990 | Bodicky et al. |
| 4,986,814 A | 1/1991 | Burney et al. |
| 5,106,368 A | 4/1992 | Uldall et al. |
| 5,163,431 A | 11/1992 | Griep |
| 5,180,364 A | 1/1993 | Ginsburg |
| 5,192,286 A | 3/1993 | Phan et al. |
| 5,201,723 A | 4/1993 | Quinn |
| 5,221,253 A | 6/1993 | Coll |
| 5,320,605 A | 6/1994 | Sahota |
| 5,421,832 A | 6/1995 | Lefebvre |
| 5,472,418 A | 12/1995 | Palestrant |
| 5,474,537 A | 12/1995 | Solar |
| 5,573,508 A | 11/1996 | Thornton |
| 5,658,296 A | 8/1997 | Bates et al. |
| 5,735,831 A | 4/1998 | Johnson et al. |
| 5,738,667 A | 4/1998 | Solar |
| 5,779,716 A | 7/1998 | Cano et al. |
| 5,795,322 A | 8/1998 | Boudewijn |
| 5,807,318 A | 9/1998 | St. Goar et al. |
| 5,810,874 A | 9/1998 | Lefebvre |
| 5,814,064 A | 9/1998 | Daniel et al. |
| 5,827,324 A | 10/1998 | Cassell et al. |
| 5,910,154 A | 6/1999 | Tsugita et al. |
| 5,947,995 A | 9/1999 | Samuels |
| 5,954,745 A | 9/1999 | Gertler et al. |
| 6,001,118 A | 12/1999 | Daniel et al. |
| 6,053,932 A | 4/2000 | Daniel et al. |
| 6,059,814 A | 5/2000 | Ladd |
| 6,129,739 A | 10/2000 | Khosravi |
| 6,142,987 A | 11/2000 | Tsugita |
| 6,152,946 A * | 11/2000 | Broome ................. A61F 2/013 606/200 |
| 6,168,579 B1 | 1/2001 | Tsugita |
| 6,168,604 B1 | 1/2001 | Cano |
| 6,179,859 B1 | 1/2001 | Bates et al. |
| 6,179,861 B1 | 1/2001 | Khosravi et al. |
| 6,183,492 B1 | 2/2001 | Hart et al. |
| 6,190,357 B1 | 2/2001 | Ferrari et al. |
| 6,203,561 B1 | 3/2001 | Ramee et al. |
| 6,214,026 B1 | 4/2001 | Lepak et al. |
| 6,245,087 B1 | 6/2001 | Addis |
| 6,245,089 B1 | 6/2001 | Daniel et al. |
| 6,264,663 B1 | 7/2001 | Cano |
| 6,277,138 B1 | 8/2001 | Levinson et al. |
| 6,277,139 B1 | 8/2001 | Levinson et al. |
| 6,290,710 B1 | 9/2001 | Cryer et al. |
| 6,336,934 B1 | 1/2002 | Gilson et al. |
| 6,346,116 B1 | 2/2002 | Brooks et al. |
| 6,361,545 B1 | 3/2002 | Macoviak et al. |
| 6,371,970 B1 | 4/2002 | Khosravi et al. |
| 6,371,971 B1 | 4/2002 | Tsugita et al. |
| 6,395,014 B1 | 5/2002 | Macoviak et al. |
| 6,398,756 B2 | 6/2002 | Peterson et al. |
| 6,425,909 B1 | 7/2002 | Dieck et al. |
| 6,527,746 B1 | 3/2003 | Oslund et al. |
| 6,530,939 B1 | 3/2003 | Hopkins et al. |
| 6,537,294 B1 | 3/2003 | Boyle et al. |
| 6,540,722 B1 | 4/2003 | Boyle et al. |
| 6,544,279 B1 | 4/2003 | Hopkins et al. |
| 6,589,263 B1 | 7/2003 | Hopkins et al. |
| 6,595,967 B2 | 7/2003 | Kramer |
| 6,605,074 B2 | 8/2003 | Zadno-Azizi et al. |
| 6,645,224 B2 | 11/2003 | Gilson et al. |
| 6,656,202 B2 | 12/2003 | Papp et al. |
| 6,660,021 B1 | 12/2003 | Palmer et al. |
| 6,692,512 B2 | 2/2004 | Jang |
| 6,740,061 B1 | 5/2004 | Oslund et al. |
| 6,887,256 B2 | 5/2005 | Gilson et al. |
| 6,936,059 B2 | 8/2005 | Belef |
| 6,939,361 B1 | 9/2005 | Kleshinski |
| 6,951,555 B1 | 10/2005 | Suresh et al. |
| 6,969,396 B2 * | 11/2005 | Krolik ................ A61F 2/01 606/200 |
| 6,989,027 B2 | 1/2006 | Allen et al. |
| 7,004,176 B2 | 2/2006 | Lau |
| 7,014,647 B2 | 3/2006 | Brady et al. |
| 7,232,453 B2 | 6/2007 | Shimon |
| 7,648,518 B2 | 1/2010 | Salahieh et al. |
| 8,114,114 B2 | 2/2012 | Belson |
| 8,308,754 B2 | 11/2012 | Belson |
| 8,414,482 B2 | 4/2013 | Belson |
| 8,430,904 B2 | 4/2013 | Belson |
| 8,679,149 B2 | 3/2014 | Belson |
| 8,728,114 B2 | 5/2014 | Belson |
| 8,948,848 B2 | 2/2015 | Merhi |
| 9,107,734 B2 | 8/2015 | Belson |
| 9,186,238 B2 * | 11/2015 | Eidenschink ............. A61F 2/01 |
| 9,492,265 B2 | 11/2016 | Russell et al. |
| 9,668,849 B2 | 6/2017 | Shimon |
| 9,770,318 B2 | 9/2017 | Belson |
| 9,827,085 B2 | 11/2017 | Russell et al. |
| 9,855,143 B2 * | 1/2018 | Ho ...................... A61F 2/2454 |
| 10,016,267 B2 | 7/2018 | Belson |
| 10,166,094 B2 | 1/2019 | Belson et al. |
| 10,485,647 B2 | 11/2019 | Gera et al. |
| 10,617,507 B2 | 4/2020 | Belson |
| 10,624,732 B2 | 4/2020 | Shimon |
| 10,736,728 B2 | 8/2020 | Belson |
| 2002/0026203 A1 | 2/2002 | Bates et al. |
| 2002/0095171 A1 * | 7/2002 | Belef ................... A61F 2/013 606/200 |
| 2002/0095174 A1 | 7/2002 | Tsugita et al. |
| 2002/0161394 A1 | 10/2002 | Macoviak et al. |
| 2003/0199819 A1 * | 10/2003 | Beck .................. A61F 2/013 604/96.01 |
| 2003/0233115 A1 | 12/2003 | Eversull et al. |
| 2004/0193207 A1 | 9/2004 | Boismier |
| 2004/0215167 A1 | 10/2004 | Belson |
| 2004/0220521 A1 | 11/2004 | Barbut |
| 2004/0249409 A1 | 12/2004 | Krolik et al. |
| 2005/0101987 A1 | 5/2005 | Salahieh |
| 2005/0131438 A1 | 6/2005 | Cohn |
| 2005/0131449 A1 | 6/2005 | Salahieh et al. |
| 2005/0288631 A1 | 12/2005 | Lewis et al. |
| 2006/0195138 A1 | 8/2006 | Goll et al. |
| 2007/0198051 A1 | 8/2007 | Clubb et al. |

(56) References Cited

U.S. PATENT DOCUMENTS

| | | |
|---|---|---|
| 2008/0045896 A1 | 2/2008 | Yribarren et al. |
| 2009/0062840 A1 | 3/2009 | Angel |
| 2010/0179583 A1 | 7/2010 | Carpenter et al. |
| 2010/0217304 A1 | 8/2010 | Angel et al. |
| 2010/0312268 A1 | 12/2010 | Belson |
| 2010/0324554 A1 | 12/2010 | Gifford et al. |
| 2010/0324589 A1 | 12/2010 | Carpenter et al. |
| 2012/0172915 A1* | 7/2012 | Fifer ............... A61B 17/22031 606/200 |
| 2012/0179033 A1* | 7/2012 | Merhi ................ A61F 2/013 600/435 |
| 2013/0245669 A1 | 9/2013 | Basu et al. |
| 2014/0005540 A1* | 1/2014 | Merhi ................ A61F 2/013 600/435 |
| 2014/0180329 A1 | 6/2014 | Krahbichler |
| 2015/0313701 A1* | 11/2015 | Krahbichler ......... A61F 2/013 606/300 |
| 2016/0100928 A1* | 4/2016 | Lees .................. A61F 2/013 606/200 |
| 2016/0235515 A1 | 8/2016 | Merhi |
| 2016/0324621 A1* | 11/2016 | Shezifi ............... A61F 2/01 |
| 2017/0216011 A1 | 8/2017 | Belson |
| 2019/0183627 A1 | 6/2019 | Russell et al. |
| 2019/0307544 A1 | 10/2019 | Belson |
| 2020/0054434 A1 | 2/2020 | Gera et al. |

FOREIGN PATENT DOCUMENTS

| | | |
|---|---|---|
| EP | 0453008 A1 | 10/1991 |
| EP | 1482861 | 12/2004 |
| EP | 2166958 A2 | 3/2010 |
| JP | 2004358273 | 12/2004 |
| WO | 2000/012169 A1 | 3/2000 |
| WO | 2001/08742 | 2/2001 |
| WO | 2003/032868 | 4/2003 |
| WO | 2003/090834 A2 | 11/2003 |
| WO | 2009/055782 | 4/2009 |
| WO | 2010/026240 A1 | 3/2010 |
| WO | 2012/094195 | 7/2012 |
| WO | 2015/061269 | 4/2015 |

OTHER PUBLICATIONS

Edwards Lifesciences LLC, Edwards Protection Cannulae, "EMBOL-X Glide Protection System," Brochure, 2010.

Nietlispach, et al., "An Embolic Deflection Device for Aortic Valve Interventions," J. Am. Coll. Cardio. Intv.; Cardiovasular Interventions; vol. 3, No. 11, 2010: pp. 1133-1140. Downloaded from http://interventions.onlinejacc.org on Nov. 18, 2011.

International Search Report and Written Opinion for Application No. PCT/US2011/67440 dated Apr. 27, 2012.

International Search Report and Written Opinion for Application No. PCT/US2014/061504 dated Jan. 8, 2015.

* cited by examiner

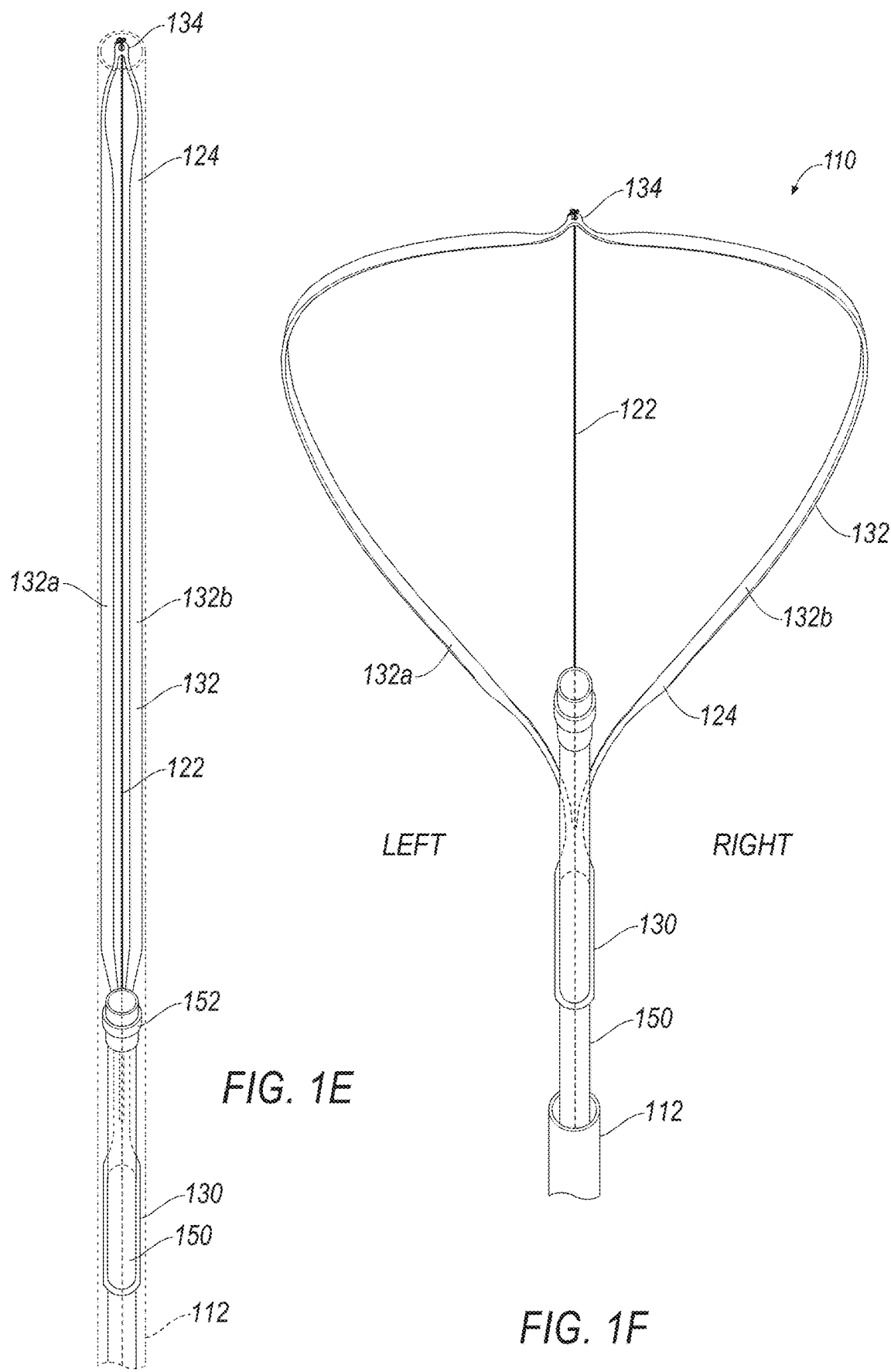

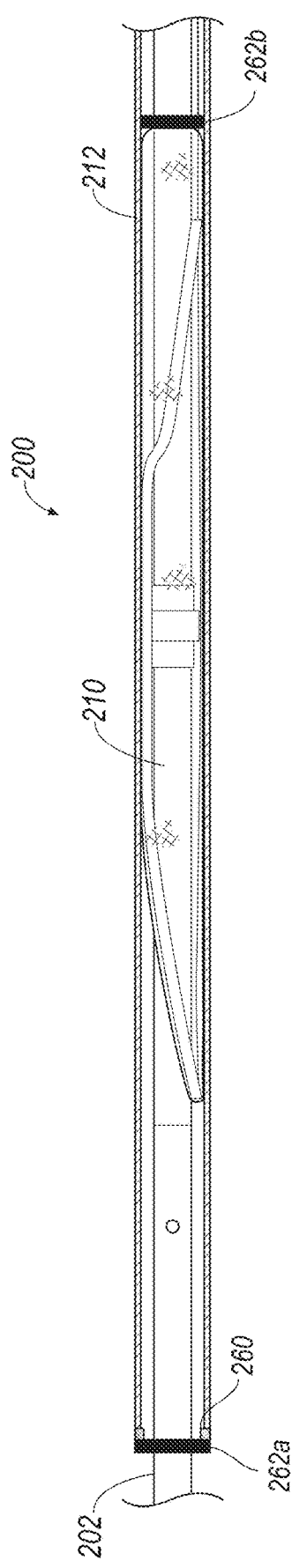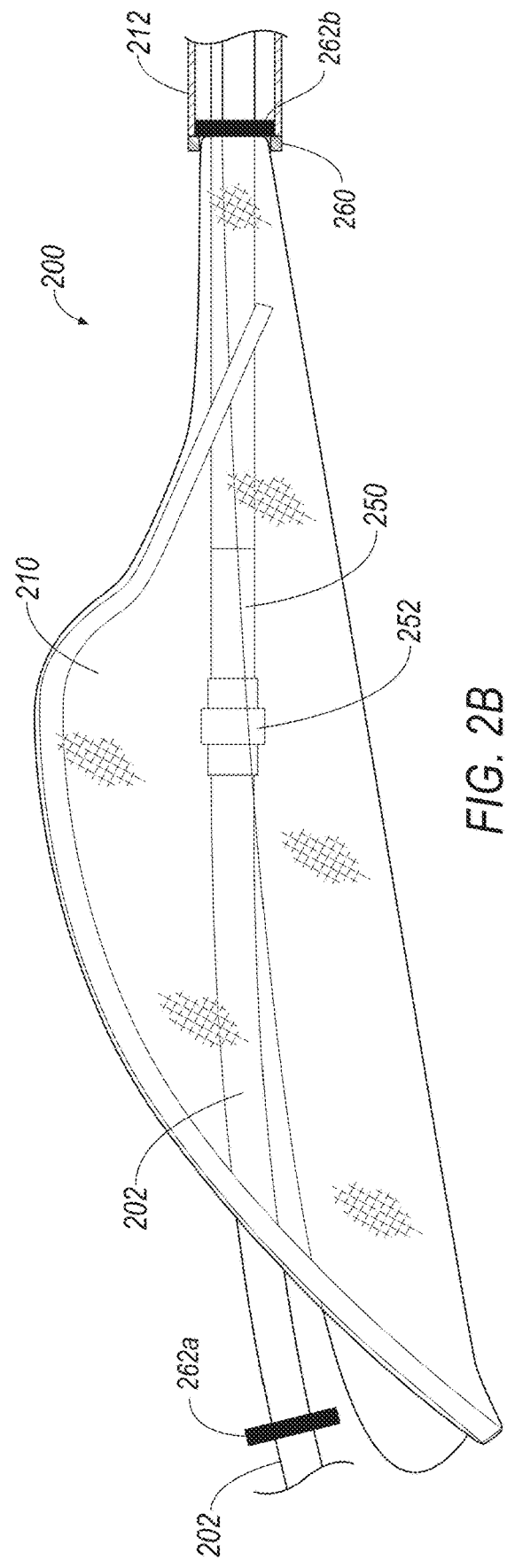

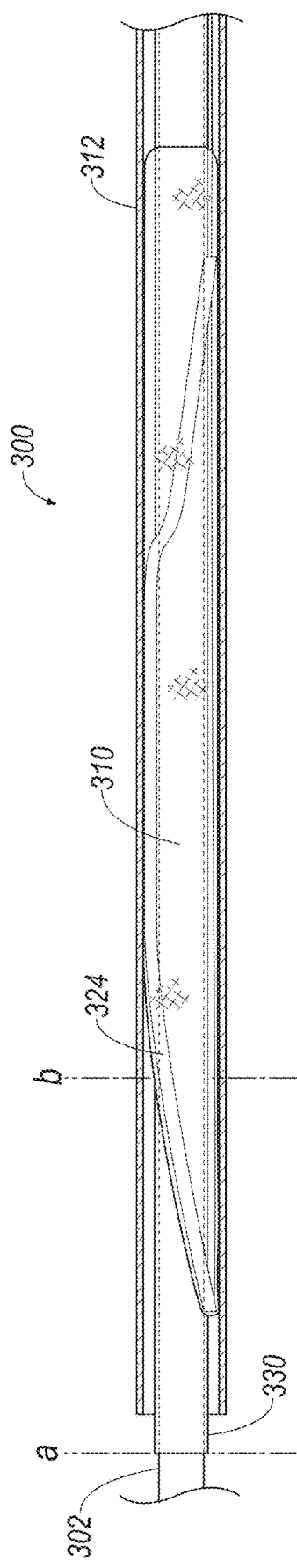
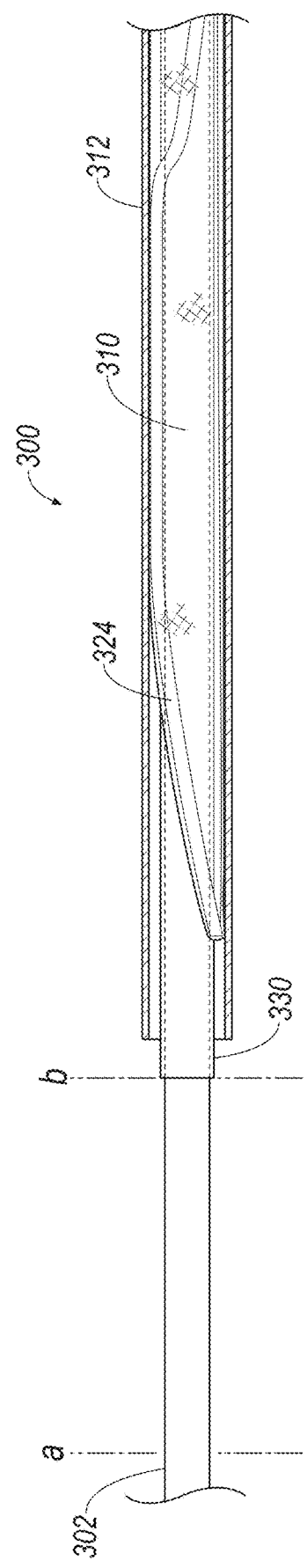
FIG. 3A
FIG. 3B

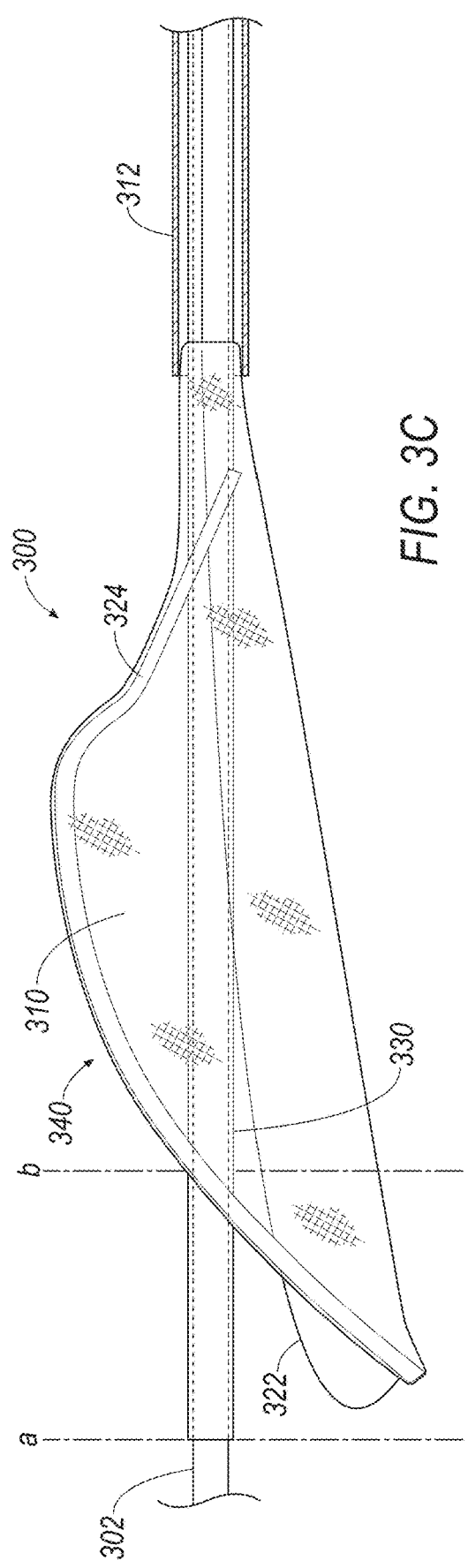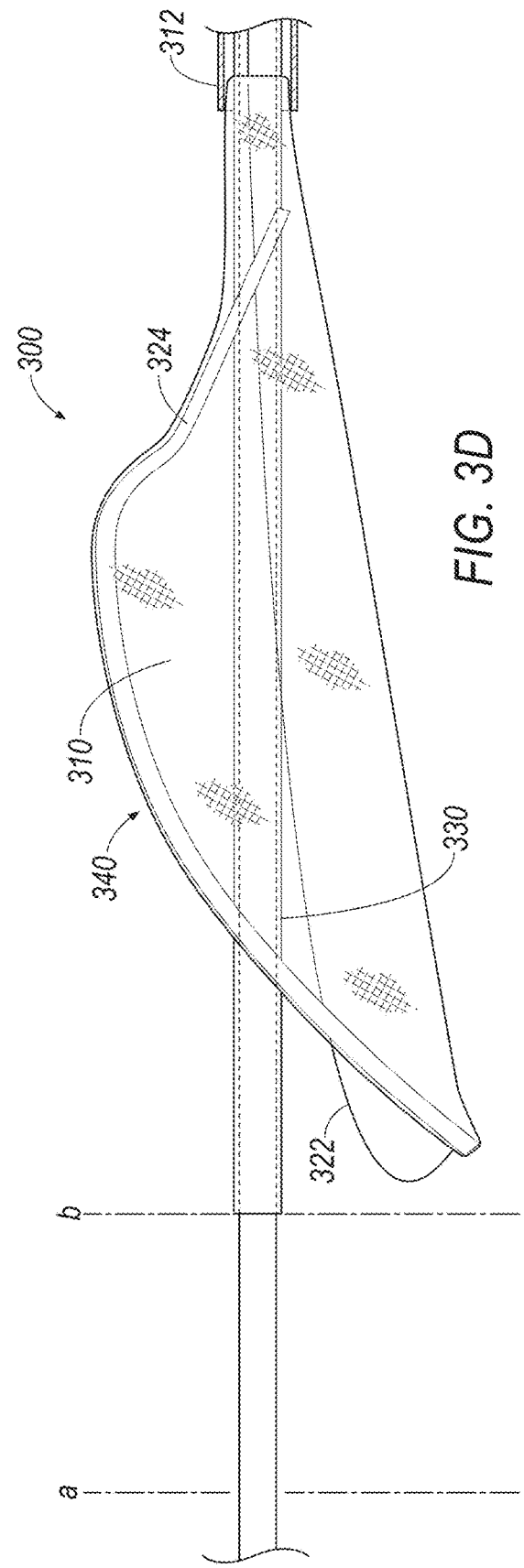

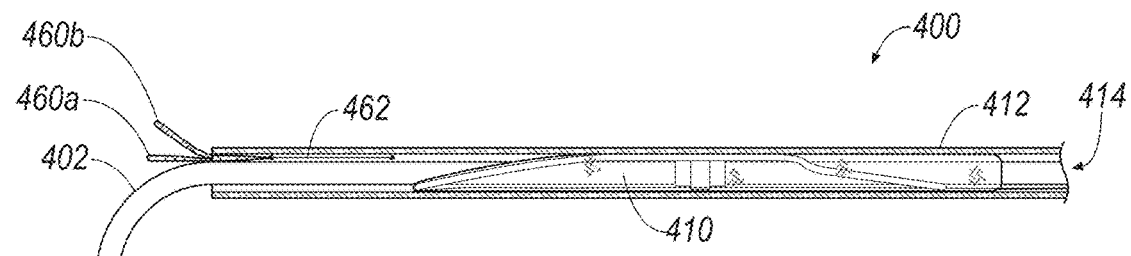
FIG. 4A
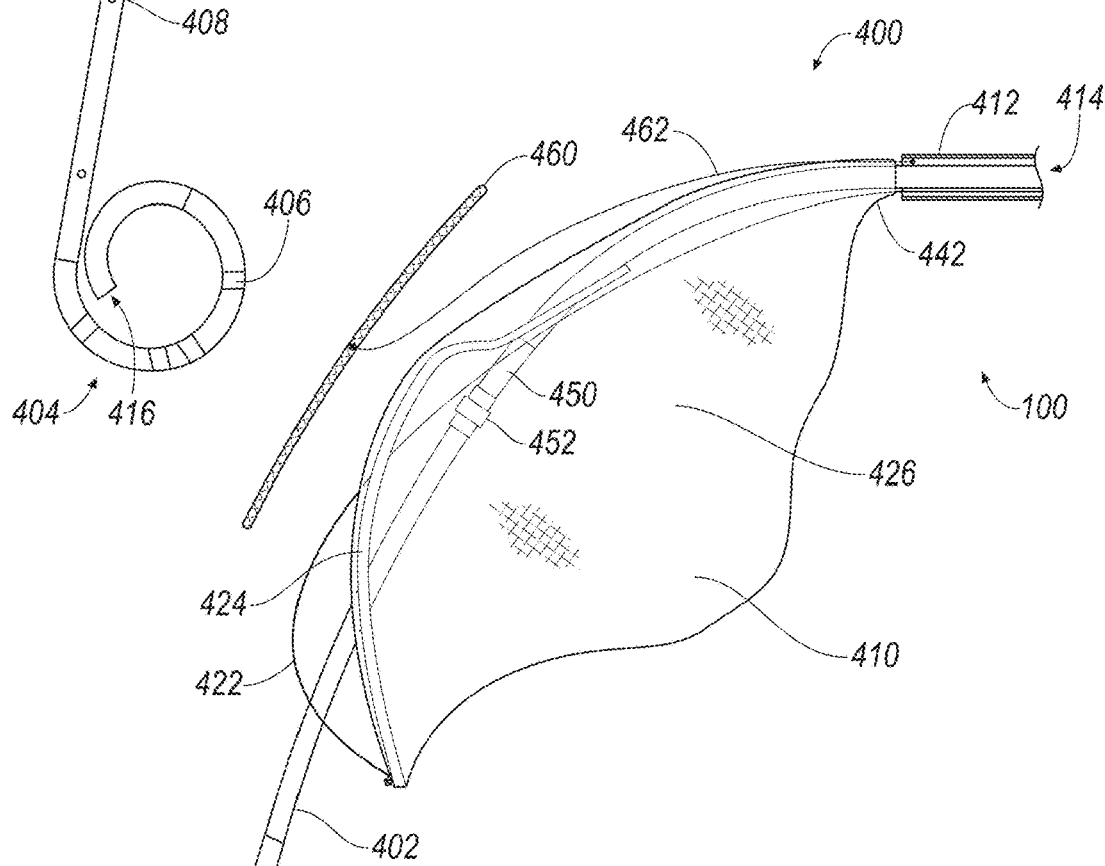
FIG. 4B
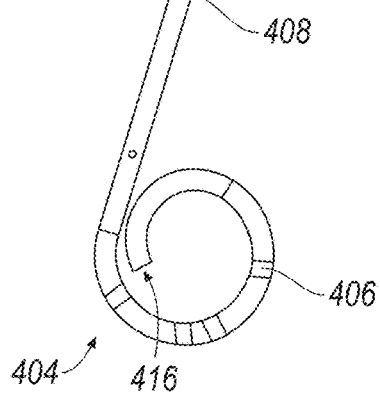

Subject 001-05
(0 Lesions)
Baseline
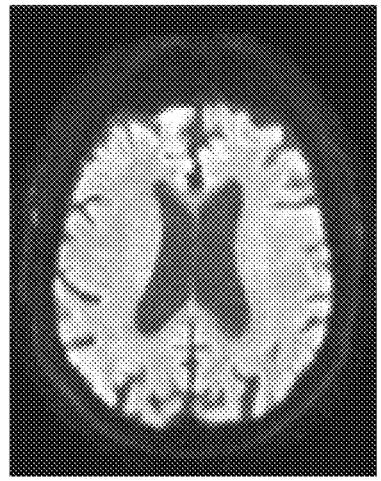 
Pre-Discharge
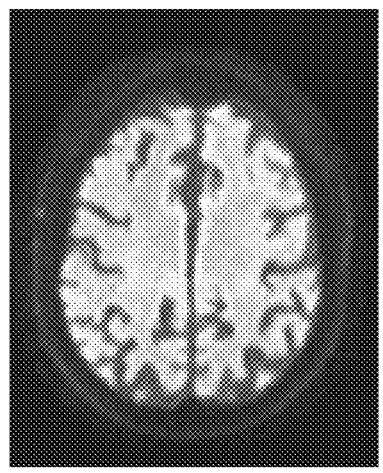 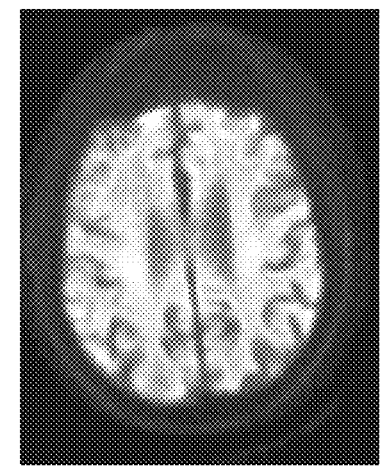
FIG.15A Subject 001-06
(9 Lesions, 193.9 mm³)
Baseline
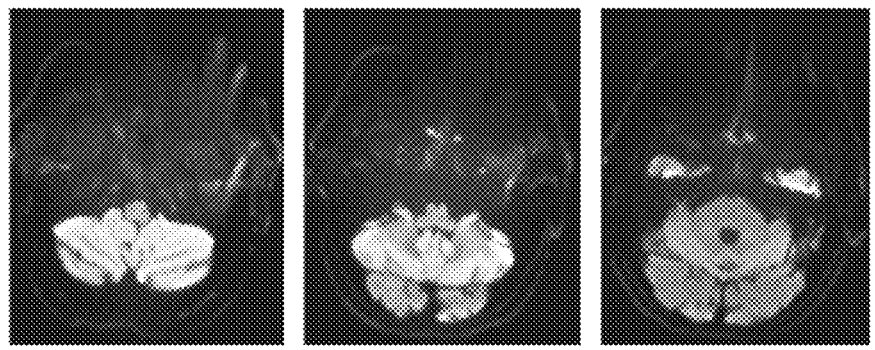
Pre-Discharge
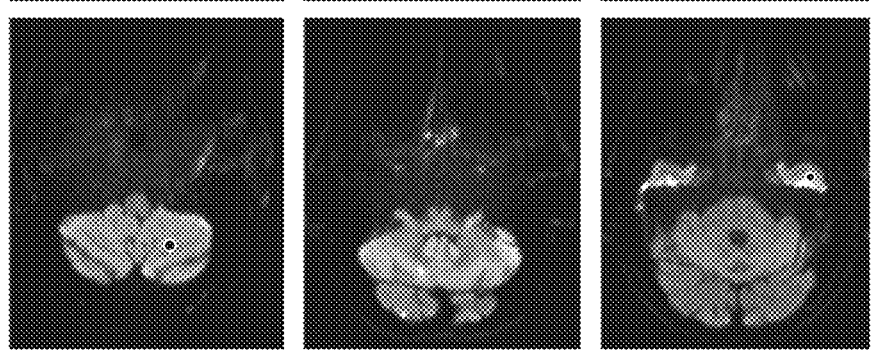
FIG. 15B
(9 Lesions, 193.9 mm³)
Baseline
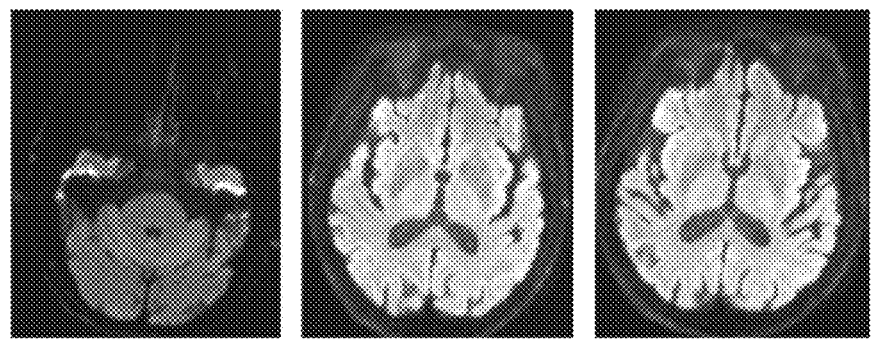
Pre-Discharge
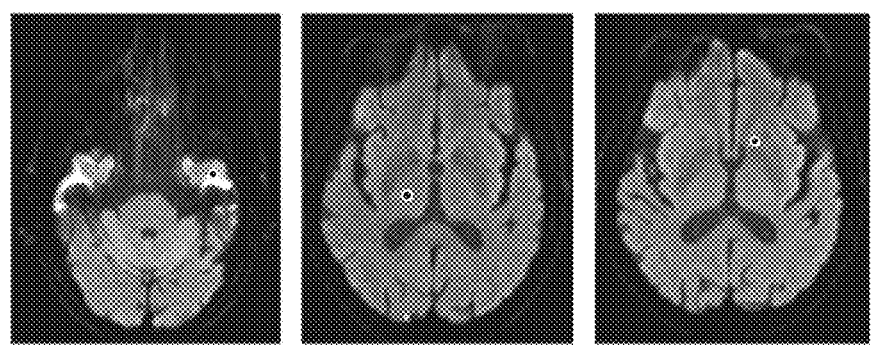
FIG. 15C Subject 001-06
(9 Lesions, 193.9 mm³)

Subject 002-01
(15 Lesions, 1200.1 mm³)

Subject 002-01
(15 Lesions, 1200.1 mm³)

Subject 002-01
(15 Lesions, 1200.1 mm³)

Subject 002-01
(15 Lesions. 1200.1 mm³)

Subject 002-01
(15 Lesions, 1200.1 mm³)

Subject 002-01
(15 Lesions, 1200.1 mm$^3$)
Baseline
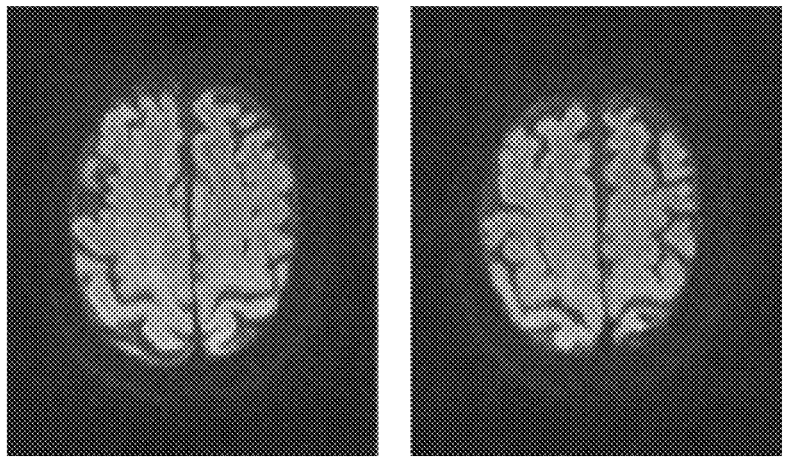
Pre-Discharge
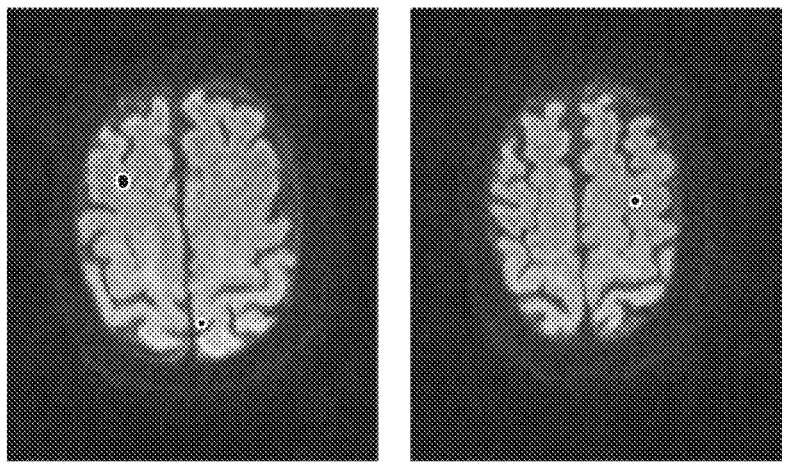
FIG. 15J

EMBOLIC PROTECTION DEVICE

CROSS REFERENCE TO RELATED APPLICATION

This application is a continuation of PCT application no. PCT/US2019/020952, filed Mar. 6, 2019, which claims the benefit of U.S. provisional application No. 62/639,618, filed on Mar. 7, 2018, and U.S. provisional application No. 62/812,391, filed on Mar. 1, 2019. Each of these documents is hereby incorporated by reference in its entirety.

TECHNICAL FIELD

This application relates to embolic protection devices including a catheter and methods of using such embolic protection devices in medical procedures (e.g., closed-heart surgical procedures).

BACKGROUND

Traditional pigtail catheters are used during percutaneous cardiac procedures where the positioning of various instruments and devices within the vasculature of a patient is important. These pigtail catheters comprise a curved distal end that can rest within the patient's anatomy (e.g., an artery (e.g., aorta)) and hold the catheter in place while other instrumentation and devices are delivered into the patient's vasculature. Some traditional pigtail catheters include a lumen and small apertures at their distal ends through which a contrast agent can be injected into a patient's vasculature for imaging the relevant portion of the patient's anatomy and identifying anatomical landmarks.

However, the use of traditional pigtail catheters in percutaneous cardiac procedures often results in serious and life-threatening complications for the patient. For example, cerebral embolism is a common complication in cardiac procedures, such as valve replacement and repair, where a traditional pigtail catheter is deployed. During such procedures, plaque, calcium, thrombi, or any combination thereof, in the vessels, valves, and/or cardiac chambers can be dislodged by the catheter or other medical devices introduced into the patient's vasculature. The dislodged plaque, calcium, thrombi or any combination thereof can be carried into the patient's brain via blood flow from the aorta and can cause blockages therein leading to an embolic event such as stroke. Approximately 2.9%-6.7% of patients undergoing transfemoral transcatheter aortic-valve implantation (TAVI) have a stroke within 30 days, and even more (4.5%-10.6%) have a stroke within a year, often leading to death. Furthermore, up to 85% of patients undergoing TAVI have evidence of embolic phenomenon to the brain based on neuroimaging studies. Although clinically silent, such embolic phenomena are associated with cognitive decline (Astraci 2011; Ghanem 2010; Kahlert 2010; Rodes-Caban 2011).

Presently, there are a few devices on the market designed to protect the brain, abdominal organs, and carotid arteries from emboli, and these devices suffer from various significant drawbacks. For instance, the Embrella Embolic Deflector®, available from Edwards Lifesciences of Irvine, Calif., employs a deflector that deflects emboli from the carotid arteries into the descending aorta, but the device does not trap the emboli, so emboli are free to travel to other areas of the body and cause deleterious complications. The EMBOL-X®, also available from Edwards Lifesciences, employs a filtering screen, but this device is designed for use in open heart procedures, which present additional medical risks and increased morbidity. Additionally, the use of multiple devices, for example a catheter for visualization and a separate filter device, lengthens the procedure time and increases the risk of complications to the patient.

SUMMARY

These and other needs are met by the present invention, which presents an embolic protection device comprising a deployable embolic filter that is disposed around a catheter having a distal portion that can assume an arcuate configuration being at least a semi-circle, and having a wire that is operable to manipulate the embolic filter into a configuration that more fully engages a body lumen.

The combination of the catheter and the embolic filter in the same device may provide the benefits of both devices individually, as well as provide a synergistic effect. For example, the integration of the catheter and the embolic filter can decrease the duration of the medical procedure and reduce the occurrence of complications (e.g., complications caused by dislodged emboli). In other examples, the expansion of the embolic filter may help to anchor the catheter into position to provide a more accurate position of the catheter than if the position of the catheter is susceptible to the influences of blood flow, tissue movement, and the like. In a valve replacement procedure, anchoring of the catheter and more accurate positioning of the catheter may help ensure that the valve prosthesis is properly positioned and stabilized. In another example, the position of the catheter may ensure that the filter is being properly positioned.

In some aspects, the embolic protection device comprises a catheter, a self-expanding embolic filter coupled to the catheter, a pull wire for reorienting the filter by bending a frame of the filter, and an outer sheath movable with respect to the embolic filter and the catheter. The outer sheath holds the embolic filter in a collapsed configuration when surrounding the embolic filter and is proximally retracted to deploy the embolic filter. The outer sheath may recapture the embolic filter and any debris captured therein by being distally advanced. The filter and outer sheath might both be movable with respect to the catheter, for example to be able to move the embolic filter longitudinally without having to move the entire catheter longitudinally. The pull wire is advantageous due to its ability to bend the frame, thereby facing the filter opening towards the distal end of the device and causing the embolic filter to more fully engage the body lumen.

In some aspects, the catheter has a proximal end and a distal end. A lumen extends from the proximal end of the catheter to the distal end of the catheter. In some embodiments, the lumen may be configured to house a guidewire.

In some aspects, the catheter is a pigtail catheter. A pigtail catheter is configured to curl at the distal end of the catheter, forming a generally arcuate shape that is at least a semi-circle. The pigtail may have a radiopaque marker viewable on x-rays or other medical imaging devices. The radiopaque marker is on the distal section of the curled pigtail in the form of a longitudinal marker, circumferential bands, or the like. The pigtail may additionally have one or more apertures to dispense drugs and/or contrast agents through the lumen.

In some aspects, a guidewire is inserted through the patient's skin and into a body lumen such as a femoral, radial, or brachial artery and steered near a target site. The guidewire is inserted into a lumen of the embolic protection device, and the embolic protection device is pushed or tracked over the guidewire to the target site. When the guidewire is retracted from at least the distal portion of the catheter, the catheter assumes a generally arcuate shape. The radiopaque marker on the catheter is used to visualize and position the catheter. Once the catheter is in position, the outer sheath is retracted to deploy the embolic filter and the pull wire is retracted to bend the frame of the filter to position the distal opening of the filter across the vessel. The user can then perform a procedure such as valve replacement, valve repair, radio frequency ablation, and the like. When the procedure is completed, the pull wire is advanced and the outer sheath is advanced to recapture the embolic filter and any debris trapped in the embolic filter. The device is then retracted from the vessel, with the catheter being atraumatic to vessels during retraction.

Another aspect is a method of capturing embolic debris during a closed-heart surgical procedure comprising inserting the distal end of the catheter of the embolic protection device into a body lumen. The method further comprises allowing the embolic filter to assume an expanded, deployed configuration and retracting the pull wire to bend the frame of the filter, so that a distal opening of the filter spans the body lumen.

In some aspects, the embolic protection device comprises a catheter, a self-expanding embolic filter coupled to the catheter, a push wire for reorienting the filter by bending a frame of the filter in a longitudinal direction and extending the frame in a radial direction, and an outer sheath movable with respect to the embolic filter and the catheter. The outer sheath holds the embolic filter in a collapsed configuration when surrounding the embolic filter and is proximally retracted to deploy the embolic filter. The outer sheath may recapture the embolic filter and any debris captured therein by being distally advanced. The push wire is advantageous due to its ability to bend and extend the frame, thereby facing the filter opening towards the distal end of the device and causing the embolic filter to more fully engage the body lumen.

In some aspects, the catheter has a proximal end and a distal end. A lumen extends from the proximal end to the distal end along a longitudinal axis of the catheter. In some embodiments, the lumen may be configured to house a guidewire.

In some aspects, the catheter is a pigtail catheter. A pigtail catheter is configured to curl at the distal end of the catheter, forming a generally arcuate shape that is at least a semi-circle. The pigtail may have a radiopaque marker viewable on x-rays or other medical imaging devices. The radiopaque marker is on the distal section of the curled pigtail in the form of a longitudinal marker, circumferential bands, or the like. The pigtail may additionally have one or more apertures to dispense drugs and/or contrast agents through the lumen.

In some aspects, a guidewire is inserted through the patient's skin and into a body lumen such as a femoral, radial, or brachial artery and steered near a target site. The guidewire is inserted into a lumen of the embolic protection device, and the embolic protection device is pushed or tracked over the guidewire to the target site. When the guidewire is retracted from at least the distal portion of the catheter, the catheter assumes a generally arcuate shape. The radiopaque marker on the catheter is used to visualize and position the catheter. Once the catheter is in position, the outer sheath is retracted to deploy the embolic filter and the push wire is advanced to bend and extend the frame of the filter to position the distal opening of the embolic filter across the vessel. The user can then perform a procedure such as valve replacement, valve repair, radio frequency ablation, and the like. When the procedure is completed, the push wire is retracted and the outer sheath is advanced to recapture the embolic filter and any debris trapped in the embolic filter. The device is then retracted from the vessel, with the catheter being atraumatic to vessels during retraction.

Another aspect is a method of capturing embolic debris during a closed-heart surgical procedure comprising inserting the distal end of the catheter of the embolic protection device into a body lumen. The method further comprises allowing the embolic filter to assume an expanded, deployed configuration and advancing the push wire to bend and extend the frame of the filter, so that a distal opening of the filter spans the body lumen.

BRIEF DESCRIPTION OF THE FIGURES

The following figures are provided by way of example and are not intended to limit the scope of the claimed invention.

In FIG. 1A, an embolic filter of the embolic protection device is illustrated in a collapsed (undeployed) configuration. In FIG. 1B, the embolic filter is illustrated in an expanded (deployed) configuration wherein a pull wire affixed to a frame of the embolic filter is advanced to a distal position so that the frame assumes it's self-expanded and undeflected (i.e., unbent) configuration.

FIGS. 1E and 1F illustrate front views of an embodiment of an embolic filter frame of the present invention. In FIG. 1E, the filter frame is undeployed wherein the frame is collapsed and enclosed by an outer sheath. In FIG. 1F, the outer sheath is longitudinally retracted and the filter frame is deployed to its self-expanded configuration.

FIGS. 2A-2B illustrate partial side views of an embodiment of an embolic protection device of the present invention comprising a shoulder.

FIGS. 3A-3D illustrate partial side views of an embodiment of an embolic protection device of the present invention comprising an intermediate tube.

FIGS. 4A-4C illustrate partial side views of an embodiment of an embolic protection device of the present invention comprising a deflector.

In FIG. 13A, the embolic protection device comprises a longitudinal groove in which a second catheter is inserted alongside the embolic protection device. In FIG. 13B, the second catheter is situated adjacent to the embolic protection device that lacks a longitudinal groove.

FIGS. 15A-15J are images generated from diffusion-weighted magnetic resonance imaging (DW-MRI) of representative subjects according to Example 2.

Like reference numerals in the various drawings indicate like elements.

DETAILED DESCRIPTION

The present invention provides an embolic protection device and methods of using the embolic protection device for capturing embolic debris during surgical procedures.

I. DEFINITIONS

As used herein, the term "self-expanding" means to increase, spread out, or unfold from a collapsed state upon the withdrawal or removal of a restricting or confining force.

As used herein, the term "closed-heart" refers to any surgical procedure involving the heart, wherein the chest cavity is not opened.

As used herein, the term "woven" refers to any material that comprises a plurality of strands, wherein the strands are interlaced to form a net, mesh, or screen. Without limitation, examples of woven materials include netting or mesh comprising a polymer, metal, or metal alloy.

As used herein, the term "non-woven" refers to any material that comprises a continuous film. Non-woven material may be permeable, semi-permeable, or non-permeable. For example, permeable or semi-permeable non-woven material may optionally include one or more pores through which a fluid may pass.

As used herein, the term "alloy" refers to a homogenous mixture or solid solution produced by combining two or more metallic elements, for example, to give greater strength or resistance to corrosion. For example, alloys include brass, bronze, steel, nitinol, chromium cobalt, MP35N, 35NLT, elgiloy, and the like.

As used herein, "nitinol" and "nickel titanium" are used interchangeably to refer to an alloy of nickel and titanium.

As used herein, "chromium cobalt" refers to an alloy of chromium and cobalt.

As used herein, "MP35N" refers to an alloy of nickel and cobalt.

As used herein, "35NLT" refers to a cobalt-based alloy that may also comprise chromium, nickel, molybdenum, carbon, manganese, silicon, phosphorus, sulfur, titanium, iron, and boron.

As used herein, "elgiloy" refers to an alloy of cobalt, chromium, nickel, iron, molybdenum, and manganese.

As used herein, a "body lumen" refers to the inside space of a tubular structure in the body, such as an artery, intestine, vein, gastrointestinal tract, bronchi, renal tubules, and urinary collecting ducts. In some instances, a body lumen refers to the aorta.

II. EMBOLIC PROTECTION DEVICES

Although certain embodiments and examples are described below, those skilled in the art will recognize that the disclosure extends beyond the specifically disclosed embodiments and/or uses and obvious modifications and equivalents thereof. Thus, it is intended that the scope of the disclosure herein presented should not be limited by any particular embodiments described below.

Figure 1A:
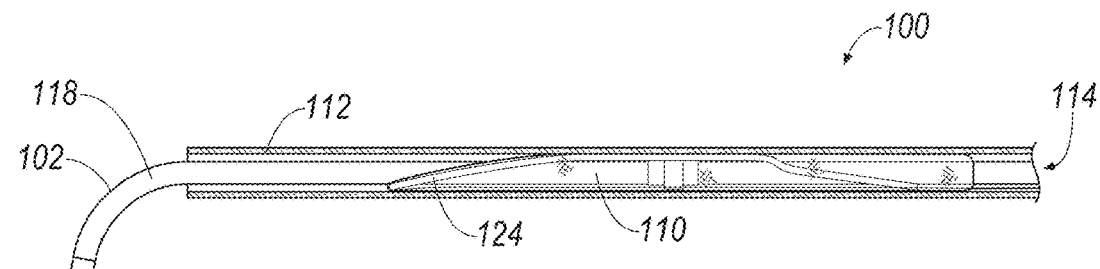
FIGS. 1A and 1B illustrate partial side views of an embodiment of an embolic protection device of the present invention.
Figure 1B:
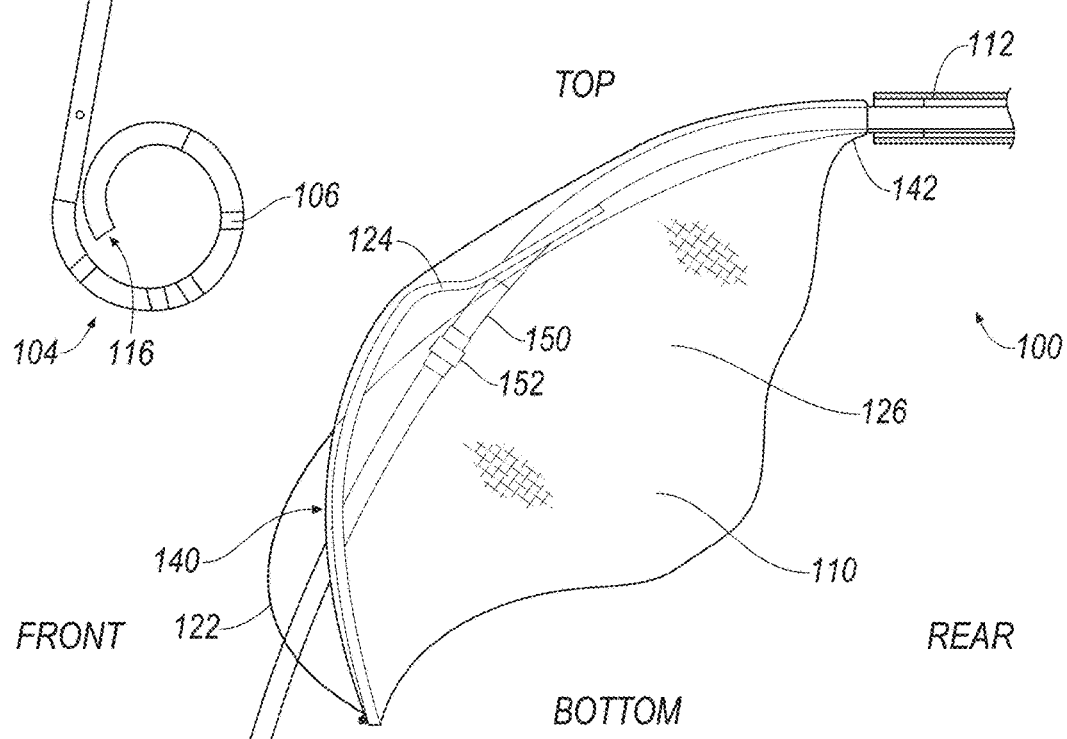
Figure 6A:
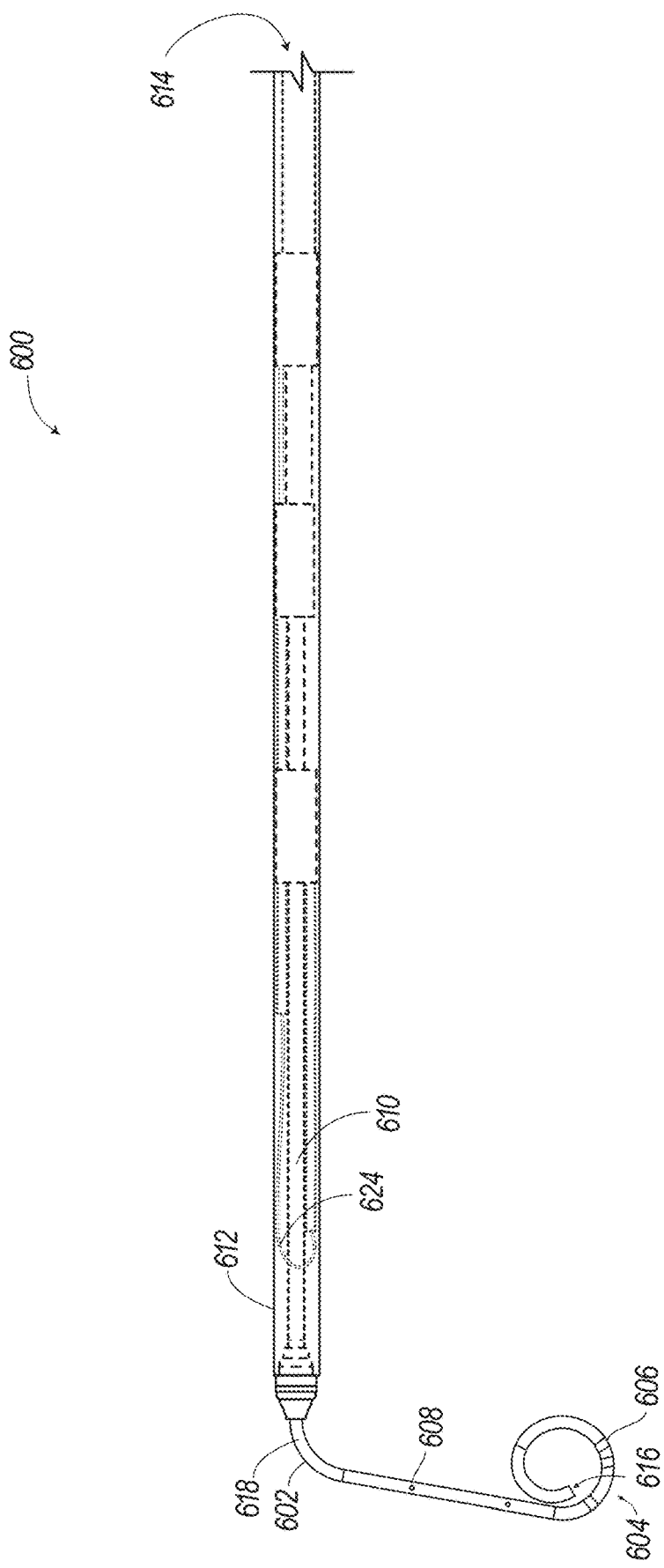
FIG. 6A illustrates a partial side view of an embodiment of an embolic protection device of the present invention with an embolic filter in a collapsed (undeployed) configuration.
Figure 6B:
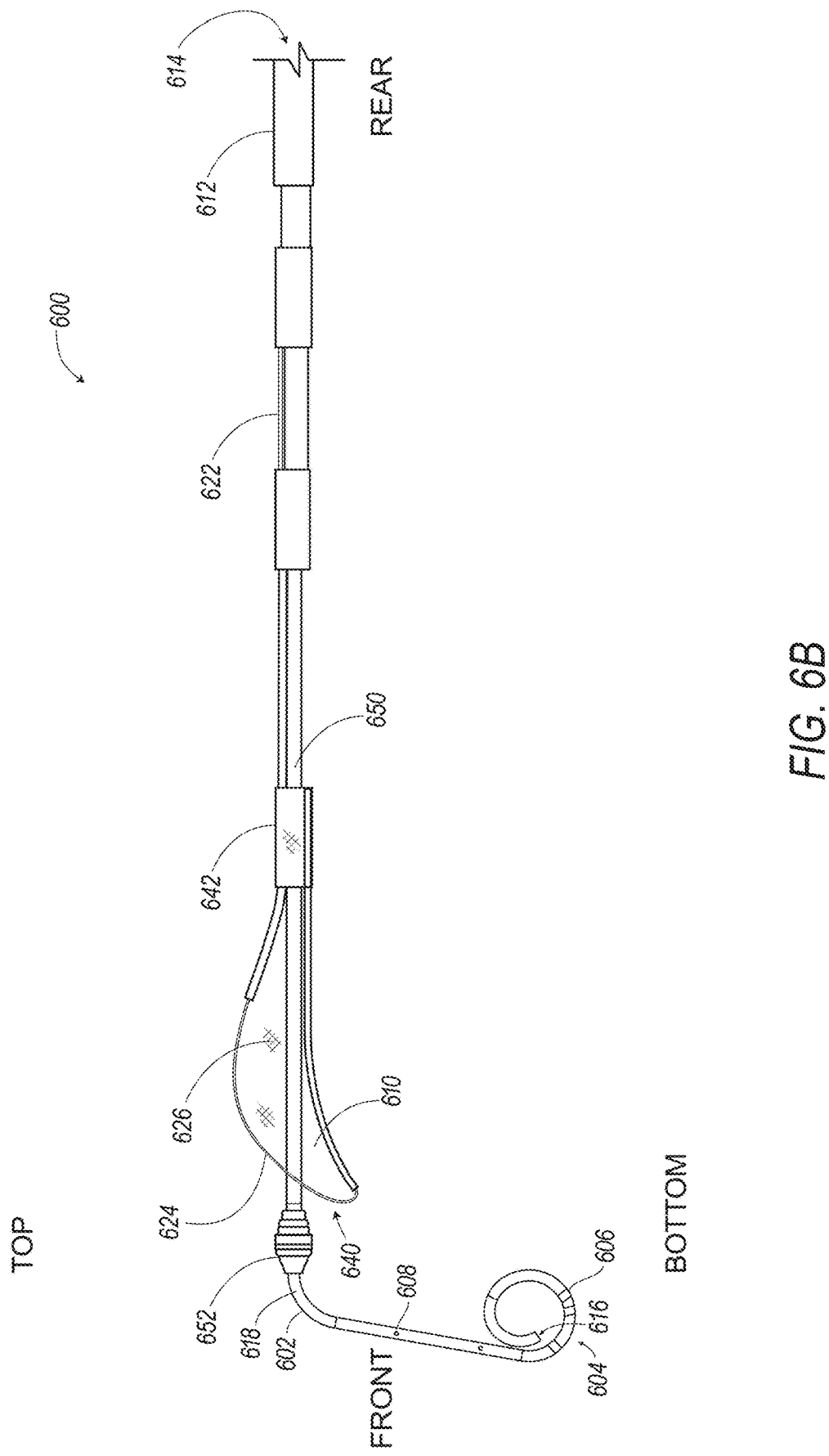
FIGS. 6B and 6C illustrate a side view and a front end view of the embolic filter in an self-expanded (deployed) configuration, respectively, wherein a push wire coupled to a frame of the embolic filter is retracted to a proximal position so that the frame assumes an undeflected (i.e., unbent) configuration.
Figure 6C:
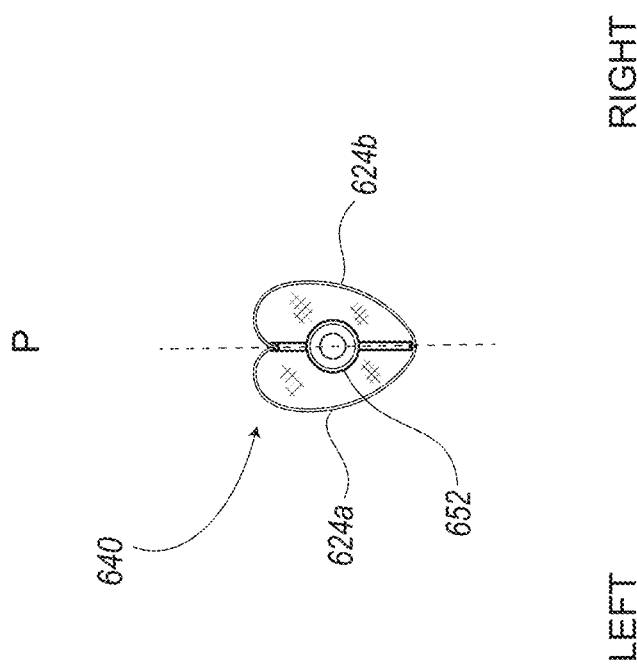

For purposes of this disclosure, the terms "upper," "lower," "right," "left," "rear," "front," "vertical," "horizontal," and derivatives thereof shall relate to the invention as oriented in FIGS. 1B and 1F (or in FIGS. 6B and 6C). However, it is to be understood that the invention may assume various alternative orientations, except where expressly specified to the contrary. Also, for purposes of this disclosure, the term "coupled" (in all of its forms, couple, coupling, coupled, etc.) generally means the joining of two components (electrical or mechanical) directly or indirectly to one another. Such joining may be stationary in nature or movable in nature; may be achieved with the two components (electrical or mechanical) and any additional intermediate members being integrally formed as a single unitary body with one another or with the two components; and may be permanent in nature or may be removable or releasable in nature, unless otherwise stated.

FIGS. 1A and 1B illustrate embodiments of an embolic protection device 100. In these embodiments, the device 100 comprises a catheter 102 (e.g., a pigtail catheter) having a proximal end 114, a distal end 116, and a lumen 118 extending from the proximal end 114 to the distal end 116. The lumen 118 may be configured to house a guidewire 990 (see FIGS. 9A and 9B) that is longitudinally moveable through this lumen to coil or straighten the distal portion 104 of the catheter 102 depending on whether the guidewire is retracted (to coil the distal portion) or extended (to straighten the distal portion). In some embodiments, the catheter 102 includes a distal portion 104 configured to assume a generally arcuate shape being at least a semi-circle. A side wall of the catheter 102 may optionally include one or more apertures 108 in the distal portion 104 that are configured to deliver one or more fluids (e.g., imaging dye, contrast agent, oxygenated blood, saline, any combination thereof, or the like) to a body lumen 992 (see FIG. 9A). The apertures 108 (the plural intended to include embodiments in which the distal portion includes one aperture 108) are in fluid communication with the lumen 118. In some embodiments, the distal portion 104 of the catheter 102 includes one or more radiopaque markers 106. In some embodiments, the radiopaque markers 106 are wrapped around the circumference of the distal portion of the catheter and can have the same or different widths. In other embodiments, the radiopaque markers are co-linear with the lumen and extend to the distal end of the catheter. The device 100 further comprises a self-expanding embolic filter 110 defined by a frame 124 and a filter medium 126, and a deployment mechanism 112 (e.g., a longitudinally retractable outer sheath or a longitudinally retractable ring). The embolic filter 110 is disposed around the catheter 102.

As illustrated in FIG. 1B, in its deployed configuration, the embolic filter 110 includes a distal opening 140 that is defined by the frame 124, faces the distal end 116 of the catheter 102, and extends proximally from the distal opening 140 to a closed proximal end 142. The device 100 further comprises a pull wire 122 that is coupled to the frame 124 and can be retracted to deflect or bend the frame 124 and change the orientation and shape of the distal opening 140.

In some embodiments, retracting the pull wire 122 may cause the distal opening 140 of the embolic filter 110 to engage at least a portion of the interior body lumen 992 (see FIG. 9D) wall. FIG. 1B illustrates the pull wire 122 in an advanced, i.e., un-retracted or self-expanded, configuration with the frame oriented generally to extend in a distal longitudinal direction, albeit angled back somewhat (e.g., less than about 45 degrees) in a lateral direction. The catheter 102 may be partially surrounded towards its proximal end 114 by a support catheter 150 that terminates at a head 152, proximal to the distal portion 104 of the catheter 102. The support catheter 150 may be made of a thicker, stiffer material to add rigidity and provide a protective or supporting layer surrounding the catheter 102.

Figure 1C:
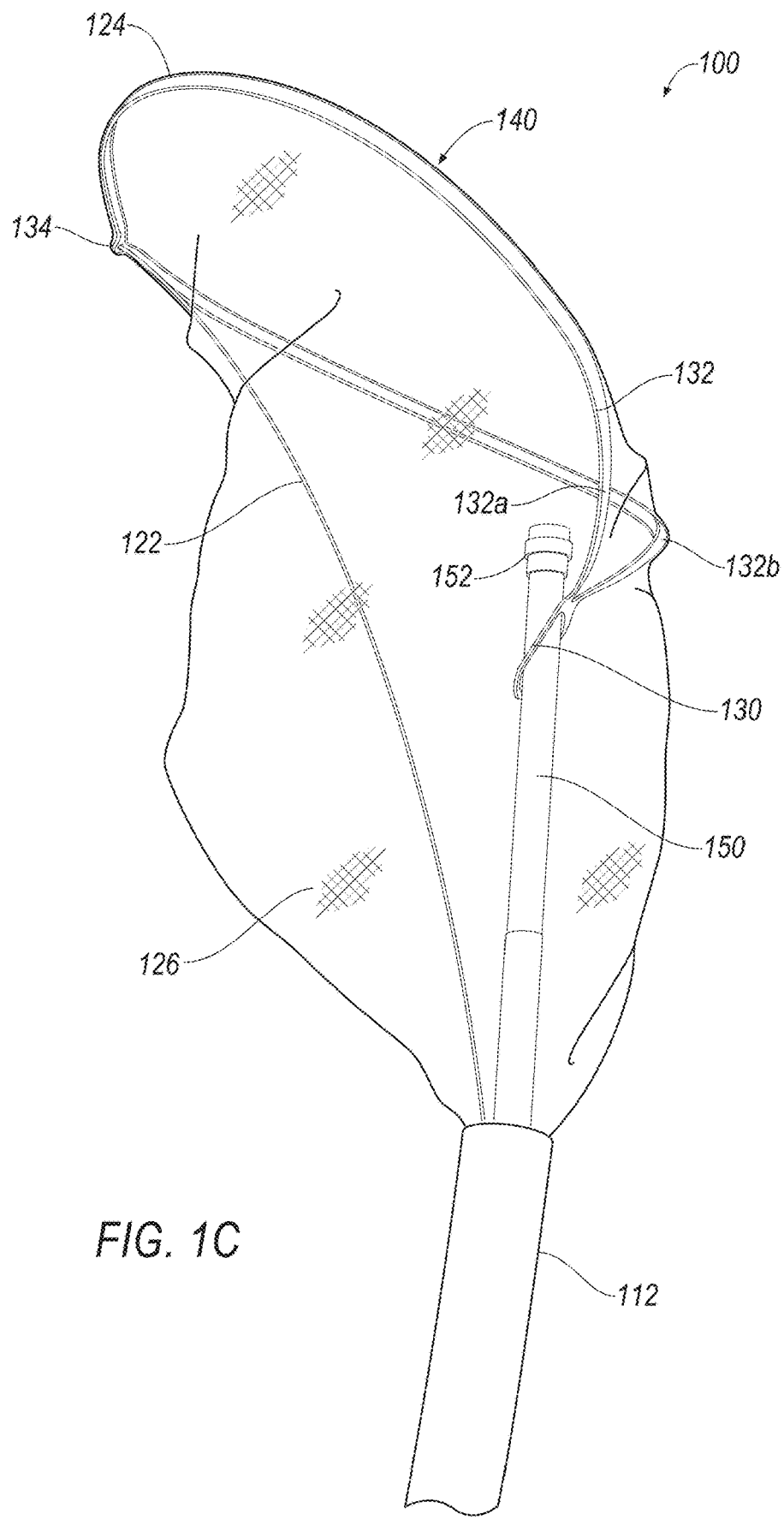
FIG. 1C illustrates a side perspective view of an embodiment of an embolic filter of the present invention assuming a partially deflected (i.e., partially bent) configuration wherein the pull wire affixed to the frame of the embolic filter is partially longitudinally retracted to a proximal position.

FIG. 1C illustrates the embolic filter 110 deployed (e.g., self-expanded) by retraction of the deployment mechanism (e.g., outer sheath) 112 with the frame 124 partially deflected, i.e., partially bent, by retraction of the pull wire 122. The pull wire 122 is coupled to the frame 124 at a distal coupling 134. The distal opening 140 is primarily defined by a first portion 132 of the frame 124. The first portion 132 of the frame 124 defines a shape of the distal opening 140 that is substantially elliptical (i.e., shaped like an ellipse), or alternatively, substantially oval-shaped or circular. In this embodiment, the portion 132 of the frame 124 may be substantially elliptical and may terminate a V-shaped point at its proximal end, i.e., the portion 132 of the frame 124 may invert its curvature at one end of its substantially elliptical shape (e.g., at its distal end) and come to a point at its proximal end. The distal opening 140 may substantially be defined by the frame 124, but may span across the frame 124 adjacent to the section of the frame 124 that comes to a point. The filter medium 126 may define a portion of the distal opening 140 where the filter medium 126 spans across the frame 124, i.e., adjacent to a point of attachment of the frame 124 to the catheter 102 or support catheter 150.

The attachment of the frame 124 to the support catheter 150 (or alternatively, directly to the catheter 102) is accomplished via a second portion 130 of the frame 124, which encircles the support catheter 150 (or catheter 102) and is at an angle with respect to the longitudinal axis of the catheter 102. The second portion 130 of the frame 124 may be fixed in its position by friction and by tension of the embolic filter 110 in the lateral and/or longitudinal directions. In other embodiments, the fixed attachment of the second portion 130 of the frame 124 to the support catheter 150 (or catheter 102) may also be accomplished via adhesives, welding, or the like.

The first portion 132 of the frame 124 may extend in a first lateral direction away from the catheter 102 and away from the second portion 130 of the catheter 102 and loop back across the catheter 102 and extend in the opposite lateral direction. In this embodiment, the first portion 132 of the frame 124 comprises two sides (132a, 132b) that each extend generally in a first lateral direction away from the catheter 102 and then loop back on opposite sides around the catheter 102 and extend generally in the opposite lateral direction before converging and meeting to form the substantially elliptical shape. As shown in FIG. 1F, the embolic filter 110 is symmetrical about the pull wire 122. For ease of discussion, the embolic filter 110 is referred as having a left side and a right side. Elements on the left side of the embolic filter 110 are mirrored by elements on the right side of the embolic filter 110.

When the pull wire 122 is in its advanced state (or partially, but not fully, retracted state), the frame 124 extends in a distal longitudinal direction as it extends from its attachment to the catheter 102 (or support catheter 150). When the pull wire 122 is in its retracted state (i.e., fully retracted) (see FIG. 1D and FIG. 9E), the frame 124 extends in a distal longitudinal direction near its point of attachment to the catheter 102, but then is bent such that it extends substantially perpendicular to the longitudinal axis of the catheter 102.

Figure 1D:
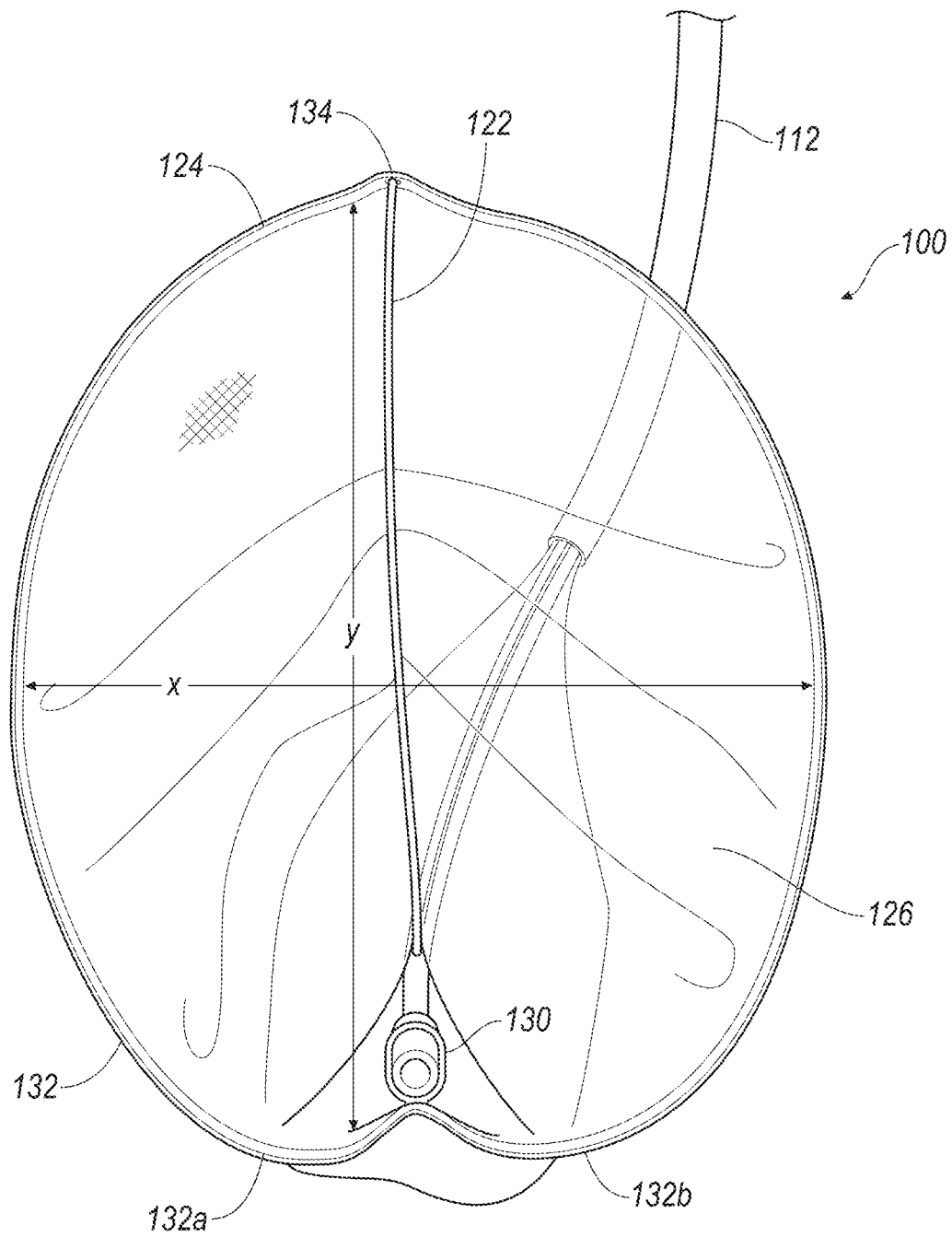
FIG. 1D illustrates a transverse cross-sectional view of an embodiment of an embolic filter of the present invention assuming a fully deflected (e.g., fully bent) configuration wherein the pull wire is fully longitudinally retracted thereby deflecting the filter.

FIG. 1D presents a cross-sectional view of the distal opening 140 of the embolic filter 110 when the embolic filter 110 assumes an expanded configuration and when the pull wire 122 is in a fully retracted state, fully deflecting (or bending) the frame 124. The pull wire 122 deflects or bends the frame 124 in a proximal longitudinal direction and laterally outward. In a fully deflected configuration (i.e., when the pull wire 122 is fully retracted), the distal opening 140 of the embolic filter 110 may be substantially perpendicular to the longitudinal axis of the catheter 102 and may span laterally across the body lumen 992 (see FIGS. 9D and 9E), substantially perpendicular to the longitudinal axis of the body lumen 992. The fully deflected (or bent) configuration may allow the embolic filter 110 to more fully engage the body lumen 992. In this fully deflected configuration, the distal opening 140 is substantially perpendicular to the longitudinal axis of the catheter 102. In the fully deflected configuration, the width, x, across the distal opening 140 may be increased compared to the corresponding dimension in the undeflected configuration. Likewise, in the fully deflected configuration, the length, y, across the distal opening 140 may be decreased compared to the corresponding dimension in the undeflected configuration. By increasing the width, x, in the bent configuration, the frame 124 defining the distal opening 140 may more fully engage the body lumen 992.

In the embodiments illustrated in each of FIGS. 1A-1D, the catheter 102 extends through the distal opening 140 of the embolic filter 110, and the frame 124 extends away from the catheter 102 in a first lateral direction and then curves back around the catheter 102 in the opposite direction.

The embolic protection device 100, with the embolic filter 110 deployed, i.e., the deployment mechanism 112 is retracted), may assume an undeflected (FIG. 1B), partially deflected (FIG. 1C), or fully deflected (FIGS. 1D and 5E) configuration. These configurations are achieved by engaging the pull wire 122 to a fully advanced, partially retracted (or partially advanced), or fully retracted state. In the fully advanced state, the pull wire 122 is in a distal position. In the fully retracted state, the pull wire 122 is in a proximal position. When longitudinally retracted to a proximal position, the pull wire 122 is configured to deflect (or bend) the frame 124 so that the distal opening 140 of the filter 110 is substantially perpendicular to the longitudinal direction of the catheter 102 and the distal opening 140 faces the distal end 116 of the catheter 102. When longitudinally advanced to a distal position, the pull wire 122 is configured to position the frame 124 so that the distal opening 140 of the filter 110 defined by the frame 124 is substantially parallel or angled less than about 45 degrees with respect to longitudinal direction of the catheter 102.

In some embodiments, the distal opening 140 of the embolic filter 110 has a diameter of from about 2 cm to about 6 cm (e.g., from about 2.5 cm to about 5 cm or about 4.5 cm). The embolic filter 110 can comprise any suitable size or diameter to accommodate anatomic variability in patients' body lumens 992 (see FIG. 9C). In some embodiments, the embolic filter 110 is coupled to the catheter 102 at the proximal and/or distal ends of the embolic filter 110 and/or at any other points there between. For example, the embolic filter 110 may be coupled to the catheter 102 via the frame 124, specifically the second portion 130 of the frame 124 (distal attachment) and also coupled to the catheter 102 via the filter medium 126 at an attachment point within the sheath 112.

FIGS. 1E and 1F illustrate the frame 124 of the embolic filter 110. In the embodiment illustrated in FIG. 1E, the frame 124 is collapsed within the outer sheath 112, i.e., with the sheath 112 advanced over the frame 124. In the embodiment illustrated in FIG. 1F, the frame 124 is deployed outside the sheath 112, i.e., with the sheath 112 retracted. The pull wire 122 is coupled to the frame 124 at a distal coupling 134. The pull wire 122 may be coupled to the frame 124 at the distal coupling 134 by a variety of methods, including by means of a hole in the frame 124 through which the pull wire 122 is threaded and crimped to hold it in place. The distal coupling 134 may also include a variation in the curvature of the frame 124, i.e., by inverting the curvature of the frame 124 and coming to a point. This curvature, along with the curvature of the frame 124 adjacent to the point of attachment of the frame 124 to the catheter 102, may aid in collapsing the frame 124 in order to advance the sheath 112 over the embolic filter 110. In some embodiments, the frame 124 comprises a shape memory material (e.g., a metal alloy or polymer). Examples of shape memory materials include, without limitation, nitinol, chromium cobalt, and/or other metal alloys such as MP35N, 35NLT, elgiloy, and the like. In some embodiments, the frame 124 is laser cut from a tube or a sheet.

FIGS. 2A and 2B illustrate embodiments of an alternative deployment mechanism for an embolic protection device 200 comprising a catheter 202, an embolic filter 210, and a movable outer sheath 212. In some embodiments, the outer sheath 212 can include an optional lip 260 protruding inwardly from the distal end of the outer sheath 212. The catheter 202 can include one or more shoulders 262 (e.g., a distal shoulder 262a and a proximal shoulder 262b) protruding outwardly from an outer wall of the catheter 202. The lip 260 of the outer sheath 212 is configured to engage the shoulder or shoulders 262 of the catheter 202 to inhibit or prevent the outer sheath 212 from moving excessively in either the proximal or distal direction. The lip 260 and shoulder 262 may be arcuate, pronged, and combinations thereof, and the like.

In some embodiments, the outer sheath 212 and/or the catheter 202 comprise nubs and/or detents configured to provide information to the user about the longitudinal position of the outer sheath without inhibiting further movement. In some embodiments, the outer sheath 212 and the catheter 202 comprise lips 260, shoulders 262, and detents and nubs (e.g., to inhibit longitudinal movement of the outer sheath 212 excessively in either direction, and to provide information about the extent of movement of the outer sheath 212 relative to the catheter 202 (e.g., ½ retracted, ¼ retracted, etc.)).

Benefits of the outer sheath 212 deployment mechanism may include its simplicity, ease of operation, and small number of moving parts. The embolic protection device 200 is well-suited for use in conjunction with delicate cardiac procedures having serious risks. As the duration of the procedure increases, the risk of complications typically increases as well. Therefore, it can be advantageous that the user be able to quickly and easily deploy and recapture the embolic filter 210. A more complicated device could be more difficult to operate and could be more likely to malfunction or cause adverse effects. The ability to move the outer sheath 212 relative to the embolic filter 210 can advantageously allow the user to partially recapture the embolic filter 210, for example to adjust the width of the distal opening 140. In some embodiments, narrowing the distal opening 140 allows the user to introduce a second catheter or instrument to the patient's body lumen 992 (see FIG. 9D) and maneuver the second catheter or instrument around and past the catheter 202 and embolic filter 210, as described herein. In some embodiments, an embolic protection device as described herein may have a longitudinally extending groove (not shown) along its surface, e.g., along the catheter 102, along the support catheter 150 or along the deployment mechanism (e.g. outer sheath) 112. In such embodiments, a second catheter or instrument may be inserted while engaging the groove to guide the second device alongside the embolic protection device.

FIGS. 3A-3D illustrate embodiments of an embolic protection device 300 in which an embolic filter 310 is movably coupled to a catheter 302 by way of a frame 324 and is longitudinally movable with respect to the catheter 302. In some embodiments, the embolic filter 310 is coupled to an intermediate tube 330 that at least partially circumferentially surrounds the catheter 302. The intermediate tube 330 is longitudinally movable with respect to the catheter 302. An outer sheath 312 is configured to at least partially circumferentially surround both the catheter 302 and the intermediate tube 330. The intermediate tube 330 and the outer sheath 312 can be moved simultaneously and independently. The longitudinal position of the embolic filter 310 with respect to the catheter 302 can be adjusted while the embolic filter 310 is in the collapsed configuration or in a deployed or partially deployed, expanded configuration. In some embodiments, the perimeter of the distal opening of the embolic filter 310 comprises one or more radiopaque markers to allow the user to visualize the position of the distal opening, for example, with respect to various anatomical landmarks. For example, if the user is performing a procedure on a patient's aortic valve and wants to prevent emboli from entering the cerebral arteries, the radiopaque markers can be used to ensure the distal opening of the embolic filter 310 is positioned in the ascending aorta upstream from the carotid arteries.

FIG. 3A illustrates the embolic filter 310 confined in a closed configuration by the outer sheath 312 and a distal end of intermediate tube 330 at position (a). If the intermediate tube 330 is held stationary at position (a), the outer sheath 312 can be retracted to deploy the embolic filter 310, as shown in FIG. 3C. If the intermediate tube 330 and outer sheath 312 are instead moved simultaneously, the embolic filter 310 remains confined by the outer sheath 312 while the longitudinal position of the embolic filter 310 is adjusted. For example, FIG. 3B illustrates the embolic filter 310 still confined by outer sheath 312, while the intermediate tube 330 has been retracted so that the distal end of the intermediate tube 330 is at position (b). If the intermediate tube 330 is then held stationary at position (b), the outer sheath 312 can be retracted to deploy the embolic filter 310, as shown in FIG. 3D. The intermediate tube 330 and outer sheath 312 can be moved to adjust the longitudinal position of the embolic filter 310 in a deployed or partially deployed configuration. For example, the intermediate tube 330 and outer sheath 312 can be moved simultaneously to retract the intermediate tube 330 from the position as shown in FIG. 3C to position (b) as shown in FIG. 3D.

In addition to those described in detail herein, a wide variety of deployment mechanisms for embolic filters are possible. For example, a deployment system may comprise a portion of an annular sheath including inward end protrusions that are guided in tracks along the catheter body. Certain such embodiments may advantageously reduce the profile of the catheter. For another example, a deployment system may comprise a threaded sheath that longitudinally moves upon twisting by the user. For yet another example, a deployment system may comprise a plurality of annular bands that can capture the embolic filter longitudinally and/or circumferentially. Combinations of the deployment systems described herein and other deployment systems are also possible.

Figure 4C:
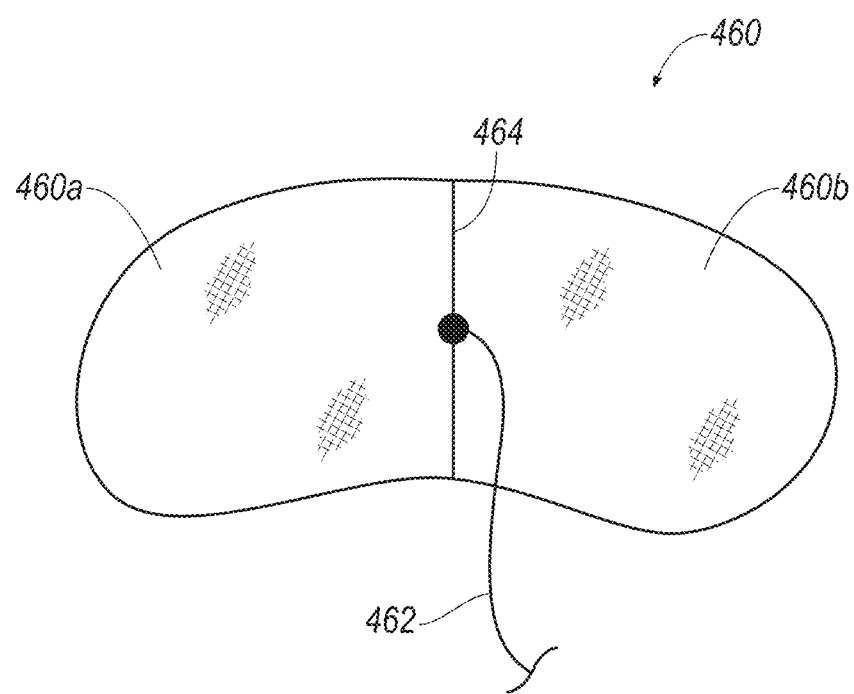

FIGS. 4A-4C illustrate another embodiment of an embolic protection device 400 comprising a catheter 402, a deflector 460, an embolic filter 410, and a movable outer sheath 412. In some embodiments, the embolic protection device 400 is similar to embolic protection device 100 with the addition of the deflector 460.

Various types and designs of deflectors can be used with an embolic protection device such as embolic protection device 400. Such deflectors can have different shapes and/or sizes and can vary in where and how they are coupled to the catheter. For example, deflectors can be made in various sizes, for example to accommodate differences in patient anatomy. In some embodiments, the deflector comprises a shape memory material, for example including nitinol, chromium cobalt, and/or alloys such as MP35N, 35NLT, elgiloy, and the like. In some embodiments, the deflector comprises a porous membrane, for example a semi-permeable polyurethane membrane/material, mounted to a self-expanding frame, for example a frame comprising a shape memory material.

An example of the deflector 460 shown in FIGS. 4A-4C has a generally butterfly or elliptical shape with two wings or petals 460a and 460b extending to either side of a central axis 464. The wings or petals 460a and 460b may be the same or different in size shape, material, and the like. The deflector 460 is coupled to a side of the catheter 402 via an elongate member 462 that is coupled (e.g., by adhering, welding, soldering, coupling using a separate component, combinations thereof, and the like) at one end to the central axis 464 of the deflector 460 and at the other end to the catheter 402. In some embodiments, the elongate member 462 comprises a shape memory material, for example including nitinol, chromium cobalt, and/or alloys such as MP35N, 35NLT, elgiloy, and the like that is configured (e.g., shape set) to bias the deflector away from the catheter 402. The deflector 460 is configured to release to an open configuration, shown in FIGS. 4B and 4C, when not confined by, for example, an outer sheath 412. In some embodiments, the deflector 460 is configured to fold along the central axis 464 away from the elongate member 462 so that the wings or petals 460a and 460b come together and the deflector 460 can be contained in, for example, an outer sheath 412, as shown in FIG. 4A. As shown in FIG. 4A, the deflector 460 can initially be folded and contained in the outer sheath 412 such that the wings or petals 460a and 460b are positioned distal to the central axis 464. In some embodiments, the deflector 460 can initially be folded in the opposite direction such that the wings or petals 460a and 460b are positioned proximal to the central axis 464.

In some embodiments, the catheter 402 is a pigtail-type catheter as shown in FIGS. 4A and 4B and described herein. The catheter 402 includes a distal portion 404 configured to assume a generally arcuate shape being at least a semi-circle. In some embodiments, the distal portion 404 of the catheter 402 includes one or more radiopaque markers 406. A side wall of the catheter 402 may optionally include one or more apertures 408 in the distal portion 404 that are configured to deliver one or more fluids (e.g., imaging dye, contrast agent, oxygenated blood, saline, any combination thereof, or the like) to a body lumen.

The catheter 402 has a proximal end 414 and a distal end 416. As shown in the FIG. 4B, an example of the catheter 402 is partially surrounded towards its proximal end 414 by a support catheter 450 that terminates at a head 452, proximal to the distal portion 404 of the catheter 402. The support catheter 450 may be made of a thicker, stiffer material to add rigidity and provide a protective or supporting layer surrounding the catheter 402.

As illustrated in FIG. 4B, the embolic filter 410 comprises a frame 424 and a filter medium 426. In its deployed configuration, the embolic filter 410 includes a distal opening 440 defined by the frame 424, faces the distal end 416 of the catheter 402, and extends proximally from the distal opening 440 to a closed proximal end 442. The device 400 further comprises a pull wire 422 that is coupled to the frame 424 and can be retracted to deflect or bend the frame 424 and change the orientation and shape of the distal opening 440, in manner similar to that described above with reference to FIGS. 1B-1D.

In some embodiments, the deflector 460 and embolic filter 410 can be coupled to another type of catheter, for example a catheter without a distal portion configured to assume an arcuate shape. The embolic filter 410 can be similar to the embolic filters 110 and 210 shown in FIGS. 1A-1D; FIGS.

2A and 2B; and described herein. In some embodiments, the embolic filter 410 is coupled to the catheter 402 proximal to the deflector 460, for example as shown in FIGS. 4A-4B. In some embodiments, the embolic filter 410 is coupled to the catheter 402 distal to the deflector 460. The embolic filter 410 is coupled so that it is disposed around the catheter 402. This configuration advantageously allows the embolic filter 410 to engage the interior body lumen 992 (see FIG. 9D) wall, as the position of the catheter 402 within the body lumen 992 (see FIG. 9D) may be affected by the deployed deflector 460.

The combination of the deflector 460 and the embolic filter 410 can advantageously provide additional protection against potential complications resulting from thrombi in the blood stream. For example, if the embolic filter 410 (e.g., the distal end of the embolic filter 410) is distal to the deflector 460, the embolic filter 410 can serve as the primary means of embolic protection and the deflector 460 can serve as the secondary means of embolic protection. If some blood is able to flow around the embolic filter 410 rather than through it, the deflector 460 serves as a secondary (or back-up) protection device and prevents any debris not captured by the embolic filter 410 from entering the cerebral arteries and traveling to the brain. If the embolic filter 410 is proximal to the deflector 460, the deflector 460 can serve as the primary means of embolic protection and the embolic filter 410 can serve as the secondary means of embolic protection. The deflector 460 first deflects debris away from the carotid arteries, then the embolic filter 410 captures debris (e.g., including deflected debris) as blood flows through the descending aorta.

In some embodiments, the catheter 402 and outer sheath 412 can have lips, shoulders, nubs, and/or detents, for example similar to those shown in FIGS. 2A and 2B and described herein. For example, lips, shoulders, nubs, and/or detents can be positioned on the catheter 402 distal to the deflector 460, between the deflector 460 and embolic filter 410, and proximal to the embolic filter 410 to engage corresponding lips, shoulders, nubs, and/or detents on the outer sheath 412. The lips, shoulders, nubs, and/or detents can advantageously provide the user with information about the longitudinal position of the outer sheath 412 so that the user knows when neither, one, or both of the deflector 460 and embolic filter 410 are deployed. In some embodiments, either or both of the deflector 460 and embolic filter 410 can be movably coupled to the catheter 402 via an intermediate tube similar to that shown in FIGS. 3A-3D and described herein.

Figure 5A:
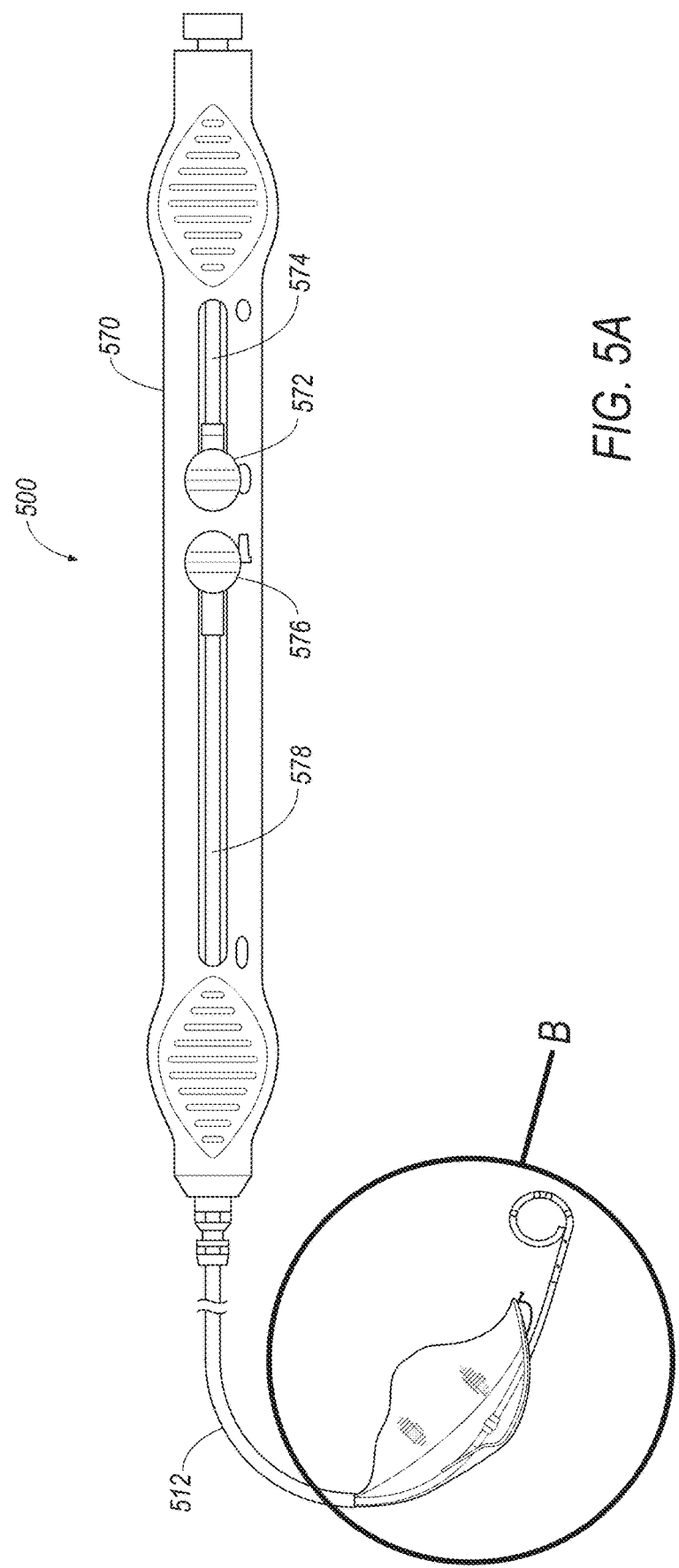
FIG. 5A illustrates an embodiment of an embolic protection device comprising a handle.
Figure 5B:
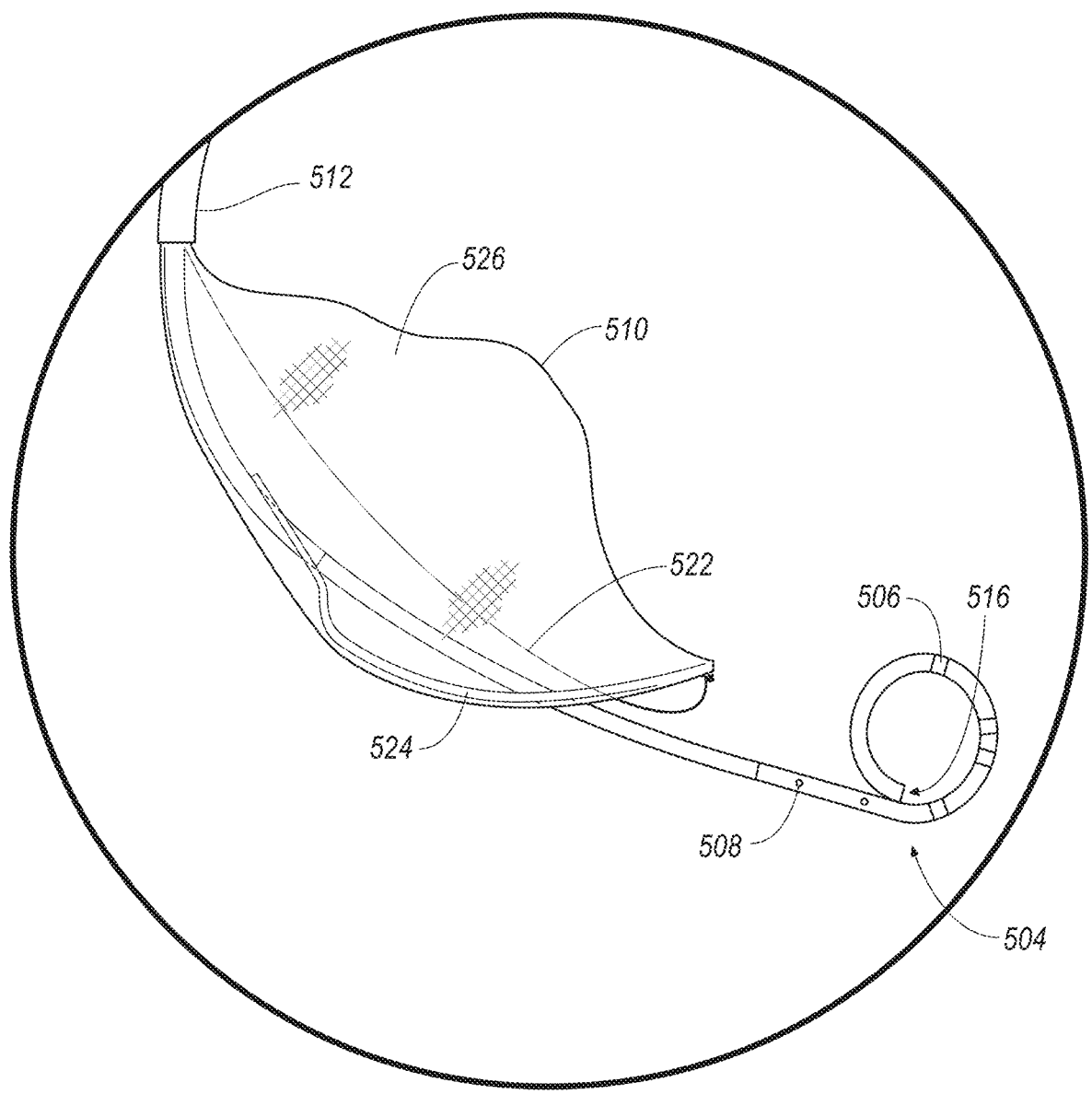
FIG. 5B illustrates a distal portion of the embolic protection device comprising the embolic filter and pigtail catheter.

An embodiment of an embolic protection device 500, similar to the embolic protection device 100 in FIGS. 1A-1E, is shown in FIGS. 5A and 5B. The embolic protection device 500 comprises a catheter 502, an embolic filter 510, a movable outer sheath 512, and a handle 570. In some embodiments, the catheter 502 is a pigtail-type catheter as shown in the close up view of FIG. 5B and described herein. The catheter 502 includes a distal portion 504 configured to assume a generally arcuate shape being at least a semi-circle. In some embodiments, the distal portion 504 of the catheter 502 includes one or more radiopaque markers 506. A side wall of the catheter 502 may optionally include one or more apertures 508 in the distal portion 504 that are configured to deliver one or more fluids (e.g., imaging dye, contrast agent, oxygenated blood, saline, any combination thereof, or the like) to a body lumen.

As illustrated in FIG. 5B, the embolic filter 510 comprises a frame 524 and a filter medium 526. In its deployed configuration, the embolic filter 510 opens towards a distal end 516 of the catheter 502. The device 500 further comprises a pull wire 522 that is coupled to the frame 524 and can be retracted to deflect or bend the frame 524 and change the orientation and shape of the embolic filter 510, in manner similar to that described above with reference to FIGS. 1B-1D.

Returning to FIG. 5A, the handle 570 has a wire-engagement mechanism 574 configured to advance or retract the pull wire 522 by movement of a first slider 572. The handle 570 also has a sheath-engagement mechanism 578 configured to advance or retract the deployment mechanism (e.g. outer sheath) 512 by movement of a second slider 576.

FIGS. 6A-6G illustrate embodiments of an embolic protection device 600. In these embodiments, the embolic protection device 600 comprises a catheter 602 (e.g., a pigtail catheter) having a proximal end 614, a distal end 616, and a lumen 618 extending from the proximal end 614 to the distal end 616 along a longitudinal axis of catheter 602. The lumen 618 may be configured to house a guidewire 1290 (see FIG. 12A) that is longitudinally movable through this lumen to coil or straighten the distal portion 604 of the catheter depending on whether the guidewire is retracted (to coil the distal portion) or extended (to straighten the distal portion). In some embodiments, the catheter 602 includes a distal portion 604 configured to assume a generally arcuate shape being at least a semi-circle. A side wall of the catheter 602 may optionally include one or more apertures 608 in the distal portion 604 that are configured to deliver one or more fluids (e.g., imaging dye, contrast agent, oxygenated blood, saline, any combination thereof, or the like) to a body lumen 1292 (see FIG. 12A). The apertures 608 (the plural intended to include embodiments in which the distal portion 604 includes one aperture 608) are in fluid communication with the lumen 618. In some embodiments, the distal portion 604 of the catheter 602 includes one or more radiopaque markers 606. In some embodiments, the radiopaque markers 606 are wrapped around the circumference of the distal portion 604 of the catheter 602 and can have the same or different widths. The embolic protection device 600 further comprises a self-expanding embolic filter 610 defined by a frame 624 and a filter medium 626, and a deployment mechanism 612 (e.g., a longitudinally retractable outer sheath or a longitudinally retractable ring). The embolic filter 610 is disposed around the catheter 602.

FIG. 6B illustrates the embolic filter 610 deployed in a self-expanded configuration by retraction of the deployment mechanism (e.g., outer sheath) 612. The embolic filter 610 includes a distal opening 640 that is defined by the frame 624, faces the distal end 616 of the catheter 602, and extends proximally from the distal opening 640 to a closed proximal end 642. The embolic protection device 600 further comprises a push wire 622 that is coupled to the frame 624. The push wire 622 can be advanced, in the distal direction, to deflect (or bend) and extend the frame 624; and, in turn, change the configuration of the embolic filter 610 between self-expanded, partially expanded, and fully expanded. In some embodiments, advancing the push wire 622 may cause the distal opening 640 of the embolic filter 610 to change orientation, shape, and/or size to engage at least a portion of the interior body lumen 1292 (see FIG. 12D) wall. FIG. 6B illustrates the push wire 622 in a retracted, i.e., un-advanced, state with the frame 624 extending in a distal, longitudinal direction, albeit angled back somewhat (e.g., less than about 45 degrees) in a lateral direction toward the proximal end 614. The catheter 602 may be partially surrounded towards its proximal end 614 by a support catheter 650 that terminates at a head 652, proximal to the distal portion 604 of the catheter 602. The support catheter 650 may be made of a thicker, stiffer material to add rigidity and provide a protective or supporting layer surrounding the catheter 602.

Figure 6D:
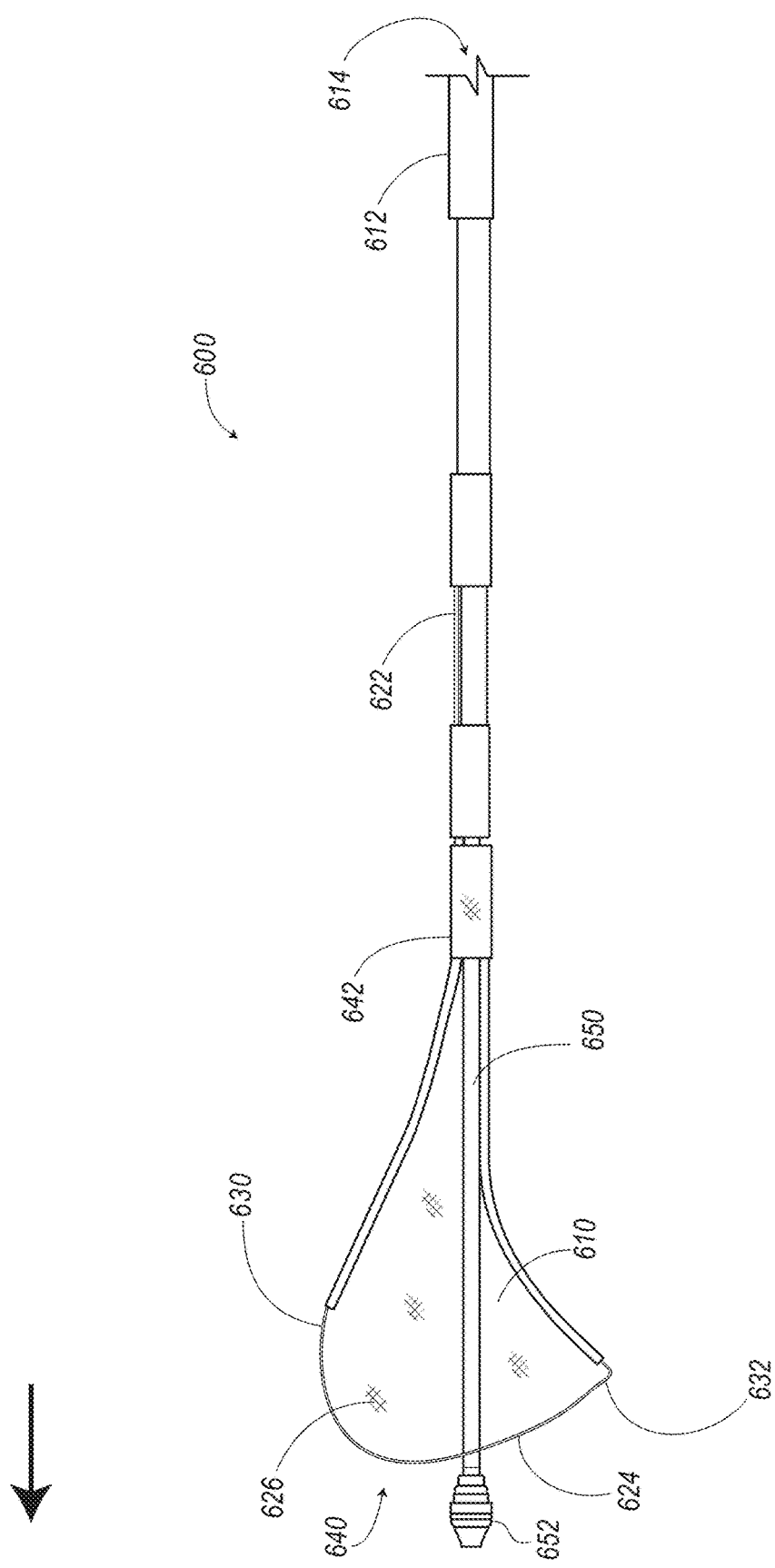
FIGS. 6D and 6E illustrate a side view and a front end view of the embolic filter in an partially expanded configuration, respectively, wherein the push wire coupled to the frame of the embolic filter is longitudinally advanced to a first distal position so that the frame assumes a deflected (i.e., bent) configuration.
Figure 6E:
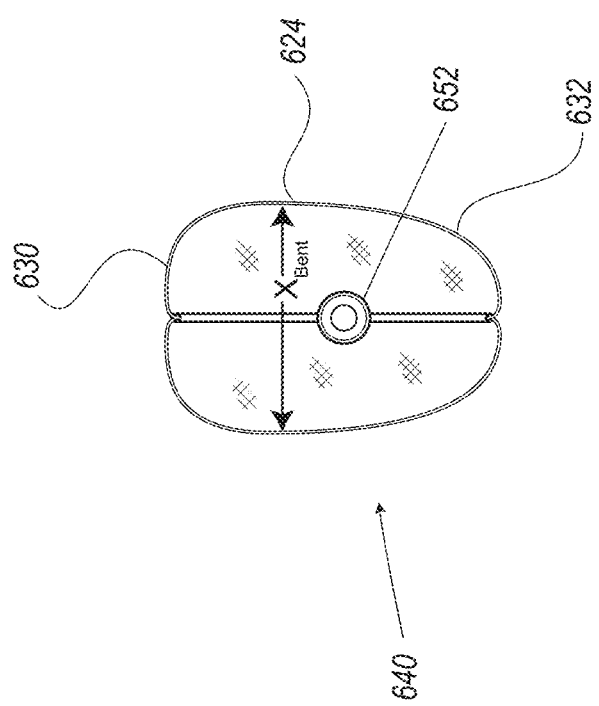
Figure 6F:
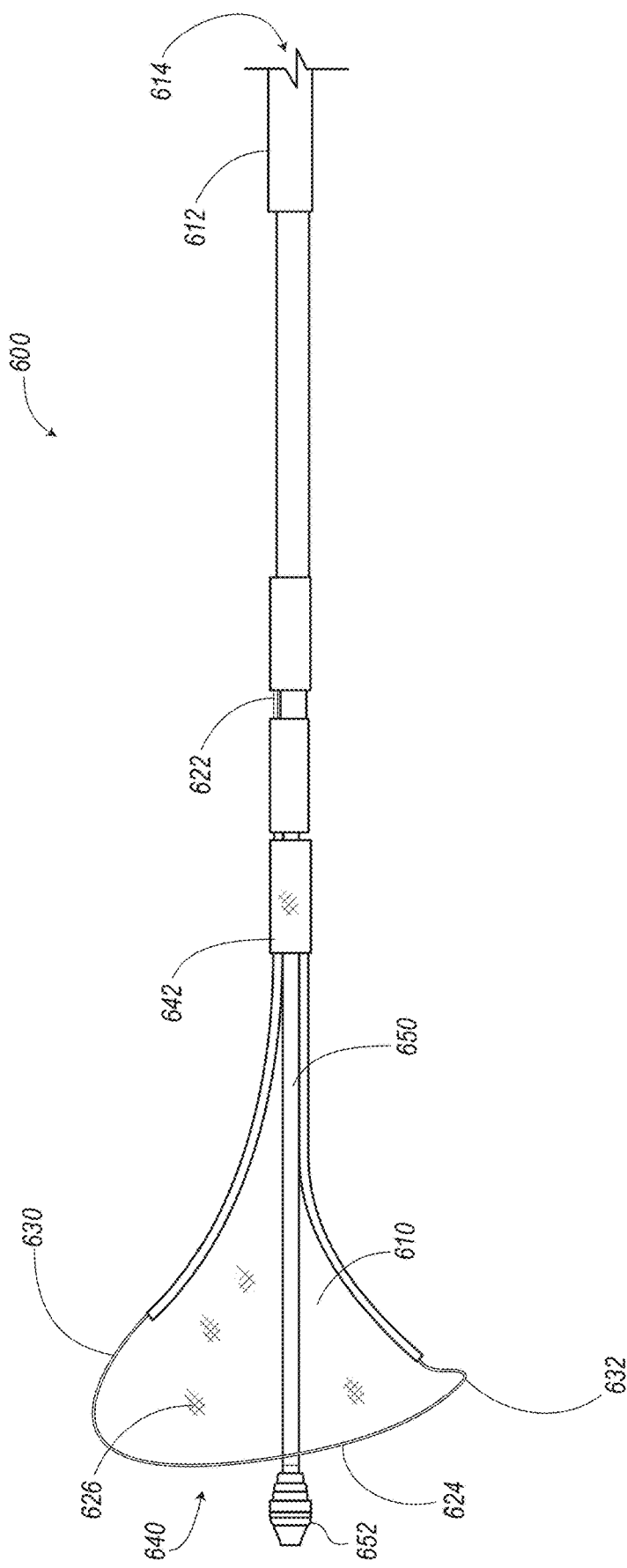
FIGS. 6F and 6G illustrate a side view and a front end view of the embolic filter in an fully expanded configuration, respectively, wherein the push wire coupled to the frame of the embolic filter is longitudinally advanced to a second distal position farther than the first distal position shown in FIG. 6C so that the frame assumes an extended configuration.
Figure 6G:
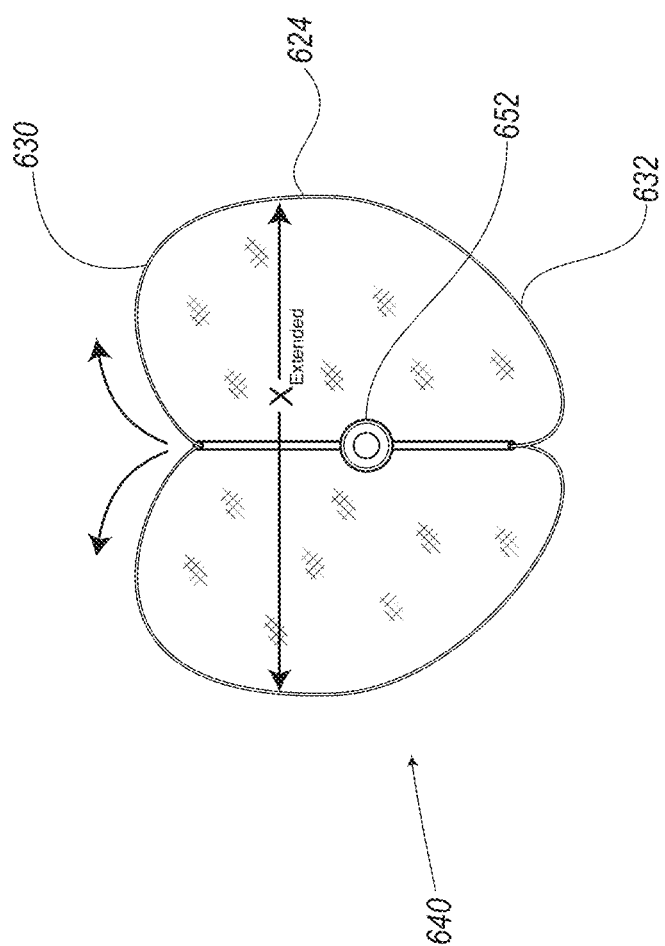

FIGS. 6C, 6E, and 6G show front-end views of the embolic filter 610, as viewed from the distal opening 640, in the self-expanded, partially expanded, and fully expanded configurations, respectively. The catheter 602 is removed from these views for clarity. The frame 624 comprises two sides (624a, 624b) that each extend generally in a first lateral direction away from the catheter 602/support catheter 650 and then loop back on opposite sides around the catheter 602/support catheter 650 and extend generally in the opposite lateral direction before converging and meeting to form a substantially elliptical (i.e., shaped like an ellipse), or alternatively, a substantially ovular (i.e. shaped like an oval), or circular shape. As shown, the embolic filter 610 is symmetrical about a plane (identified in the figure as a dotted line labeled "P"). For ease of discussion, the embolic filter 610 is referred to as having a left side and a right side. Elements on the left side of the embolic filter 610 are mirrored by elements on the right side of the embolic filter 610.

FIGS. 6D and 6E illustrate the embolic filter 610 in the partially expanded configuration with the frame 624 deflected (i.e., bent) by advancement of the push wire 622 in the distal direction. The frame 624 comprises a movable portion 630 and a fixed portion 632. The movable portion 630 of the frame 624 can move, longitudinally, with respect to the catheter 602/support catheter 650. With respect to the catheter 602/support catheter 650, the movable portion 630 can move, longitudinally, while the fixed portion 632 cannot. The frame 624 is coupled to the push wire 622 at the movable portion 630. In a convenient embodiment, the push wire 622 and movable portion 630 are joined by a crimp. In other embodiments, the push wire 622 and movable portion 630 are joined by a weld, adhesive, or threads. The frame 624 is attached to the support catheter 650 (or alternatively, directly to the catheter 602) by the fixed portion 632. The fixed portion 632 of the frame 624 may be attached to the catheter 602/support catheter 650 by a weld, an adhesive, or the like.

Starting at the fixed portion 632, the frame 624 extends in a distal, longitudinal direction and then bends at an angle with respect to the longitudinal axis of the catheter 602/support catheter 650. When the push wire 622 is in its retracted state, the frame 624 bends at an acute angle and extends in a proximal, longitudinal direction such that the frame 624 folds onto itself (see FIG. 6B). Advantageously, in this configuration, the embolic filter 610 may more effectively retain embolic debris captured during a procedure. The curvature of the frame 624 adjacent the movable portion 630 may aid in collapsing the frame 624 in order to advance the outer sheath 612 over the embolic filter 610.

FIG. 6E shows the front-end view of the embolic filter 610, as viewed from the distal opening 640, when the push wire 622 is advanced and the embolic filter 610 assumes a partially expanded configuration. The advancing push wire 622 urges the movable portion 630 forward relative to the catheter 602/support catheter 650. (Shown in FIG. 6D as an arrow pointing away from the support catheter 650.) This in turn deflects or bends the frame 624 longitudinally in the distal direction and laterally outward. In a deflected configuration (i.e., when the push wire 622 is advanced), the distal opening 640 of the embolic filter 610 may be substantially perpendicular to the longitudinal axis of the catheter 602/support catheter 650 and may span laterally across the body lumen 1292 (see FIG. 12D), substantially perpendicular to the longitudinal axis of the body lumen 1292. In the deflected configuration, the width, $X_{bent}$, across the distal opening 640 is increased compared to the corresponding dimension in the non-deflected configuration. By increasing the width, $X_{bent}$, in the bent configuration, the frame 624 defining the distal opening 640 engages the body lumen 1292.

FIGS. 6F and 6G illustrate the embolic filter 610 in the fully expanded configuration with the frame 624 extended by the further advancement of the push wire 622 in the distal direction. Moving the push wire 622 further, distally, urges the movable portion 630 sideways relative to the catheter 602/support catheter 650. This in turn extends the frame 624 radially outward, away from the catheter 602/support catheter 650. (Shown in FIG. 6G as a left directional arrow and right directional arrow pointing away from the support catheter 650.) In some embodiments, in addition to extending the frame 624 in the radial direction, the advancing push wire 622 moves the movable portion 630 forward relative to the catheter 602/support catheter 650; which, in turn, bends the frame 624, further, in the longitudinal direction. In one embodiment, the movable portion 630 is formed with a curve or bend to aid in extending the frame 624 in the radial direction.

In an extended configuration, the width, $X_{extended}$, across the distal opening 640 is increased compared to the corresponding dimension ($X_{bent}$) in the partially expanded configuration of the embolic filter 610. By increasing the width, $X_{extended}$, in the extended configuration, the frame 624 defining the distal opening 640 engages the body lumen 1292. The increase in the width across the distal opening 640 between the partially expanded configuration ($X_{bent}$) and the fully expanded configuration ($X_{extended}$) of the embolic filter 610 (and intermediate configurations in between) may represent a range of filter sizes or diameters, e.g., 25 millimeters (mm) to 40 mm. The range of filter sizes accommodates variations in patient vasculature. Advantageously, instead of a one-size-fits-all device or multiple devices of different sizes, certain embodiments of the embolic protection device 600 provide a single device that can be tailored to a particular patient and/or a particular surgical procedure. For example, a surgeon can expand the embolic filter 610 to a first size and then adjust the embolic filter 610 to a second size to achieve a better fit within a patient's vasculature.

In some embodiments, the distal opening 640 of the embolic filter 610 has a diameter of from about 2 centimeters (cm) to about 6 cm (e.g., from about 2.5 cm to about 4 cm or to about 4.5 cm). The embolic filter 610 can comprise any suitable size or diameter to accommodate anatomic variability in patients' body lumens 1292 (see FIG. 12A).

Figure 7A:
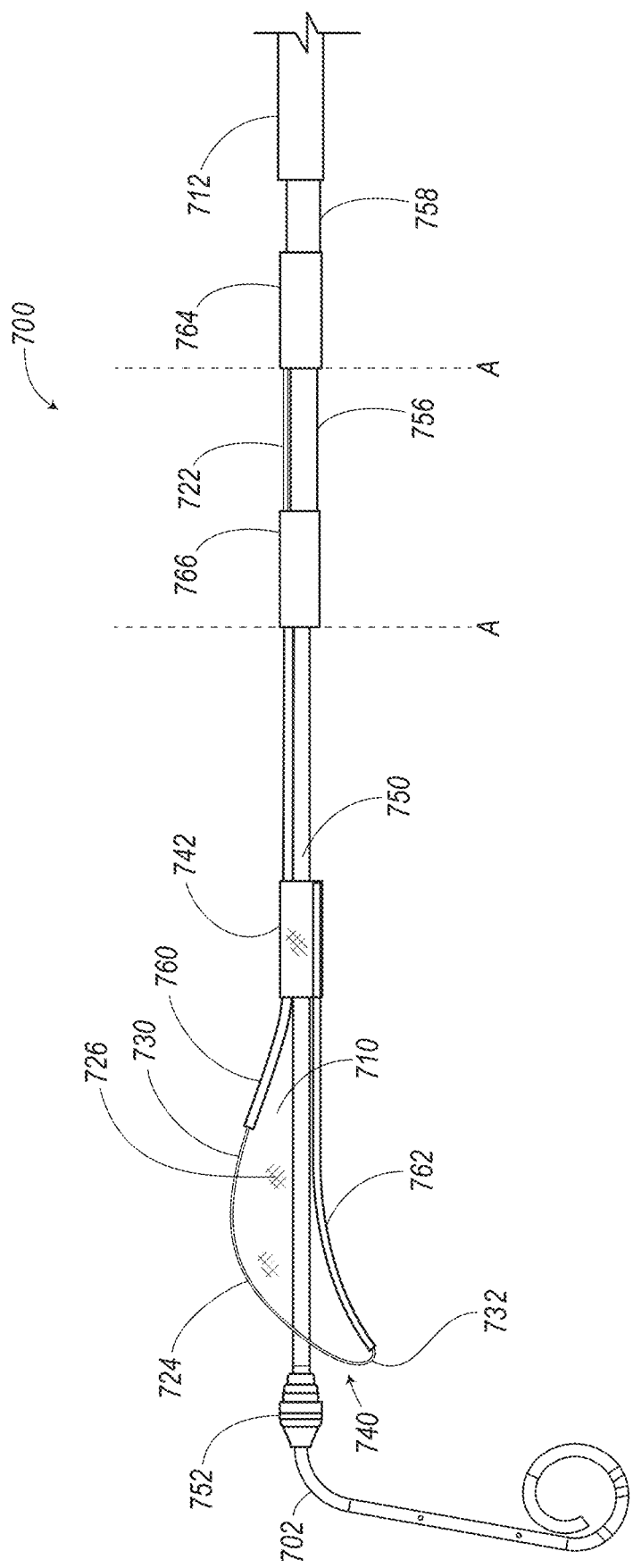
FIGS. 7A-7C illustrate partial side views of an embodiment of an embolic protection device of the present invention having an actuating mechanism for operating an embolic filter.
Figure 7B:
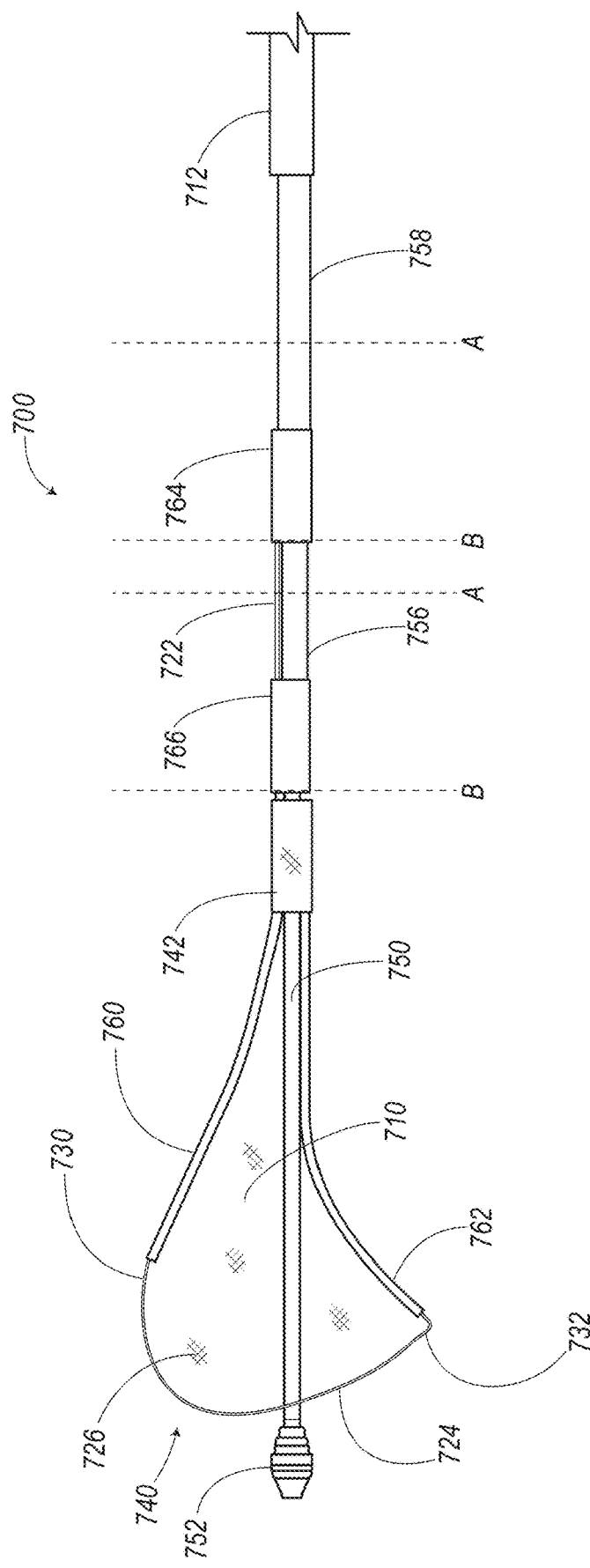
Figure 7C:
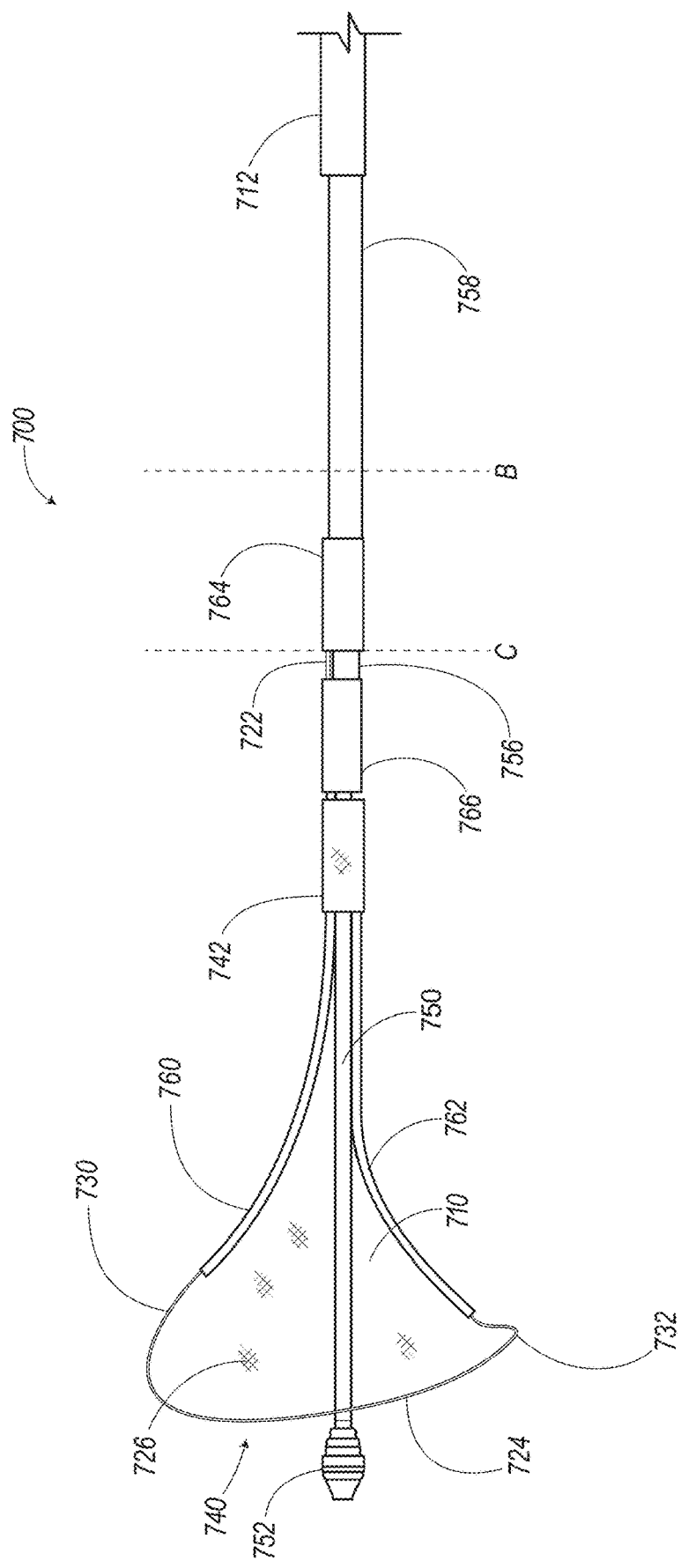

FIGS. 7A-7C illustrate another embodiment of an embolic protection device 700 comprising a catheter 702, an embolic filter 710, a movable outer sheath 712, and an actuating mechanism for operating the embolic filter 710. A portion of the catheter 702 is slidably received and supported by a fixed inner catheter 750 that terminates at a head 752. The fixed inner catheter 750 may be made of a thicker, stiffer material to add rigidity and provide a protective or supporting layer surrounding the catheter 702. The embolic filter 710 is disposed around the fixed inner catheter 750 and is configured to self-expand to a radially expanded configuration, as shown in FIG. 7A, when not confined or restrained by the outer sheath 712.

The embolic filter 710 includes a frame 724 and a filter medium 726. The frame 724 defines a distal opening 740 of the embolic filter 710 and includes a movable portion 730 for controlling the size or diameter of the distal opening 740.

The embolic filter 710 extends proximally from the distal opening 740 to a closed proximal end 742. The frame 724 further includes a fixed portion 732 for attaching the frame 724 to the fixed inner catheter 750 at a location adjacent to the closed proximal end 742 of the embolic filter 710. In some embodiments, the embolic protection device 700 is similar to the embolic protection device 600 of FIGS. 6A-6G with the addition of the actuating mechanism.

The actuating mechanism comprises an inner catheter 756 and an outer catheter 758. The inner catheter 756 slides over the fixed inner catheter 750. The outer catheter 758 slides over the inner catheter 756. The movement of the inner catheter 756 and outer catheter 758 relative to the fixed inner catheter 750 controls the size or diameter of the embolic filter 710, as will be described in greater detail below.

The embolic protection device 700 further includes a push wire 722 coupled to a distal portion 764 of the outer catheter 758. The push wire 722 is longitudinally movable between a fully retracted state, a partially advanced (or partially retracted) state, and a fully advanced state by the outer catheter 758. The push wire 722 is further coupled to the movable portion 730 of the frame 724. Moving the outer catheter 758, relative to the fixed inner catheter 750, translates into moving the push wire 722 between the fully retracted, partially advanced, and fully advanced states. This in turn urges the movable portion 730, causing the frame 724 to deflect (or bend) or extend.

In various embodiments of the embolic protection device 700, the foregoing device components may be coupled to each other, as described above, by any number of means and techniques. For example, in a convenient embodiment, sleeves made from polyether block amide (PEBAX®) or other similar biocompatible material attach the push wire 722 to the distal portion 764 of the outer catheter 758, attach the top guide 760 to the distal portion 766 of the inner catheter 756, and attach the bottom guide 762 to the fixed inner catheter 750. Additionally or alternatively, the device components may be joined together with a biocompatible adhesive(s).

The actuating mechanism further comprises a top guide 760 and a bottom guide 762 for directing the deflection and extension of the frame 724 so that the distal opening 740 of the embolic filter 710 faces towards a distal end (or working end) of the device 220 as it expands. In some embodiments, the top guide 760 and the bottom guide 762 keep the movable portion 730 and the fixed portion 732 of the frame 724 straight, respectively. The top guide 760 and the bottom guide 762 are arranged at opposite points around the fixed inner catheter 750 with portions disposed along the fixed inner catheter 750. The top guide 760 is coupled at one end to a distal portion 766 of the inner catheter 756. A portion of the top guide 760, distal to the distal portion 766, is in slidable engagement with the fixed inner catheter 750 at or otherwise adjacent to the closed proximal end 742 of the embolic filter 710. For example, a portion of the top guide 760 slides under the filter medium 726 along the fixed inner catheter 750 and passes through the closed proximal end 742 of the embolic filter 710. The bottom guide 762 is fixedly attached to the fixed inner catheter 750 at or otherwise adjacent to the closed proximal end 742 of the embolic filter 710.

At the distal opening 740 of the embolic filter 710, the top guide 760 and the bottom guide 762 are movable away from the fixed inner catheter 750. The top guide 760 slidably receives the movable portion 730 of the frame 724 and the bottom guide 762 receives the fixed portion 732. The arrangement causes the top guide 760 and bottom guide 762 to flare or flex outward away from the fixed inner catheter 750 (as one moves from the closed proximal end 742 of the embolic filter 710 to the distal opening 740), thereby, giving the embolic filter 710 a general funnel-like appearance. The top guide 760 and the bottom guide 762 may also support the filter medium 726, in the longitudinal and lateral directions, between the distal opening 740 and the closed proximal end 742 of the embolic filter 710. In a convenient embodiment, the top guide 760 and the bottom guide 762 are hypotubes made from stainless steel, polyetheretherketone (PEEK), or other biocompatible material.

FIG. 7A further illustrates the outer sheath 712 fully retracted over the embolic filter 710 and the embolic filter 710 exposed. The inner catheter 756 and outer catheter 758 are in their initial positions (labeled "A" in the figure) relative to the fixed inner catheter 750. With the embolic filter 710 unsheathed, the movable portion 730 and the fixed portion 732 of the frame 724, with the top guide 760 and bottom guide 762, flex outwardly away from the fixed inner catheter 750. This causes the distal opening 740 of the embolic filter 710 to lie at an angle with respect to the fixed inner catheter 750. For example, the frame 724 and the fixed inner catheter 750 are at an angle of 45 degrees or less. At this stage in deployment, the embolic filter 710 is in a self-expanded configuration with the frame 724 unbent.

FIG. 7B illustrates the distal opening 740 partial expanded to a first size or diameter. The inner catheter 756 and outer catheter 758 are advanced in unison, distally, over the fixed inner catheter 750. The inner catheter 756 and outer catheter 758 are moved from their initial positions (labeled "A" in the figure) to their intermediate positions (labeled "B" in the figure), relative to the fixed inner catheter 750. The concerted movement of the inner catheter 756 and the outer catheter 758 advances the push wire 722 and the top guide 760 together; and, in turn, urges the movable portion 730 of the frame 724, longitudinally, in the distal direction (forward direction). This rotates the distal opening 740 of the embolic filter 710 into an orientation substantially perpendicular to the longitudinal axis of the fixed inner catheter 750 and expands the distal opening 740 to the first size (e.g., a diameter of about 25 mm).

FIG. 7C illustrates the distal opening 740 fully expanded to a second size larger than the first size. In FIG. 7E, the outer catheter 758 is distally advanced over the inner catheter 756 and the fixed inner catheter 750. Without the inner catheter 756 moving, the outer catheter 758 moves from its intermediate position (labeled "B" in the figure) to its final position (labeled "C" in the figure), relative to the fixed inner catheter 750. The continued distal movement of the outer catheter 758 moves the push wire 722 without moving the top guide 760. A length of the movable portion 730 of the frame 724 is radially played out from the top guide 760 (i.e., out of the plane of the page), extending the frame 724 and further expanding the distal opening 740 of the embolic filter 710 to the second size (e.g., a diameter of about 40 mm).

Figure 8A:
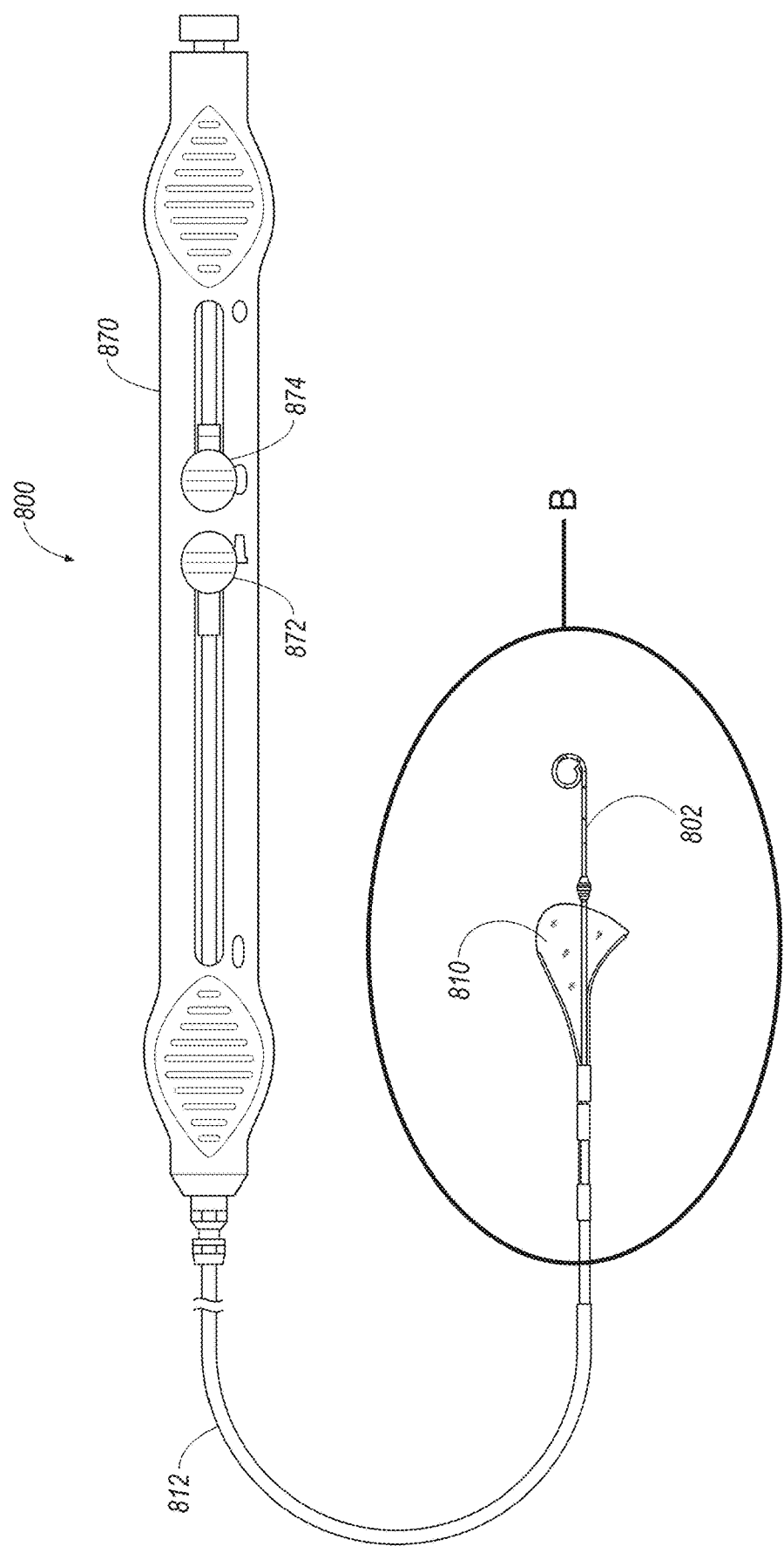
FIGS. 8A and 8B illustrate an embodiment of an embolic protection device of the present invention having a handle for manually operating an embolic filter.
Figure 8B:
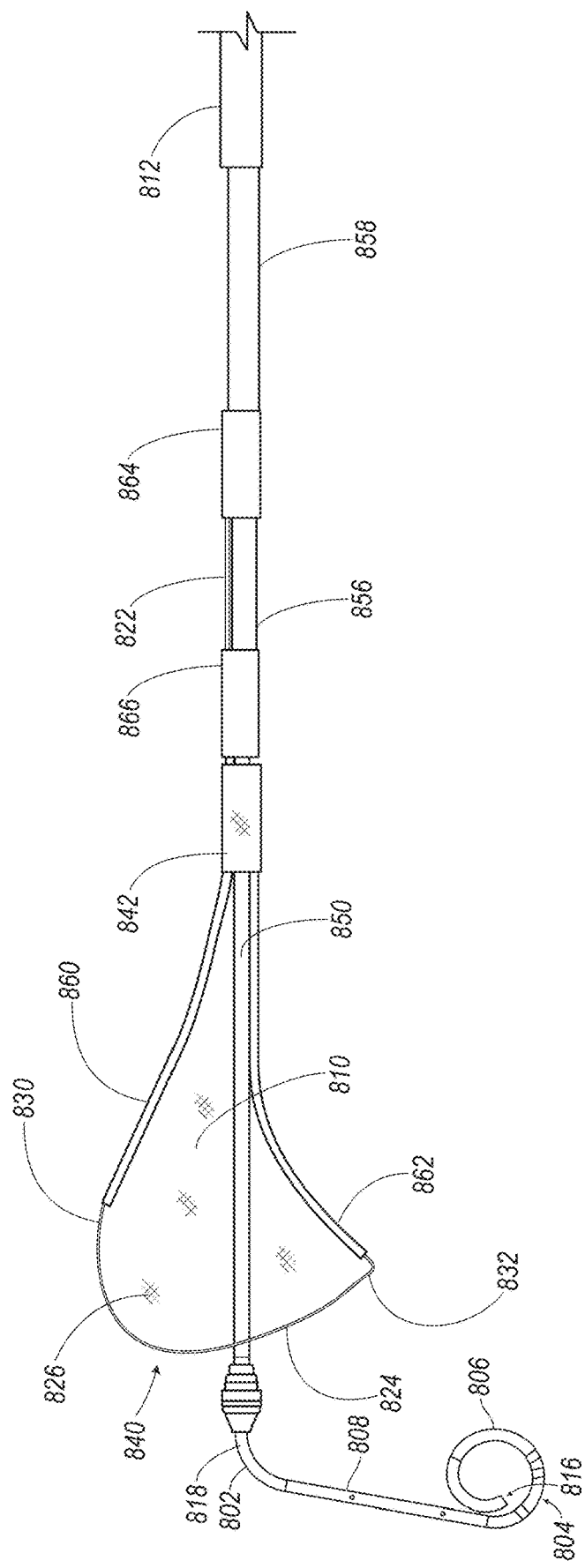

FIGS. 8A-8F illustrate embodiments of an embolic protection device 800 comprising a catheter 802, an embolic filter 810, a movable outer sheath 812, and a handle 870 for manually operating the embolic filter 810. In FIG. 8B, the embolic protection device 800 further comprises a push wire 822, a filter frame 824, a filter media 826, a movable portion 830, a fixed portion 832, a fixed inner catheter 850, an inner catheter 856, an outer catheter 858, a top guide 860, and a bottom guide 862 arranged in a configuration similar to the configuration described above with reference to FIGS. 7A-7C. For example, the push wire 822 is coupled to a distal portion 864 of the outer catheter 858, and the top guide 860 is coupled at one end to a distal portion 866 of the inner catheter 856. In some embodiments, the embolic protection device 800 is similar to the embolic protection device 700 of FIGS. 7A-7C with the addition of the handle 870.

FIG. 8A illustrates the handle 870 having a first slider 872 operable for manually retracting the outer sheath 812 over the catheter 802 and the embolic filter 810 to deploy the embolic filter 810 in a self-expanded configuration. The first slider 872 is further used to manually advance the outer sheath 812 over the catheter 802 and the embolic filter 810, and collapse/recover the embolic filter 810. The handle 870 further includes a second slider 874 operable for manually increasing and decreasing the size or diameter of a distal opening 840 of the embolic filter 810. (The embolic filter 810 extends proximally from the distal opening 840 to a closed proximal end 842.)

In some embodiments, the catheter 802 is a pigtail-type catheter as shown in FIG. 8B and described herein. The catheter 802 includes a distal portion 804 configured to assume a generally arcuate shape being at least a semi-circle. In some embodiments, the distal portion 804 of the catheter 802 includes one or more radiopaque markers 806. A side wall of the catheter 802 may optionally include one or more apertures 808 in the distal portion 804 that are configured to deliver one or more fluids (e.g., imaging dye, contrast agent, oxygenated blood, saline, any combination thereof, or the like) to a body lumen.

The catheter 802 has a proximal end, a distal end 816, and a lumen 818 extending between the proximal end and the distal end 816. The lumen 818 may be configured to house a guidewire 1290 (see FIGS. 12A and 12B) that is longitudinally moveable through this lumen to coil or straighten the distal portion 804 of the catheter 802 depending on whether the guidewire is retracted (to coil the distal portion) or extended (to straighten the distal portion). The apertures 808 and the lumen 818 may in fluid communication with each other in order to deliver one or more fluids to a body lumen as described above.

As shown in the FIG. 8B, an example of the catheter 802 is partially surrounded towards its proximal end by the fixed inner catheter 850 that terminates at a head 852, proximal to the distal portion 804 of the catheter 802. The fixed inner catheter 850 may be made of a thicker, stiffer material to add rigidity and provide a protective or supporting layer surrounding the catheter 802.

Figure 8C:
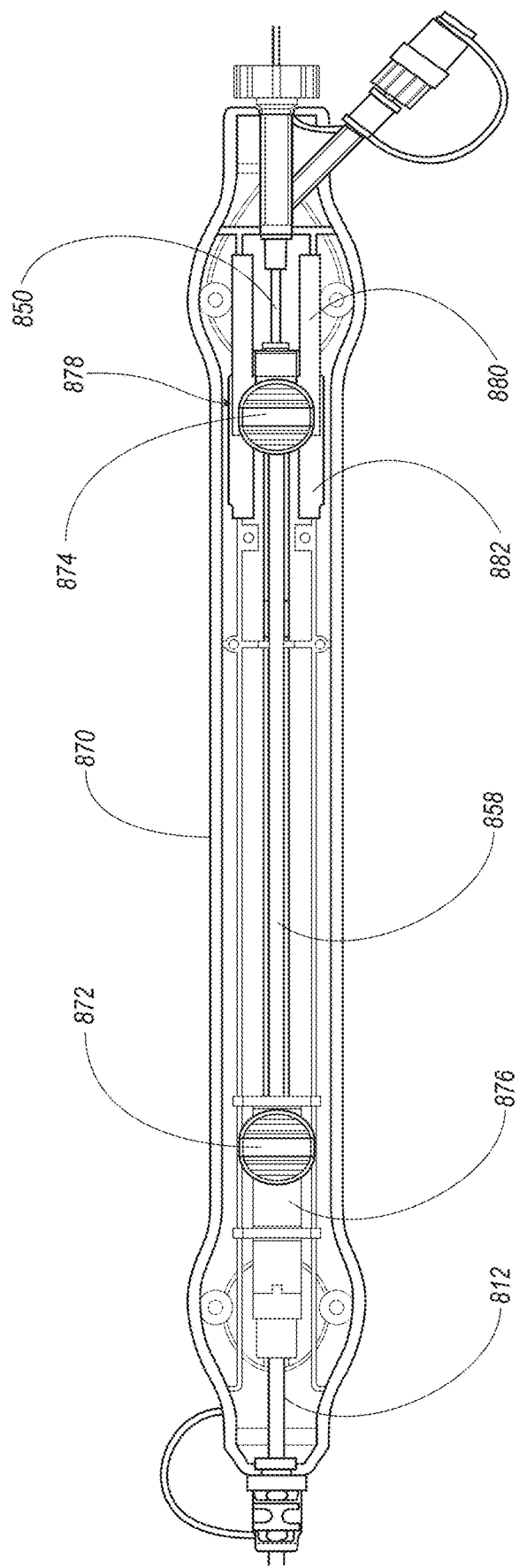
FIGS. 8C-8F illustrate an example of the handle.

FIG. 8C illustrates an example of the handle 870 (with the handle cover removed for clarity) including a sheath-engagement mechanism 876 configured to advance or retract the outer sheath 812 by movement of the first slider 872. The outer sheath 812 is joined to the sheath-engagement mechanism 876. Any number of suitable means, (e.g., fastener and/or adhesive) or techniques (e.g., sonic welding, solvent welding, and overmolding) can be used to join the outer sheath 812 and sheath-engagement mechanism 876.

Figure 8D:
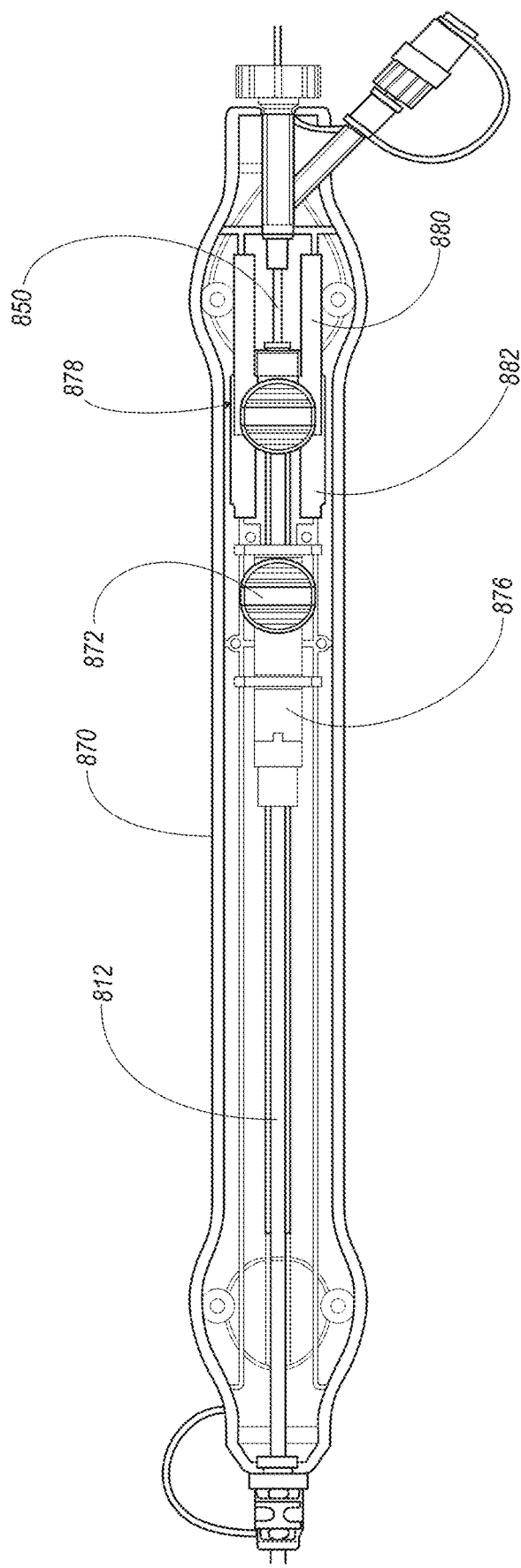

The sheath-engagement mechanism 876 is movable within the handle 870 between a distal, initial position (shown in FIG. 8C) and a proximal, final position (shown in FIG. 8D). The initial position of the sheath-engagement mechanism 876 corresponds with the outer sheath 812 circumferentially disposed around at least a portion of embolic filter 810 and the embolic filter 810 housed in the collapsed configuration. The final position of the sheath-engagement mechanism 876 corresponds with the outer sheath 812 longitudinally retracted over the embolic filter 810 and the embolic filter 810 deployed in the self-expanded configuration.

The sheath-engagement mechanism 876 is selectively operable by the first slider 872. For example, an operator presses down on the first slider 872 with their thumb to unlock the sheath-engagement mechanism 876 from the handle 870 in order to move the sheath-engagement mechanism 876 from the initial position (shown in FIG. 8C) to the final position (shown in FIG. 8D). The operator moves the first slider 872, proximally, using their thumb to retract the outer sheath 812 and expose the embolic filter 810. To collapse/recover the embolic filter 810, the operator moves the first slider 872, distally, and advances the outer sheath 812 over the embolic filter 810.

The example of the handle 870 shown in FIG. 8C further includes an engagement mechanism 878 configured to change the size or diameter of the distal opening 840 of the embolic filter 810 by movement of the second slider 874. The engagement mechanism 878 comprises a top pull 880 and a bottom pull 882. The top pull 880 is coupled to a proximal portion of the outer catheter 858 and the bottom pull 882 is coupled to a proximal portion of the inner catheter 856 (shown in FIG. 8F).

Figure 8E:
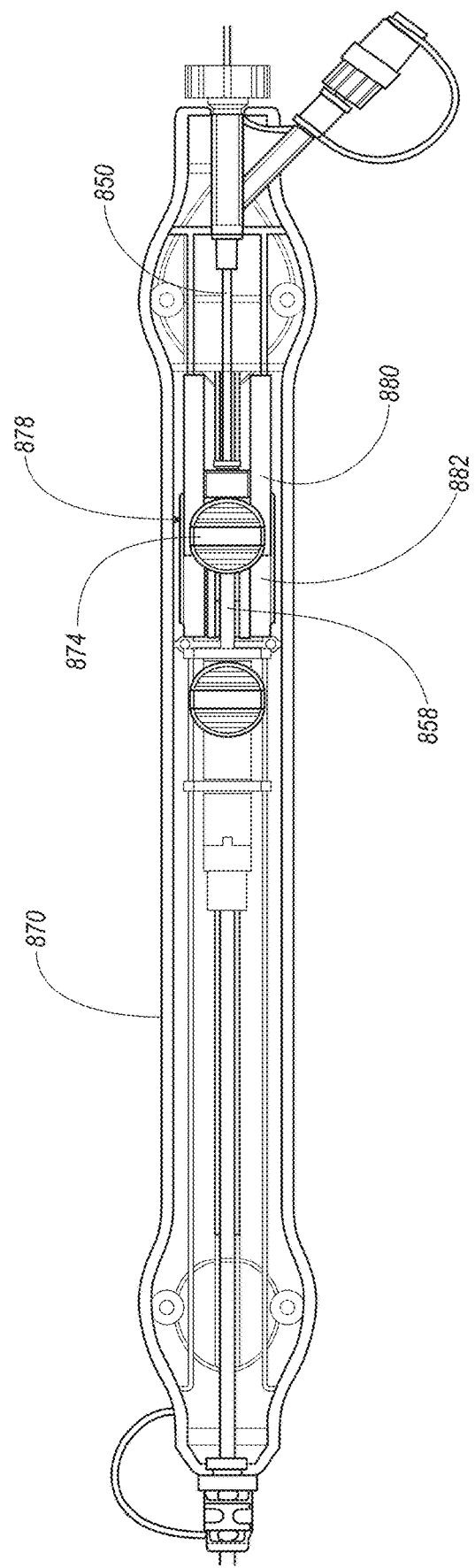
Figure 8F:
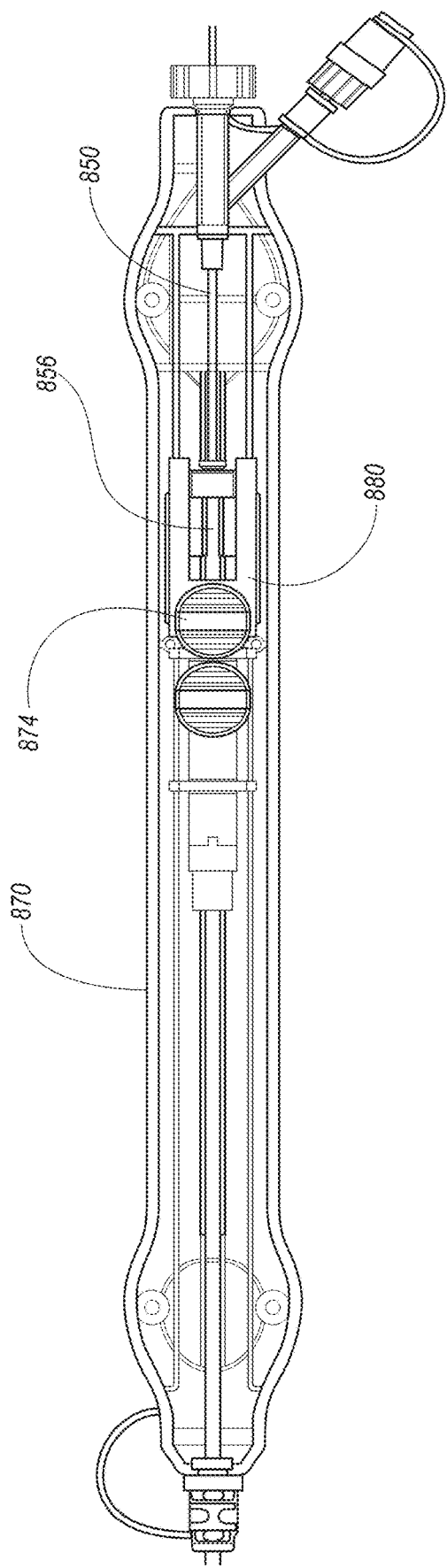

The engagement mechanism 878 is movable within the handle 870 between an initial (proximal) position (shown in FIGS. 8C and 8D), an intermediate position (shown in FIG. 8E), and a final (distal) position (shown in FIG. 8F). The initial position of the engagement mechanism 878 corresponds with the embolic filter 810 in the self-expanded configuration with the filter frame 824 undeflected (or unbent). The intermediate position of the engagement mechanism 878 corresponds with the embolic filter 810 in a partially expanded configuration with the filter frame 824 deflected (or bent) in the longitudinal direction. The final position of the engagement mechanism 878 corresponds with the embolic filter 810 in a fully expanded configuration with the filter frame 824 extended in the radial direction.

The engagement mechanism 878 is selectively operable by the second slider 874. For example, with the engagement mechanism 878 at the initial position (shown in FIG. 8D), a user presses the second slider 874 down. The applied force causes a projection (not shown) extending from the second slider 874 to move downward through a hole (not shown) in the top pull 880 and into a recess (not shown) in the bottom pull 882.

In FIG. 8E, with combined reference to FIG. 8B, with the second slider 874 depressed and engaged with both the top pull 880 and the bottom pull 882, the operator moves the second slider 874, distally, using their thumb to advance the outer catheter 858 and the inner catheter (hidden from view) together. The concerted movement of the outer catheter 858 and the inner catheter moves the push wire 822 and the top guide 860 together (i.e., moved in unison). This in turn, advances the movable portion 830, longitudinally, in the distal direction (forward direction), and expands the distal opening 840 of the embolic filter 810.

The distal opening 840 continues to expand with the distal movement of the second slider 874 until the engagement mechanism 878 reaches the intermediate position shown in FIG. 8E. At the intermediate position, the distal opening 840 is at a first size (e.g., a diameter of about 25 mm) and the second slider 874 partially disengages from the engagement mechanism 878. For example, a spring and ball plunger (not shown), located within the handle 870, lifts the projection out of the recess in the bottom pull 882. The second slider 874 disengages from the bottom pull 882 but remains engaged with the top pull 880. It may be convenient to refer to the engagement between the top pull 880 and the bottom pull 882 as temporary.

In FIG. 8F, with combined reference to FIG. 8B, the operator continues to move the second slider 874, distally, to advance the outer catheter 858 farther in the distal direction. With the bottom pull 882 disengaged, the inner catheter 856 and the top guide 860 are fixed in position, while the push wire 822 advances farther in the distal direction. As a result, a length of the movable portion 830 is radially played out from the top guide 860 (i.e., out of the plane of the page) and further expands the distal opening 840 of the embolic filter 810 to a next size (e.g., a diameter of about 30 mm). The distal opening 840 expands to its maximum size (e.g., a diameter of about 40 mm) when the engagement mechanism 878 is at the final position as shown in FIG. 8F. To recover the embolic filter 810, the process described above with reference to FIGS. 8C-8F is carried out in reverse.

In some embodiments, a wire of an embolic protection device as described herein, e.g., the pull wire 122 of the embolic protection device 100 of FIG. 1B or the push wire 622 of the embolic protection device 600 of FIG. 6B, comprises a metal material, for example, stainless steel. Alternatively, the wire may comprise a plastic material or other suitable material. In some embodiments, the wire is stainless steel coated in polytetrafluoroethylene (PTFE). In the case of the wire being a pull wire, similar to the pull wire 122 of FIG. 1B, the pull wire is flexible but may have sufficient rigidity to deflect (or bend) a frame of an embolic filter in a proximal direction when the pull wire is retracted in a manner similar to that described above with reference to FIGS. 1C and 1D. In the case of the wire being a push wire, similar to the push wire 622 of FIG. 6B, the push wire is flexible but may have sufficient rigidity to deflect/bend a frame of an embolic filter in a distal direction when the pull wire is advanced; and to extend the frame in a radial direction when the pull wire is father advanced in a manner similar to that described above with reference to FIGS. 6D-6F.

In some embodiments, a filter medium (e.g., the filter medium 126 of FIG. 1A or the filter medium 626 of FIG. 6B) comprises a braided mesh, for example braided nitinol mesh. In some embodiments, the filter medium comprises a porous membrane, for example a semi-permeable polyurethane membrane. In other embodiments, the filter medium has a pore size of from about 100 microns to about 150 microns (e.g., about 125 microns).

In some embodiments, an embolic filter (e.g., the embolic filter 110 of FIG. 1B or the embolic filter 610 of FIG. 6B) comprises an anti-thrombogenic coating (e.g., a heparin coating or other coating comprising a thrombin or platelet inhibitor) to advantageously reduce thrombogenicity.

The embolic filter is configured to self-expand to a radially expanded configuration illustrated in, for example FIGS. 1B and 1C, and FIGS. 6B and 6C, when not confined or restrained by an deployment device, such as the outer sheath 112 of FIG. 1A or the outer sheath 612 of FIG. 6A.

In some embodiments wherein the deployment mechanism comprises an outer sheath (e.g., the movable outer sheath 112 of FIG. 1A or the movable outer sheath 612 of FIG. 6A), the outer sheath is configured to be circumferentially disposed around at least a portion of a catheter and a embolic filter (e.g., the catheter 102 and the embolic filter 110 of FIG. 1A; or the catheter 602 and the embolic filter 610 of FIG. 6A). The outer sheath is configured to contain or house the embolic filter in a collapsed configuration. The outer sheath is longitudinally movable with respect to the catheter, and can be longitudinally retracted (i.e., moved longitudinally in a proximal direction) to deploy the embolic filter and longitudinally advanced (i.e., moved longitudinally in a distal direction) to recapture the embolic filter and any embolic material collected by the embolic filter. The embolic filter is configured to self-expand upon longitudinal retraction of the outer sheath.

In some embodiments, an embolic filter of an embolic protection device as described herein (e.g., the embolic filter 110 of FIG. 1A and the embolic filter 610 of FIG. 6A) is configured to at least partially collapse upon longitudinal extension of an outer sheath (e.g., the outer sheath 112 of FIG. 1A and the outer sheath 612 of FIG. 6A). In these embodiments, a distal opening of the embolic filter (e.g., the distal opening 140 of FIG. 1B and the distal opening 640 of FIG. 6B) assumes a substantially closed configuration thereby sequestering or substantially sequestering the filtered material.

In some embodiments, a catheter of an embolic protection device as described herein (e.g., the catheter 102 of FIG. 1A and the catheter 602 of FIG. 6A) may comprise a flexible material so as to be maneuverable within a body lumen (e.g., the body lumen 992 of FIG. 9A and the body lumen 1292 of FIG. 12A) as further described herein. For example, in some embodiments, the catheter comprises a metal or metal alloy. In other embodiments, the catheter comprises a polymer (e.g., polyurethane, silicone, latex, polytetrafluoroethylene (PTFE), a plastic material, any combination thereof, or the like). In some embodiments, the catheter comprises a metal-reinforced plastic (e.g., including nitinol, stainless steel, and the like). Other materials are also possible. In some embodiments, the catheter is substantially free of latex (natural or synthetic), which may cause allergic reactions in some patients. In some embodiments, the catheter comprises braid-reinforced tubing to advantageously increase the strength of the catheter. In some embodiments, the catheter comprises a braided catheter shaft including a layer of braided wire between two layers of catheter tubing, which may increase the strength of the catheter. In some embodiments, the catheter does not include a braided layer, which may increase the flexibility of the catheter. In some embodiments, the catheter comprises a lubricious coating, for example a coating having a low friction coefficient, to advantageously allow for smoother navigation through tortuous vasculature. In some embodiments, the catheter coating has anti-thrombotic properties to advantageously inhibit thrombus formation. In some embodiments, the catheter has a size (i.e., outside diameter) between about 3 French and about 5 French (between about 2 mm and about 3 mm). Other sizes are also possible, for example depending on the size of the target body lumen of a particular patient. In some embodiments, the catheter has a length between about 65 centimeters (cm) and about 135 cm. Other lengths are also possible, for example to allow for insertion of the catheter in the femoral, radial, brachial, or subclavian artery. The catheter can be manufactured, for example, by extrusion, injection molding, or another suitable process.

In some embodiments, an embolic protection device as described herein may include one or more radiopaque marker bands located at a distal portion of a catheter. For example, the embolic protection device 100 of FIGS. 1A and 1B with the radiopaque markers 106 located at the distal portion 104 of the catheter 102. As another example, the embolic protection device 600 of FIGS. 6A and 6B with the radiopaque markers 606 located at the distal portion 604 of the catheter 602. When the distal portion assumes a generally arcuate shape, the circumferential radiopaque marker bands may be visualized to confirm that the distal portion is generally arcuate. In some embodiments, the radiopaque marker bands are located so that when the distal portion assumes its generally arcuate configuration, the marker bands are at the distal most point of the catheter, i.e., actually beyond a distal end of the catheter (e.g., beyond the distal end 116 of the catheter 102 shown in FIGS. 1A and 1B; or beyond the distal end 616 of the catheter 602 shown in FIGS. 6A and 6B).

The radiopaque markers comprise a radiopaque material, for example platinum, tantalum, tungsten, palladium, and/or iridium. Other radiopaque materials are also possible. In some embodiments, a material may be considered radiopaque, for example, if the average atomic number is greater than 24 or if the density is greater than about 9.9 g/cm$^3$. In some embodiments a distal portion of the catheter (e.g., the distal portion 104 of the catheter 102 of FIGS. 1A and 1B; and the distal portion 604 of the catheter 602 of FIGS. 6A and 6B) may be infused with a radiopaque material so that the entire distal portion is visible using imaging techniques.

In some embodiments, an outer sheath of an embolic protection device as described herein comprises a hollow tube configured to circumferentially surround at least a portion of the catheter. For example, the outer sheath 112 of the embolic protection device 100 of FIGS. 1A-1F or the outer sheath 612 of the embolic protection device 600 of FIGS. 6A-6G. The outer sheath is longitudinally movable with respect to the catheter and is configured to at least partially contain or house the embolic filter in a collapsed configuration when circumferentially surrounding the embolic filter, for example, as shown in FIG. 1A and FIG. 6A. The outer sheath is longitudinally proximally retractable to release the embolic filter to the expanded, open configuration when not contained by the outer sheath.

In some embodiments, the outer sheath extends proximally to a proximal end of the catheter (e.g., the proximal end 114 of the catheter 102 shown in FIG. 1A or the proximal end 614 of the catheter 602 shown in FIG. 6A) so that the user can grasp and manipulate the outer sheath directly. In some embodiments, the outer sheath extends proximally over only a portion of the catheter, and a secondary device (e.g., a push-rod such as found in stent deployment systems) is coupled to the outer sheath (e.g., to the proximal end of the outer sheath) to allow for indirect manipulation of the outer sheath. Manipulation of the outer sheath may be mechanical, electronic, manual, combinations thereof, and the like.

In some embodiments, an embolic protection device as described herein may have a longitudinally extending groove (not shown) along its outer surface. For example, the embolic protection device 100 of FIG. 1B includes a longitudinally extending groove along the catheter 102, along the support catheter 150, or along the deployment mechanism (e.g. outer sheath) 112. In another example, the embolic protection device 600 of FIG. 6B includes a longitudinally extending groove along the catheter 602, along the support catheter 650, or along the deployment mechanism/ outer sheath 612. In some embodiments, the groove may extend substantially from the proximal end to the distal end of the embolic protection device. The groove may be useful for guiding another catheter device alongside the embolic protection device. For example, the groove may be useful for guiding a valve delivery device alongside and beyond the distal end of the embolic protection device. Advantageously, the second device may be tracked along the groove and pass beyond the embolic protection device while the embolic filter is deployed as shown, for example, in FIG. 13A.

A device according to the disclosure herein can comprise some or all of the features of the embolic protection device 100, 200, 300, 400, 500, 600, 700, and 800 as shown in FIGS. 1A-1F; FIGS. 2A and 2B; FIGS. 3A-3D; FIGS. 4A-4C; FIGS. 5A and 5B; FIGS. 6A-6G; FIGS. 7A-7C; and FIGS. 8A-8F; and is described herein in various combinations.

III. METHODS OF CAPTURING EMBOLIC DEBRIS

Another aspect of the present invention provides a method 900 of capturing embolic debris during a closed-heart medical procedure (e.g., an aortic valve replacement procedure), as illustrated in a stepwise fashion in FIGS. 9A-9E, using an embolic protection device of the present invention (e.g., the embolic protection device 100, 200, 300, 400, or 500 as described herein).

Figure 9A:
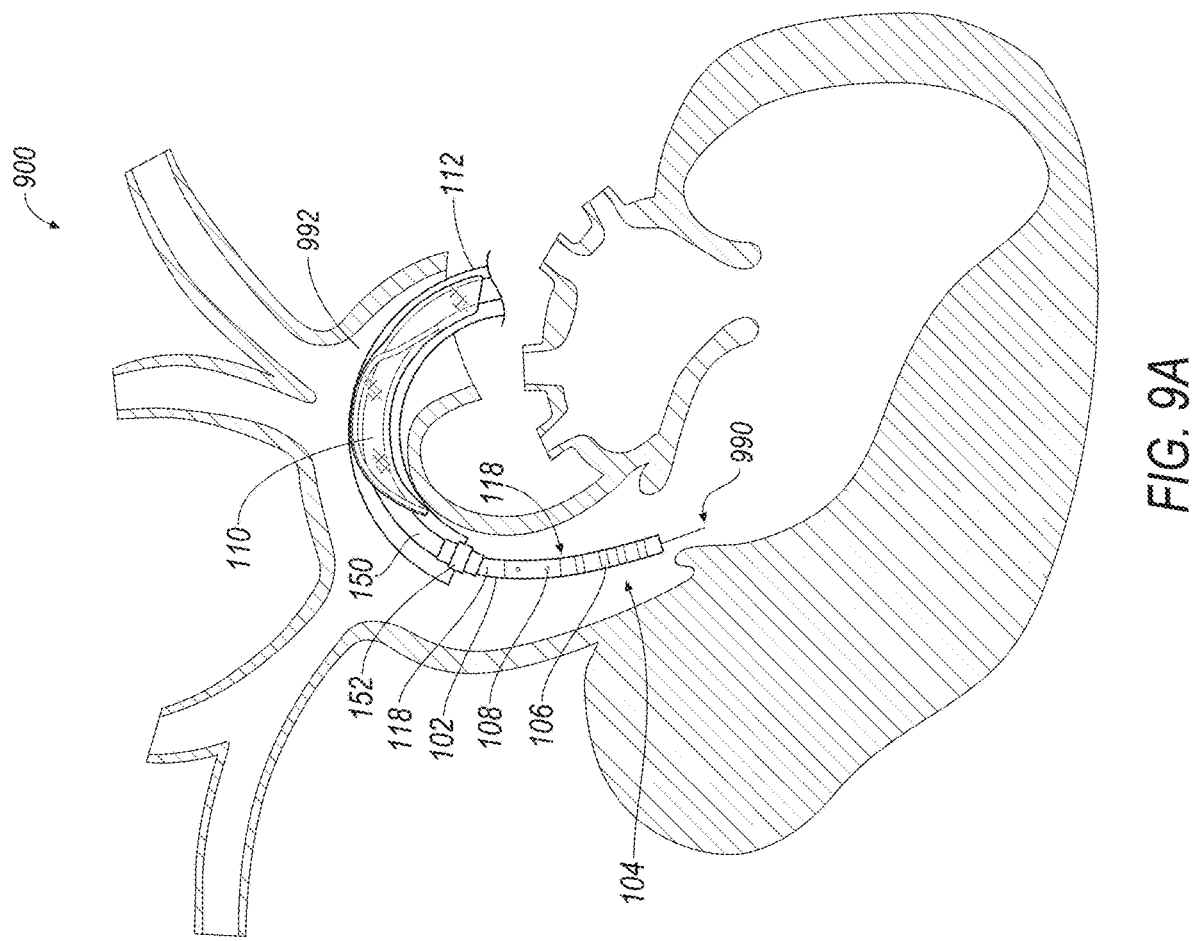
FIGS. 9A-9E illustrate a stepwise method of using an embolic protection device of the present invention.

Referring to FIG. 9A, in one embodiment, a guidewire 990 is percutaneously inserted into a body lumen 992 of a patient, for example a femoral, radial, brachial, or subclavian artery, and navigated to the desired anatomical location, for example, the ascending aorta. The guidewire 990 can be a J-tipped wire having a diameter of about 0.035 in. (approx. 0.089 cm). Other types and dimensions of guidewires 990 useful for this method are also possible.

In some embodiments, the proximal end of the guidewire 990 is inserted into the opening at the distal end 116 of the catheter 102. When the guidewire 990 is in the lumen 118 of the catheter 102 at the distal portion 104 of the catheter 102, the distal portion 104 of the catheter is straightened or assumes the curvature of the guidewire 990. The distal end 116 of the catheter 102 is inserted into the body lumen 992 by tracking the lumen 118 of the catheter 102 over the guidewire 990, as shown in FIG. 9A. The outer diameter of the guidewire 990 is smaller than the inner diameter of the embolic protection device 100 such that the embolic protection device 100 may be tracked over the guidewire 990. The inner surface of the lumen 118 and/or the outer surface of the guidewire 990 may include a lubricious coating to reduce friction during tracking. The guidewire 990 keeps the distal portion 104 of the catheter 102 substantially straight (e.g., from being in the generally arcuate state) as the catheter 102 is inserted into and navigated within the patient's body.

Figure 9B:
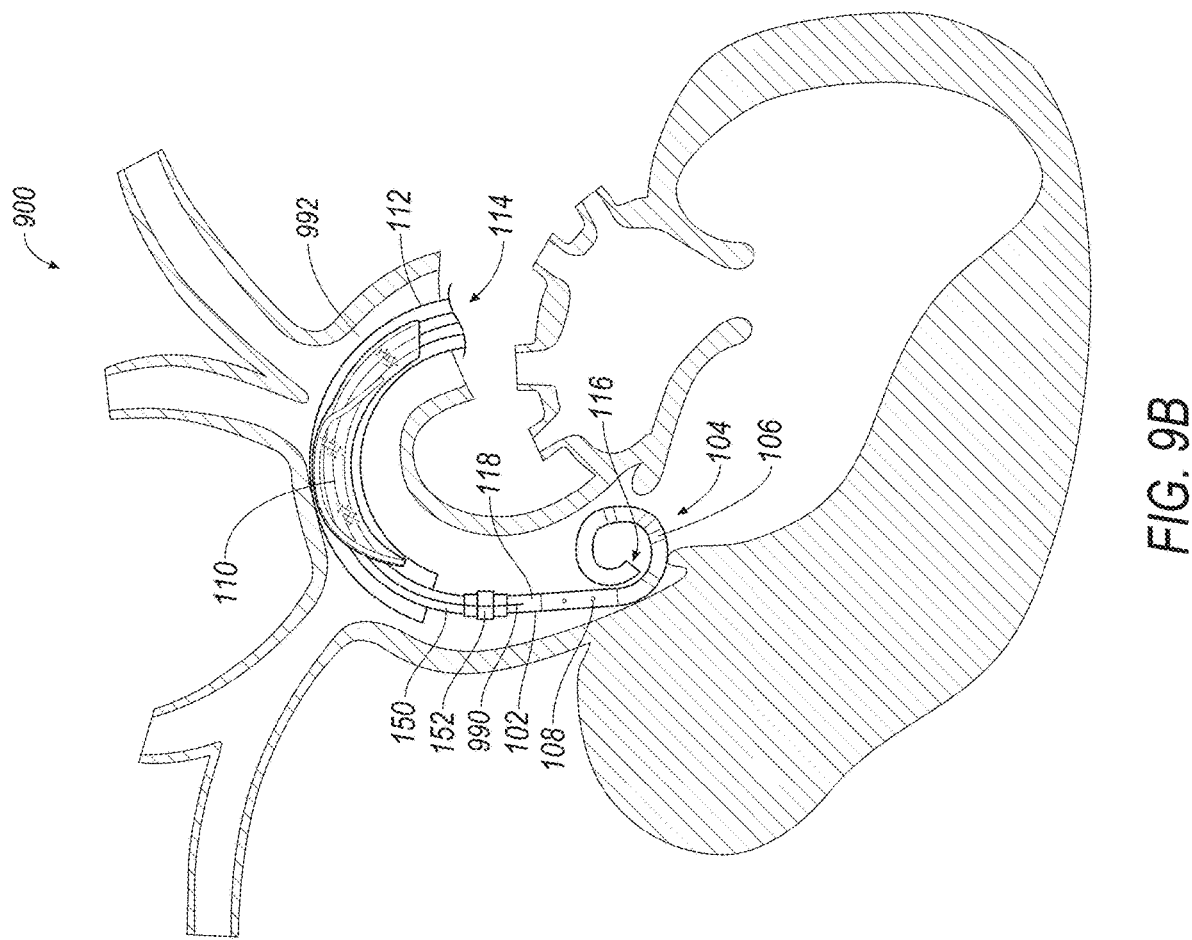

The radiopaque marker(s) 106 are used to visualize and position the distal portion 104 of the catheter 102 during tracking. The guidewire 990 is retracted, i.e., moved longitudinally in a proximal direction, a sufficient distance to allow the distal portion 104 of the catheter 102 to assume the generally arcuate shape, as shown in FIG. 9B. The distal portion 104 of the catheter 102 is positioned at the desired anatomical landmark, for example, the lower border of the noncoronary cusp of the aortic valve. The radiopaque marker(s) 106 are on the distal-most section of the distal portion 104 when the distal portion 104 assumes its generally arcuate shape. In some embodiments the distal portion 104 of the catheter 102 may be infused with a radiopaque material so that the entire distal portion 104 is visible using imaging techniques.

In some embodiments of the method, the proximal end 114 of the catheter 102 is connected to a contrast material injector, and contrast material is injected into the lumen 118 of the catheter 102, for example to visualize the anatomy around the device 100. The contrast material exits the catheter 102 lumen 118 through the opening at the distal end 116 of the catheter 102 and/or through one or more apertures 108 in the side wall of the catheter 102. Injecting contrast material can aid in visualizing and positioning the catheter 102.

Figure 9C:
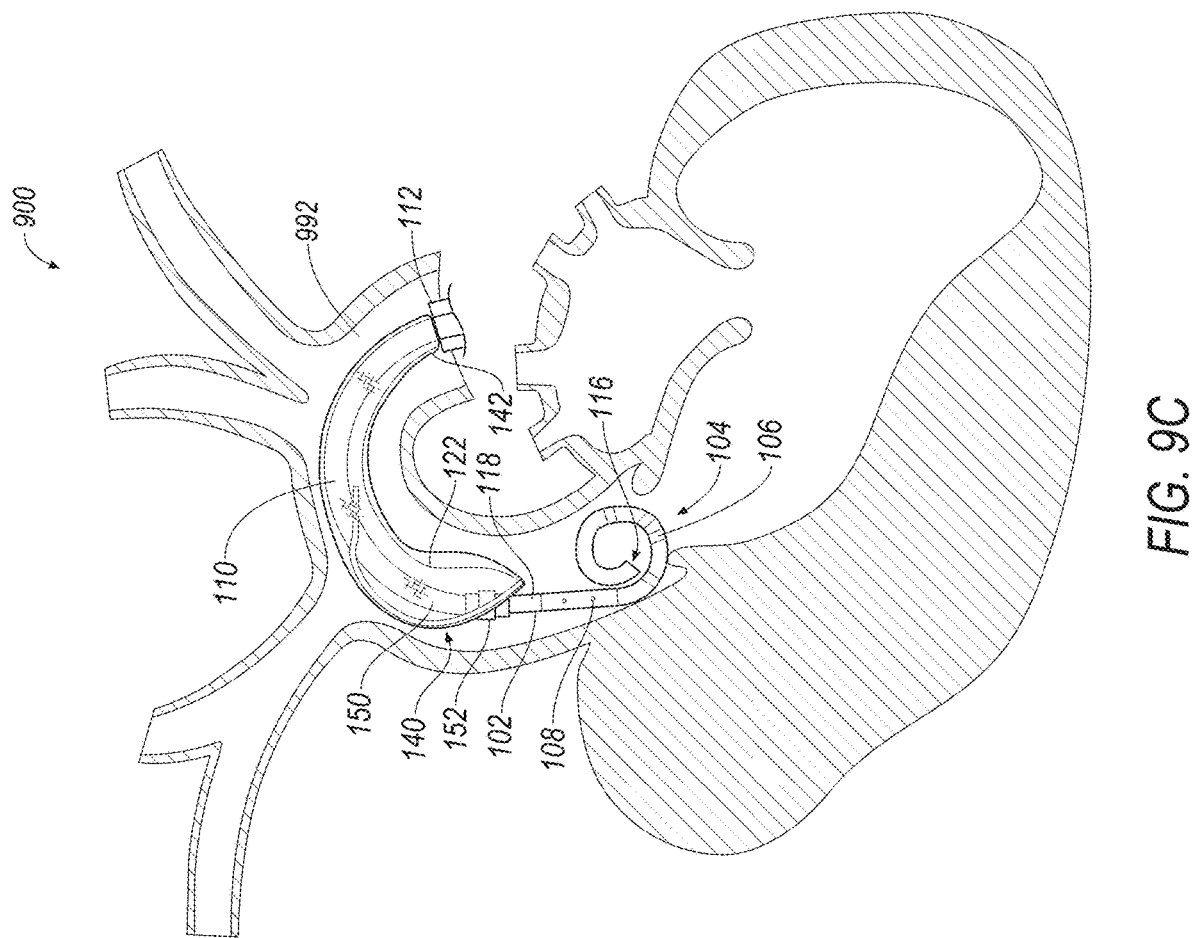

In some embodiments, a second guidewire is percutaneously inserted into a second body lumen, for example the other femoral artery, and a second catheter is tracked over the second guidewire. The second catheter can carry a medical device or instrument, for example, a replacement valve, a valve repair system, or a radio frequency ablation system. Once the second catheter and associated device or instrument are properly positioned, the outer sheath 112 of the catheter 102 is longitudinally proximally retracted, allowing the embolic filter 110 to assume the expanded, deployed configuration, as shown in FIG. 9C.

Figure 9D:
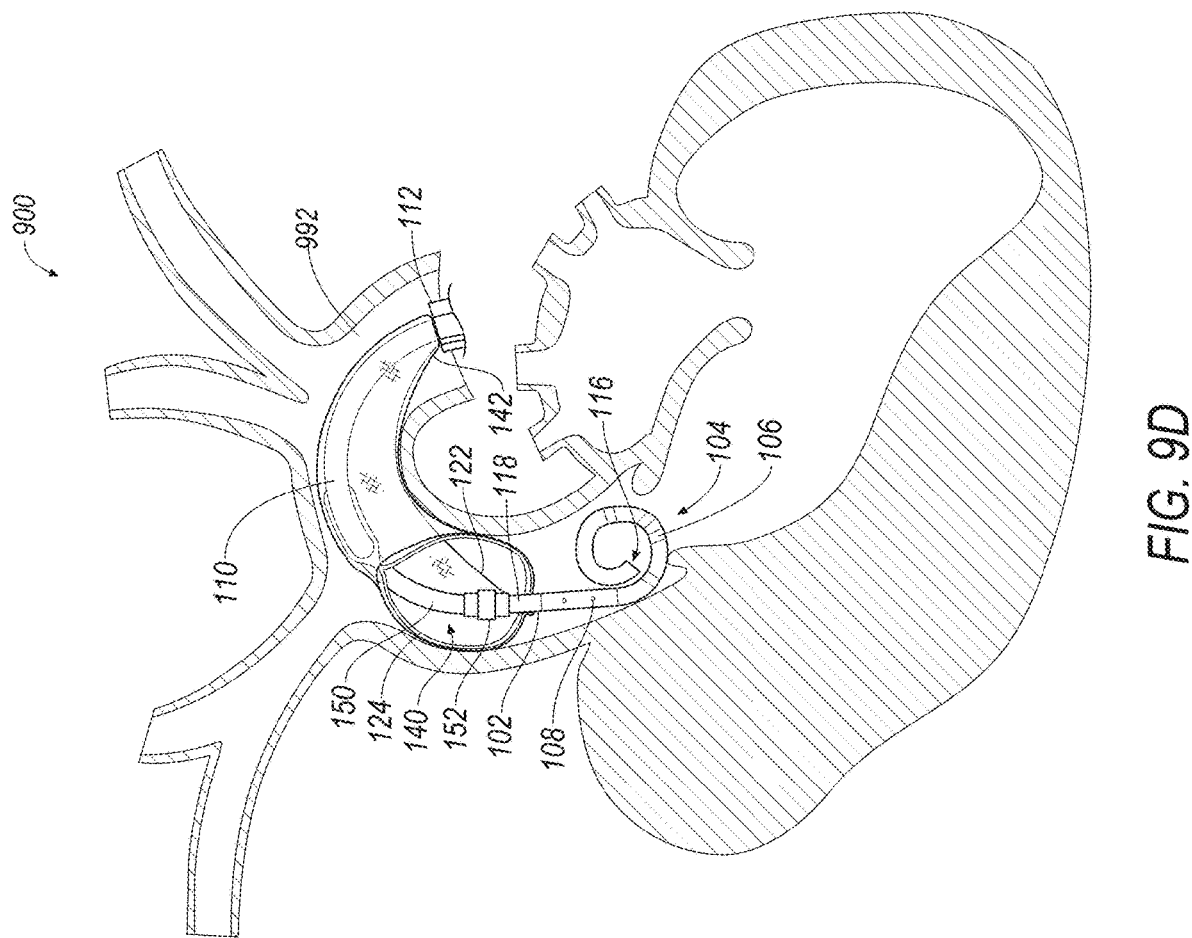
Figure 9E:
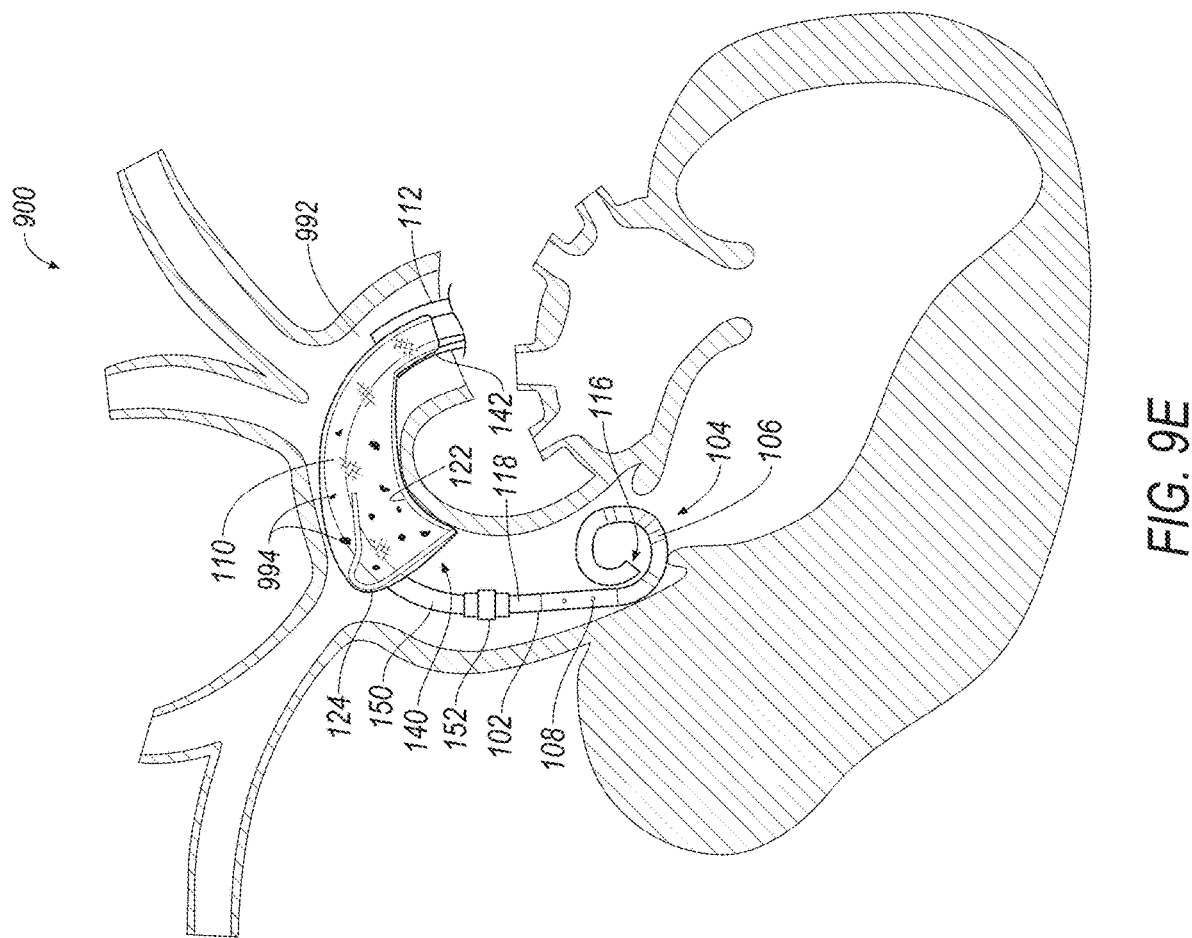

Next, the pull wire 122 can be retracted to bend the frame 124 of the embolic filter 110. The pull wire 122 bends the frame 124 in a proximal longitudinal direction and laterally outward. In a fully bent configuration (i.e., with pull wire fully retracted), as shown in FIGS. 9D and 9E, the distal opening 140 of the embolic filter 110 may be substantially perpendicular to the catheter 102 and may span laterally across the body lumen 992, substantially perpendicular to the longitudinal axis of the body lumen 992. The fully bent configuration may engage the body lumen 992, thereby capturing embolic debris 994 in the embolic filter 110 without allowing embolic debris to travel around the outside of the embolic filter 110. The second guidewire and/or the second catheter can also be positioned after the embolic filter 110 is deployed. The distal opening 140 of the embolic filter 110 is located in the ascending aorta so that blood flows through the filter before flowing into the carotid arteries or descending aorta. In some embodiments, when the embolic filter 110 is deployed, the catheter 102 rests against the interior lumen wall, thereby stabilizing the catheter 102. The procedure can then be performed, and embolic debris dislodged or otherwise in the blood stream during the procedure is captured by the embolic filter 110.

After the procedure, the pull wire 122 is advanced and the outer sheath 112 is longitudinally distally advanced to recapture the embolic filter 110, returning the frame to the unbent configuration and returning the embolic filter 110 to the collapsed configuration and capturing any embolic debris 994 (see FIG. 9E) contained within the embolic filter 110. The second catheter and catheter 102 can then be withdrawn from the patient's body. The catheter 102 can be retracted over the guidewire 990 or without straightening the distal portion 104 of the catheter 102 because the arcuate shape of the distal portion 104 is atraumatic to the blood vessels.

In some embodiments, the procedure performed is a cardiac valve replacement procedure, for example an aortic valve replacement procedure. The embolic protection device 100 is introduced into the patient and navigated to the aortic valve as described herein and shown in FIGS. 9A-9E. The radiopaque marker(s) 106 assist in delineating the lower border of the noncoronary cusp to assist in proper positioning of a percutaneously implanted replacement aortic valve. Once the catheter 102 is positioned, a second guidewire can be percutaneously inserted into a second body lumen and navigated to the level of the ascending aorta or left ventricle. A balloon can be tracked over the second guidewire to the aortic valve. The outer sheath 112 is then retracted to deploy the embolic filter 110 and the pull wire 122 is retracted to bend the frame 124 to a bent configuration. Balloon inflation of the valve can then be performed, and the embolic filter 110 captures embolic debris 994 dislodged during the procedure or otherwise in the blood stream. After balloon pre-dilation, the pull wire 122 is advanced and the outer sheath 112 is advanced to recapture the embolic filter 110 and any embolic debris 994 contained within the embolic filter 110. The balloon is removed, and a second catheter carrying a valvular prosthesis is advanced to the level of the ascending aorta by tracking the catheter over the second guidewire. The outer sheath 112 is again retracted to redeploy the embolic filter 110 and the pull wire 122 is again retracted. The radiopaque marker(s) 106 allow the user to properly position the valve prosthesis, for example about 4 mm to about 6 mm below the lower border of the noncoronary cusp. After the procedure is completed, the pull wire 122 is advanced and the outer sheath 112 is advanced to recapture the embolic filter 110 and any captured embolic debris 994, and the catheters are removed from the body. In some embodiments, the second catheter can be removed prior to recapturing the embolic filter 110 and embolic debris 994.

In some embodiments, the procedure is a cardiac valve repair procedure. The method described herein can also be adapted for a mitral valve repair or replacement procedure. In some embodiments, the procedure is a radio frequency ablation procedure, for example to treat atrial fibrillation. In some embodiments, the procedure is a catheterization procedure or structural heart procedure.

In some embodiments, a method of capturing embolic debris as described herein may include inserting a second catheter device through the same vessel as the embolic protection device. The second catheter device may be inserted after the embolic protection device and may be tracked along a longitudinal groove in the outer surface of the embolic protection device. For example, a valve delivery catheter device may be guided alongside the embolic protection device and beyond the distal end of the embolic protection device by tracking the valve delivery device along the groove. Advantageously, the second device may be tracked along the groove and pass beyond the embolic protection device while the embolic filter is deployed as shown, for example, in FIG. 13A.

Figure 10:
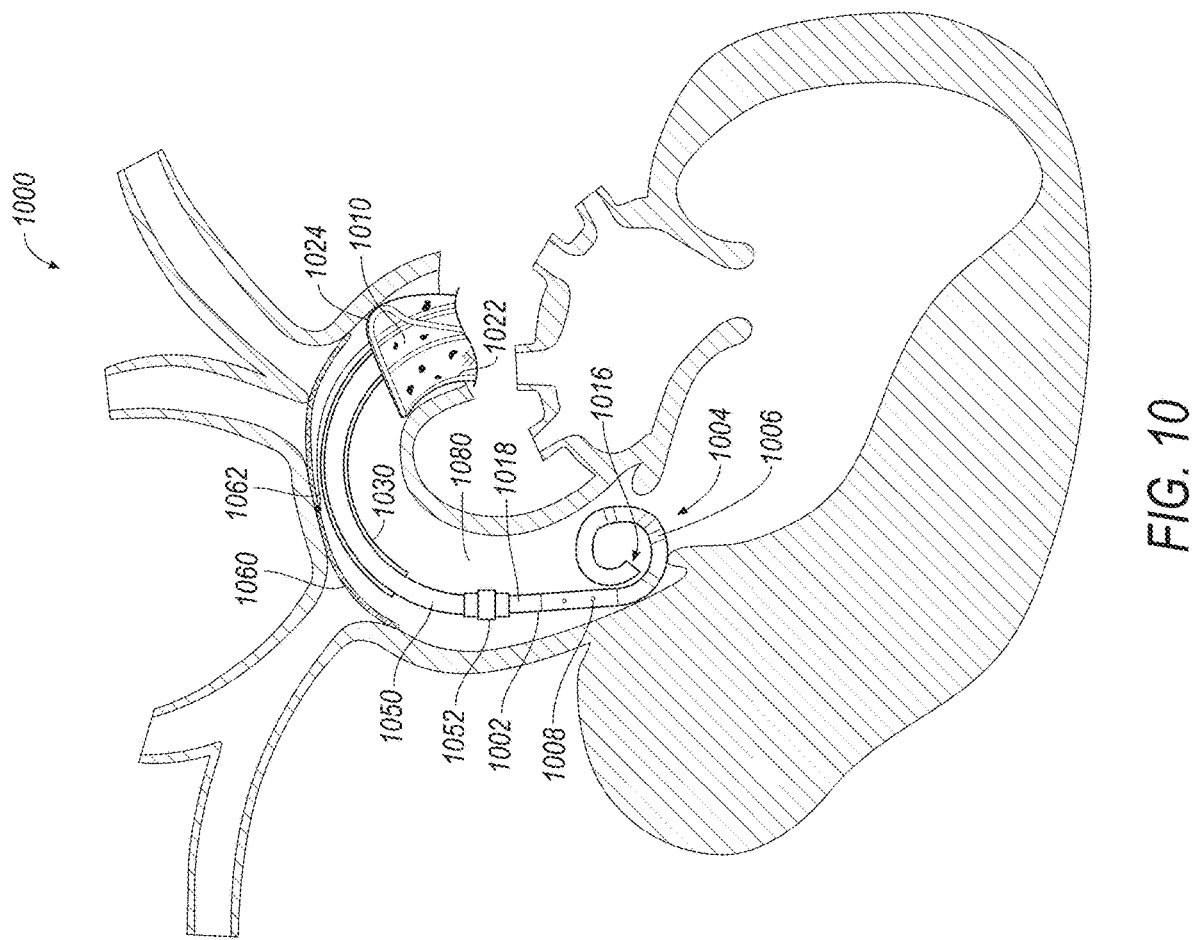
FIG. 10 illustrates the deflection and capture of embolic debris by an embolic protection device of the present invention comprising a deflector.

FIG. 10 illustrates another embodiment of a method 1000 of deflecting and capturing embolic debris during a medical procedure using an embolic protection device 1001. The embolic protection device 1001 is similar to the embolic protection device 300 that is described in FIGS. 3A-3D, in that it has an intermediate tube 1030. The embolic protection device 1001 further comprises an embolic filter 1010 that is movably coupled to a catheter 1002 by way of a frame 1024 and is longitudinally movable with respect to the catheter 1002. As shown in the figure, the catheter 1002 is at least partially surrounded by a support catheter 1050 that terminates at a head 1052, proximal to a distal portion 1004 of the catheter 1002. The embolic filter 1010 is coupled to the intermediate tube 1030 that at least partially circumferentially surrounds the support catheter 1050. The intermediate tube 1030 is longitudinally movable with respect to the catheter 1002.

The embolic protection device 1001 further comprises an outer sheath (not shown) configured to at least partially circumferentially surround both the catheter 1002/support catheter 1050 and the intermediate tube 1030. The intermediate tube 1030 and the outer sheath can be moved simultaneously and independently. The longitudinal position of the embolic filter 1010 with respect to the catheter 1002 can be adjusted while the embolic filter 1010 is in the collapsed configuration or in a deployed or partially deployed, expanded configuration.

The method 1000 includes capturing emboli using the embolic protection device 1001 in a manner similar to the method 900 described above with reference to FIGS. 9A-9E. For example, a distal end 1016 of the catheter 1002 is inserted into a body lumen 1080 of a patient by tracking a lumen 1018 of the catheter 1002 over a guidewire, which was previously percutaneously inserted into the body lumen 1080. The guidewire keeps a distal portion 1004 of the catheter 1002 substantially straight (e.g., from being in the generally arcuate state) as the catheter 1002 is inserted into and navigated within the patient's body. The radiopaque marker 1006 is used to visualize and position the distal portion 1004 of the catheter 1002 during tracking. Visualization may also be accomplished by perfusing imaging dye or contrast agent through apertures 1008 in the distal portion 1004 of the catheter 1002. Once positioned at the desired anatomical landmark (e.g., the lower border of the noncoronary cusp of the aortic valve), the guidewire is retracted a sufficient distance to allow the distal portion 1004 of the catheter 1002 to assume the generally arcuate shape, as shown in FIG. 10.

The longitudinal position of the embolic filter 1010 within the body lumen 1080 can be adjusted by simultaneously moving the intermediate tube 1030 and the outer sheath. When the embolic filter 1010 is in the desired longitudinal position within the body lumen 1080, the intermediate tube 1030 is held stationary while the outer sheath is retracted to deploy the embolic filter 1010. Next, the pull wire 1022 is retracted to bend the frame 1024 and open the embolic filter 1010 to capture emboli.

The method 1000 further includes deflecting emboli. The embolic protection device 1001 also comprises a deflector 1060 similar to that shown in FIGS. 4A-C. Once the embolic protection device 1001 is in position (as described above), the deflector 1060 is deployed from the outer sheath to cover the brachiocephalic and left common carotid artery. In some patients, the deflector 1060 might also cover the left subclavian artery. During a subsequent medical procedure, the deflector 1060 can prevent emboli from entering the carotid arteries, and the embolic filter 1010 can capture emboli deflected by the deflector 1060 before it travels to other parts of the patient's body. The method 1000 can also be performed with various other embolic protection devices, for example as described herein, and deflector devices that may vary in configuration and how they are introduced into the body and navigated to the aortic arch.

Figure 11:
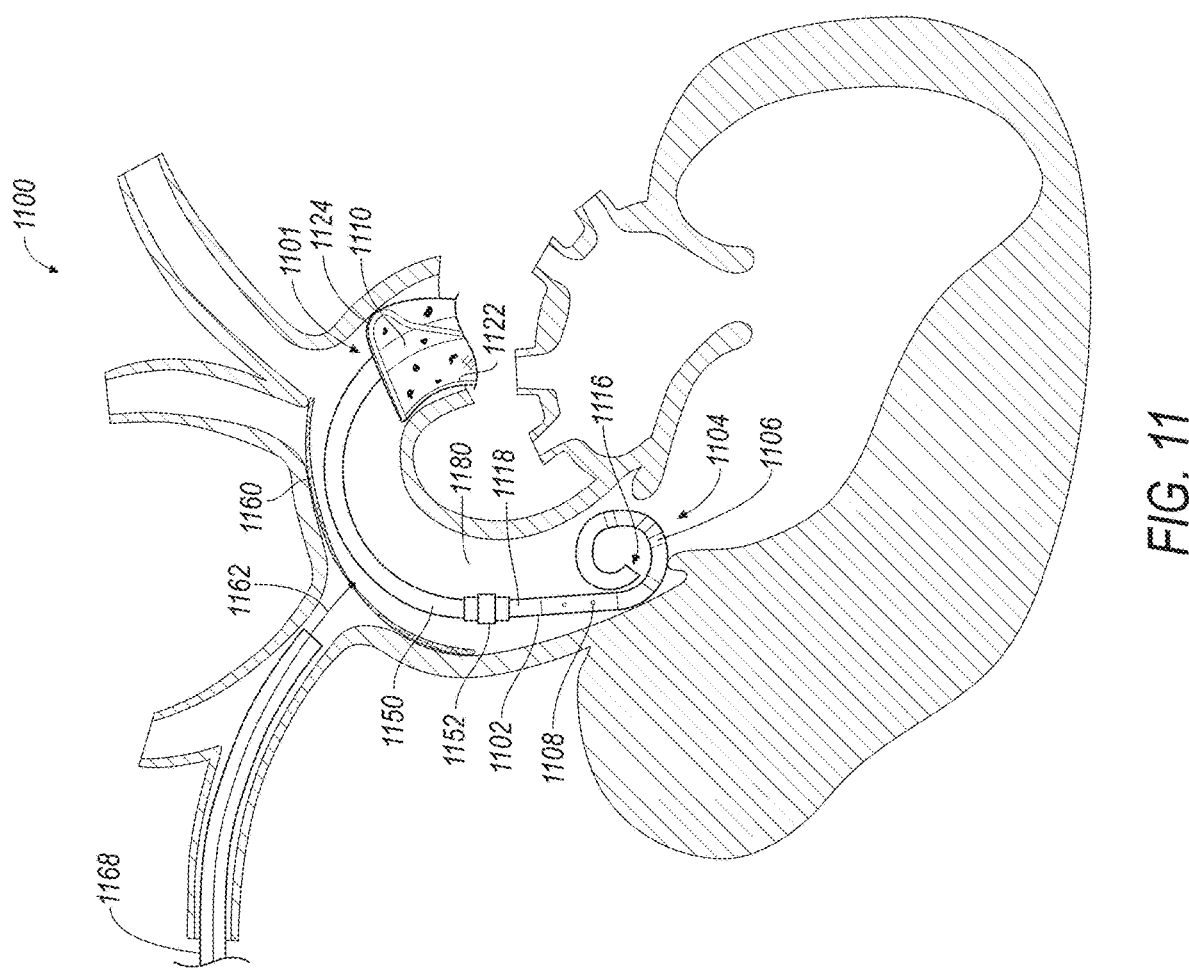
FIG. 11 illustrates the deflection and capture of embolic debris by an embolic protection device of the present invention wherein a second catheter device is present.

FIG. 11 illustrates another embodiment of a method 1100 of deflecting and capturing embolic debris. An embolic protection device 1101 comprises a catheter 1102 (e.g., a pigtail catheter) with a radiopaque marker 1106 and an embolic filter 1110 disposed around the catheter 1102 similar to the embolic filter 110 illustrated in FIGS. 1A-1F and described herein. As shown in the figure, the catheter 1102 is partially surrounded by a support catheter 1150 that terminates at a head 1152, proximal to a distal portion 1104 of the catheter 1102.

The method 1100 includes capturing emboli using the embolic protection device 1101 in a manner similar to the method 900 described above with reference to FIGS. 9A-9E. For example, a distal end 1116 of the catheter 1102 is inserted into a body lumen 1180 of a patient by tracking a lumen 1118 of the catheter 1102 over a guidewire, which was previously percutaneously inserted into the body lumen 1180. The guidewire keeps a distal portion 1104 of the catheter 1102 substantially straight (e.g., from being in the generally arcuate state) as the catheter 1102 is inserted into and navigated within the patient's body. The radiopaque marker 1106 is used to visualize and position the distal portion 1104 of the catheter 1102 during tracking. Visualization may also be accomplished by perfusing imaging dye or contrast agent through apertures 1108 in the distal portion 1104 of the catheter 1102.

Once positioned at the desired anatomical landmark (e.g., the lower border of the noncoronary cusp of the aortic valve), the guidewire is retracted a sufficient distance to allow the distal portion 1104 of the catheter 1102 to assume the generally arcuate shape, as shown in FIG. 11. An outer sheath (not shown) of the catheter 1102 is longitudinally, proximally retracted, allowing the embolic filter 1110 to assume the expanded, deployed configuration, as shown in FIG. 11. Next, the pull wire 1122 is retracted to bend the frame 1124 and open the embolic filter 1110 to capture emboli.

The method 1100 further includes deflecting emboli with a deflector 1160. As shown, the deflector 1160 is mounted to a shaft 1162 and contained in an introducer 1168 during insertion. The introducer 1168 is introduced into the patient's body through the artery (e.g., right radial artery) and navigated to the aortic arch via the brachiocephalic artery. Once in position, the deflector 1160 is deployed from the introducer 1168 and pulled back to cover the brachiocephalic and left common carotid artery. In some patients, the deflector 1160 might also cover the left subclavian artery. In some embodiments, the deflector 1160 can be introduced and deployed before the catheter 1102 is navigated to the aortic arch. During a subsequent medical procedure, the deflector 1160 can prevent emboli from entering the carotid arteries, and the embolic filter 1110 can capture emboli deflected by the deflector 1160 before it travels to other parts of the patient's body. The method 1100 can also be performed with various other embolic protection devices, for example as described herein, and deflector devices that may vary in configuration and how they are introduced into the body and navigated to the aortic arch.

Another aspect of the present invention provides a method of capturing embolic debris during a closed-heart procedure, comprising inserting a distal end of a embolic protection device into a body lumen, the embolic protection device comprising a catheter having a proximal end, a distal end, and a lumen extending from the proximal end of the catheter to the distal end of the catheter, wherein the lumen is configured to house a guidewire, and a distal portion of the catheter that assumes a generally arcuate shape being at least a semi-circle when the guidewire is at least partially longitudinally retracted; a self-expanding embolic filter that is disposed around the catheter proximal to the distal portion, wherein the embolic filter comprises a frame, and the frame defines an opening of the embolic filter; a deployment mechanism that is disposed around at least a portion of the catheter, wherein the deployment mechanism is longitudinally movable with respect to the catheter, the deployment mechanism is configured to contain the embolic filter in a collapsed configuration, and the embolic filter is configured to self-expand upon longitudinal retraction of the deployment mechanism; and a pull wire coupled to the frame of the embolic filter, wherein the wire is longitudinally movable, and when longitudinally retracted, bends the frame longitudinally toward the proximal end of the catheter and laterally outward from the catheter, such that the opening of the embolic filter generally faces the distal end of the catheter. The method further includes tracking the lumen of the catheter over the guidewire that is percutaneously inserted into the body lumen.

Some embodiments further comprise at least partially longitudinally retracting the guidewire from the lumen of the catheter, so that the distal portion of the catheter assumes a generally arcuate shape being at least a semi-circle.

In some embodiments, the distal portion of the catheter comprises a radiopaque marker; and the method further comprises positioning the catheter by visualizing the radiopaque marker using an imaging technique.

Some embodiments comprise at least partially longitudinally retracting the deployment mechanism and allowing the self-expanding embolic filter to assume an expanded, deployed configuration.

Some embodiments comprise longitudinally retracting the wire, thereby bending the frame longitudinally toward the proximal end of the catheter and laterally outward from the catheter, wherein the opening defined by the frame substantially spans the body lumen.

Some embodiments comprise longitudinally retracting the wire to a proximal position, thereby bending the frame so that the opening of the filter defined by the frame is substantially perpendicular to the longitudinal direction of the catheter, wherein the opening defined by the frame substantially spans the body lumen.

In some embodiments, the embolic filter is movably coupled to the catheter and is longitudinally moveable with respect to the catheter, and the method comprises longitudinally moving the embolic filter with respect to the catheter.

In some embodiments, the embolic protection device comprises a self-expanding deflector coupled to the catheter proximal to the distal portion, and the method comprises deploying the self-expanding deflector to direct embolic debris toward the embolic filter.

In some embodiments, the deployment mechanism is a sheath that is circumferentially disposed around at least a portion of the catheter.

In some embodiments, the distal portion of the catheter comprises one or more apertures that communicate with the lumen of the catheter; the method further comprising perfusing a fluid into the body lumen through the one or more apertures.

In some embodiments, the embolic protection device comprises a longitudinal groove along an outer surface of the embolic protection device; the method further comprising inserting a second catheter device alongside the embolic protection device by tracking the second catheter device along the groove.

In some embodiments, the second catheter device is advanced past the embolic filter of the embolic protection device while the embolic filter is in a deployed configuration.

Another aspect of the present invention provides a method of capturing embolic debris during a closed-heart procedure, the method comprising inserting a distal end of a embolic protection device into a body lumen, the embolic protection device comprising a catheter having a proximal end, a distal end, and a lumen extending from the proximal end of the catheter to the distal end of the catheter, wherein the lumen is configured to house a guidewire, and a distal portion of the catheter assumes a generally arcuate shape being at least a semi-circle when the guidewire is at least partially longitudinally retracted; a self-expanding embolic filter that is disposed around the catheter proximal to the distal portion, wherein the embolic filter comprises a frame, and the frame defines an opening of the embolic filter; a deployment mechanism that is disposed around at least a portion of the catheter, wherein the deployment mechanism is longitudinally movable with respect to the catheter, the deployment mechanism is configured to contain the embolic filter in a collapsed configuration, and the embolic filter is configured to self-expand upon longitudinal retraction of the deployment mechanism; a wire coupled to the frame of the self-expanding filter, wherein the wire is longitudinally movable, and when longitudinally retracted, bends the frame longitudinally toward the proximal end of the catheter and laterally outward from the catheter, such that the opening of the embolic filter generally faces the distal end of the catheter The method further includes tracking a lumen of the catheter over a guidewire that is percutaneously inserted into the body lumen and at least partially longitudinally retracting the guidewire from the lumen of the catheter, so that the distal portion of the catheter assumes a generally arcuate shape being at least a semi-circle upon retracting the guidewire from the distal portion of the catheter. The method further includes longitudinally retracting the deployment mechanism and deploying the self-expanding embolic filter. The method further includes longitudinally retracting the wire and bending the frame of the embolic filter longitudinally toward the proximal end of the catheter and laterally outward from the catheter.

Yet another aspect of the present invention provides a method 1200 of capturing embolic debris during a closed-heart medical procedure (e.g., an aortic valve replacement procedure), as illustrated in a stepwise fashion in FIGS. 12A-12D, using an embolic protection device of the present invention (e.g., the embolic protection device 600, 700, or 800 as described herein).

Figure 12A:
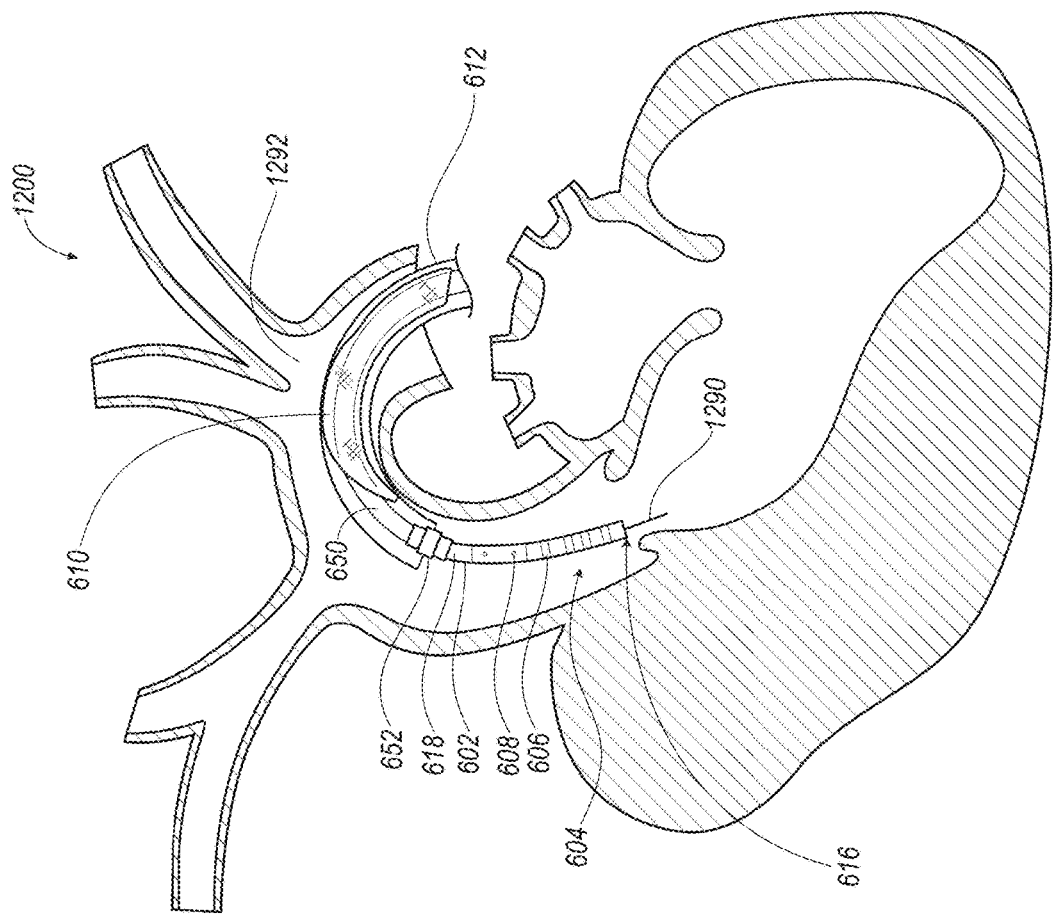
FIGS. 12A-12D illustrate a stepwise method of using an embolic protection device of the present invention operating an embolic filter.

Referring to FIG. 12A, in one embodiment, a guidewire 1290 is percutaneously inserted into a body lumen 1292 of a patient, for example a femoral, radial, brachial, or subclavian artery, and navigated to the desired anatomical location, for example, the ascending aorta. The guidewire 1290 can be a J-tipped wire having a diameter of about 0.035 in. (approx. 0.089 cm). Other types and dimensions of guidewires useful for this method are also possible.

In other embodiments, the proximal end of the guidewire 1290 is inserted into the opening at the distal end 616 of the catheter 602. When the guidewire 1290 is in the lumen 618 of the catheter 602 at the distal portion 604 of the catheter 602, the distal portion 604 of the catheter is straightened or assumes the curvature of the guidewire 1290. The distal end 616 of the catheter 602 is inserted into the body lumen 1292 by tracking the lumen 618 of the catheter 602 over the guidewire 1290, as shown in FIG. 12A. The outer diameter of the guidewire 1290 is smaller than the inner diameter of the embolic protection device 600 such that the embolic protection device 600 may be tracked over the guidewire 1290. The inner surface of the lumen 618 and/or the outer surface of the guidewire 1290 may include a lubricious coating to reduce friction during tracking. The guidewire 1290 keeps the distal portion 604 of the catheter 602 substantially straight (e.g., from being in the generally arcuate state) as the catheter 602 is inserted into and navigated within the patient's body.

Figure 12B:
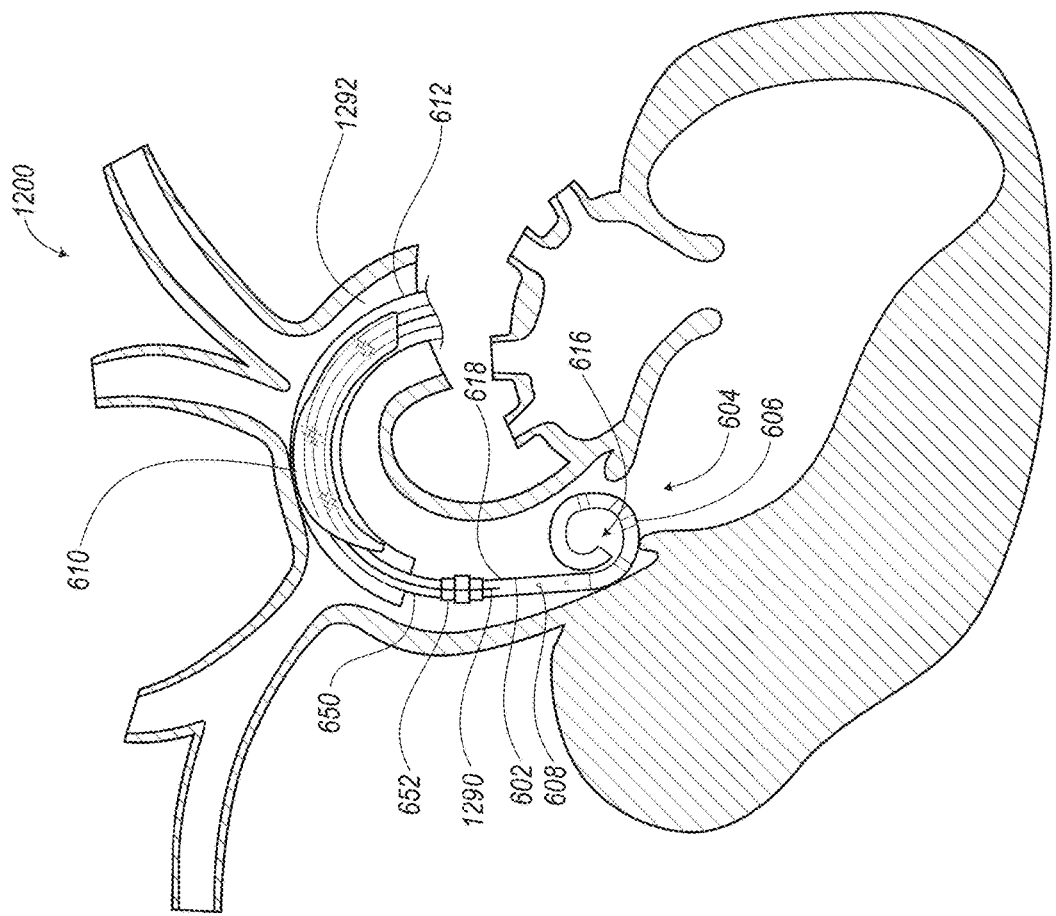

The radiopaque marker(s) 606 are used to visualize and position the distal portion 604 of the catheter 602 during tracking. The guidewire 1290 is retracted, i.e., moved longitudinally in a proximal direction, a sufficient distance to allow the distal portion 604 of the catheter 602 to assume the generally arcuate shape, as shown in FIG. 12B. The distal portion 604 of the catheter 602 is positioned at the desired anatomical landmark, for example, the lower border of the noncoronary cusp of the aortic valve. The radiopaque marker(s) 606 are on the distal-most section of the distal portion 604 when the distal portion 604 assumes its generally arcuate shape. In some embodiments, the distal portion 604 of the catheter 602 may be infused with a radiopaque material so that the entire distal portion 604 is visible using imaging techniques.

In other embodiments of the method, the proximal end 614 of the catheter 602 is connected to a contrast material injector, and contrast material is injected into the lumen 618 of the catheter 602, for example to visualize the anatomy around the embolic protection device 600. The contrast material exits the lumen 618 through the opening at the distal end 616 of the catheter 602 and/or through one or more apertures 608 in the side wall of the catheter 602. Injecting contrast material can aid in visualizing and positioning the catheter 602.

Figure 12C:
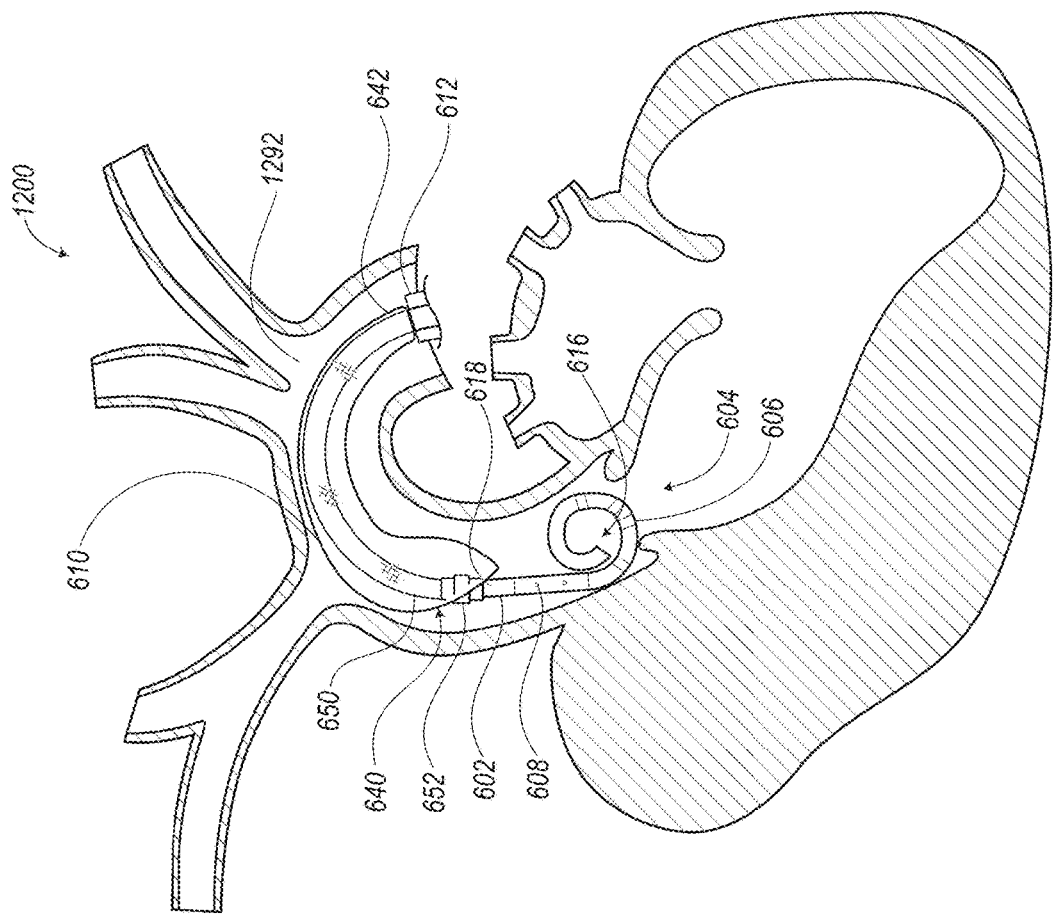

In other embodiments, a second guidewire is percutaneously inserted into a second body lumen, for example the other femoral artery, and a second catheter is tracked over the second guidewire. The second catheter can carry a medical device or instrument, for example, a replacement valve, a valve repair system, or a radio frequency ablation system. Once the second catheter and associated device or instrument are properly positioned, the outer sheath 612 is longitudinally retracted in the proximal direction, allowing the embolic filter 610 to assume the self-expanded, deployed configuration, as shown in FIG. 12C.

Figure 12D:
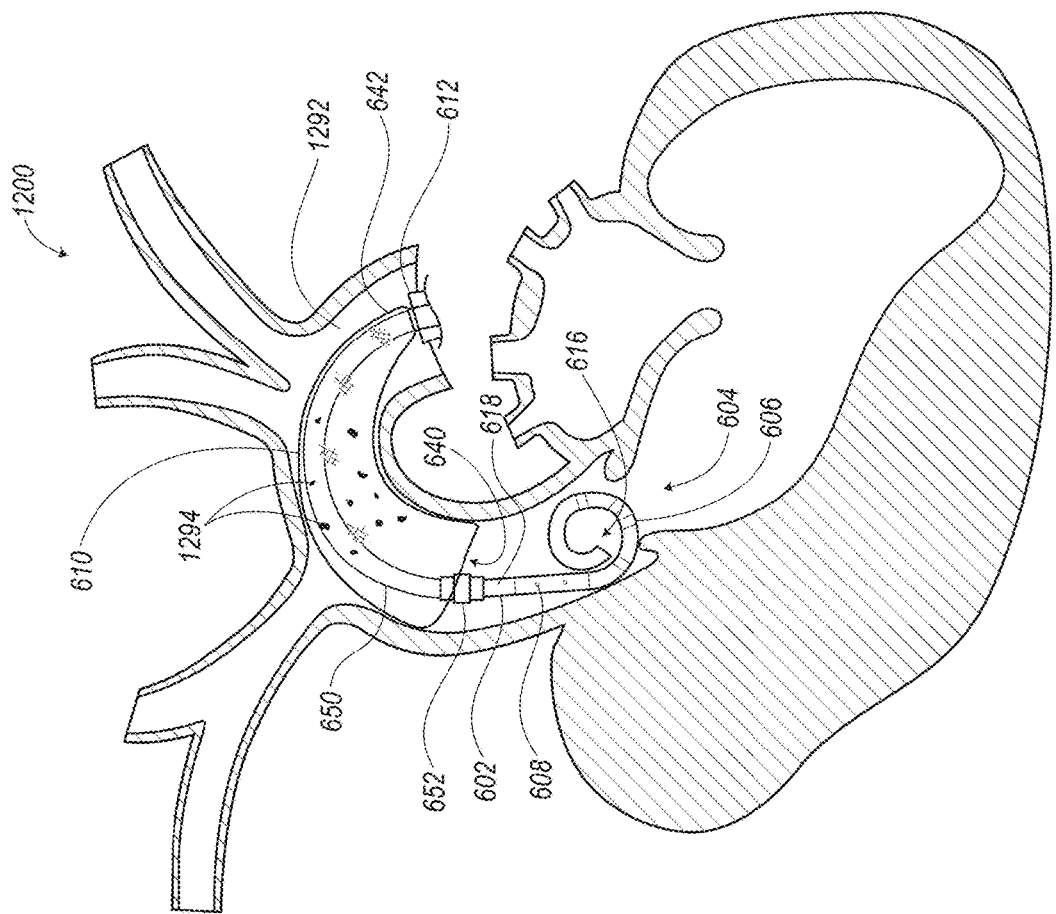

Next, the push wire 622 can be advanced to bend the filter frame of the embolic filter 610. The push wire and the filter frame are not shown in FIGS. 12A-12D, but can be seen in FIGS. 6B-6F as the push wire 622 and the frame 624, respectively. The push wire bends the filter frame in a distal longitudinal direction and laterally outward. In the bent configuration (i.e., with the pull wire advanced in the distal direction), as shown in FIG. 12D, the distal opening 640 of the embolic filter 610 may be substantially perpendicular to the catheter 602 and may span laterally across the body lumen 1292, substantially perpendicular to the longitudinal axis of the body lumen 1292. To accommodate the size of the body lumen 1292, the push wire can be advanced farther to extend the frame in the radial direction and further expand the embolic filter 610.

The bent configuration may engage the body lumen 1292, thereby capturing embolic debris 1294 in the embolic filter 610 without allowing embolic debris to travel around the outside of the embolic filter 610. The second guidewire and/or the second catheter can also be positioned after the embolic filter 610 is deployed. The distal opening 640 of the embolic filter 610 is located in the ascending aorta so that blood flows through the embolic filter 610 before flowing into the carotid arteries or descending aorta. In some embodiments, when the embolic filter 610 is deployed, the catheter 602 rests against the interior lumen wall, thereby stabilizing the catheter 602. The procedure can then be performed and embolic debris 1294 dislodged or otherwise in the blood stream during the procedure is captured by the embolic filter 610.

After the procedure, the push wire 622 is retracted and the outer sheath 612 is longitudinally and distally advanced to recapture the embolic filter 610, returning the filter frame to the unbent configuration and returning the embolic filter 610 to the collapsed configuration. And in turn capturing any embolic debris 1294 (see FIG. 12D) contained within the embolic filter 610. The second catheter and catheter 602 can then be withdrawn from the patient's body. The catheter 602 can be retracted over the guidewire 1290 or without straightening the distal portion 604 of the catheter 602 because the arcuate shape of the distal portion 604 is atraumatic to the blood vessels.

In other embodiments, the procedure performed is a cardiac valve replacement procedure, for example an aortic valve replacement procedure. The embolic protection device 600 is introduced into the patient and navigated to the aortic valve as described herein and shown in FIGS. 12A-12D. The radiopaque marker(s) 606 assist in delineating the lower border of the noncoronary cusp to assist in proper positioning of a percutaneously implanted replacement aortic valve. Once the catheter 602 is positioned, a second guidewire can be percutaneously inserted into a second body lumen and navigated to the level of the ascending aorta or left ventricle. A balloon can be tracked over the second guidewire to the aortic valve. The outer sheath 612 is then retracted to deploy the embolic filter 610 and the push wire 622 is advanced to bend the frame 624 to a bent configuration. And if needed to engage the interior body lumen 1292, the push wire 622 may be advanced even farther to extend the frame 624 to an extended configuration. Balloon inflation of the valve can then be performed, and the embolic filter 610 captures embolic debris 1294 dislodged during the procedure or otherwise in the blood stream. After balloon pre-dilation, the push wire 622 is retracted and the outer sheath 612 is advanced to recapture the embolic filter 610 and any embolic debris 1294 contained within the embolic filter 610. The balloon is removed, and a second catheter carrying a valvular prosthesis is advanced to the level of the ascending aorta by tracking the catheter over the second guidewire. The outer sheath 612 is again retracted to redeploy the embolic filter 610 and the push wire 622 is again advanced. The radiopaque marker(s) 606 allow the user to properly position the valve prosthesis, for example about 4 mm to about 6 mm below the lower border of the noncoronary cusp. After the procedure is completed, the push wire 622 is retracted and the outer sheath 612 is advanced to recapture the embolic filter 610 and any captured embolic debris 1294, and the catheters are removed from the body. In some embodiments, the second catheter can be removed prior to recapturing the embolic filter 610 and embolic debris 1294.

In other embodiments, the procedure is a cardiac valve repair procedure. The method described herein can also be adapted for a mitral valve repair or replacement procedure. In some embodiments, the procedure is a radio frequency ablation procedure, for example to treat atrial fibrillation. In some embodiments, the procedure is a catheterization procedure or structural heart procedure.

In other embodiments, a method of capturing embolic debris as described herein may include inserting a second catheter device through the same vessel as the embolic protection device. The second catheter device may be inserted after the embolic protection device and may be tracked along a longitudinal groove in the outer surface of the embolic protection device. For example, a valve delivery catheter device may be guided alongside the embolic protection device and beyond the distal end of the embolic protection device by tracking the valve delivery device along the groove. Advantageously, the second device may be tracked along the groove and pass beyond the embolic protection device while the embolic filter is deployed as shown, for example, in FIG. 13A.

Another aspect of the present invention provides a method of capturing embolic debris during a closed-heart procedure, comprising inserting a distal end of a embolic protection device into a body lumen, the embolic protection device comprising a catheter having a proximal end, a distal end, and a lumen extending from the proximal end of the catheter to the distal end of the catheter, wherein the lumen is configured to house a guidewire, and a distal portion of the catheter that assumes a generally arcuate shape being at least a semi-circle when the guidewire is at least partially longitudinally retracted; a self-expanding embolic filter that is disposed around the catheter proximal to the distal portion, wherein the embolic filter comprises a frame, and the frame defines an opening of the embolic filter; a deployment mechanism that is disposed around at least a portion of the catheter, wherein the deployment mechanism is longitudinally movable with respect to the catheter, the deployment mechanism is configured to contain the embolic filter in a collapsed configuration, and the embolic filter is configured to self-expand upon longitudinal retraction of the deployment mechanism; and a wire coupled to the frame of the embolic filter, wherein the wire is longitudinally movable with respect to the catheter; when the wire is longitudinally advanced, in a distal direction, to a first position, the wire is configured to bend the frame longitudinally towards the distal end of the catheter and laterally outward from the catheter, such that the opening of the embolic filter generally faces the distal end of the catheter and expands to a first diameter; and when the wire is longitudinally advanced, in the distal direction, to a second position distally farther than the first position, the wire is configured to extend the frame radially outward from the catheter, such that the opening of the embolic filter expands to a second diameter larger than the first diameter. The method further includes tracking the lumen of the catheter over the guidewire that is percutaneously inserted into the body lumen.

Other embodiments further comprise at least partially longitudinally retracting the guidewire from the lumen of the catheter, so that the distal portion of the catheter assumes a generally arcuate shape being at least a semi-circle.

In other embodiments, the distal portion of the catheter comprises a radiopaque marker; and the method further comprises positioning the catheter by visualizing the radiopaque marker using an imaging technique.

Other embodiments comprise at least partially longitudinally retracting the deployment mechanism and allowing the self-expanding embolic filter to assume an expanded, deployed configuration.

Other embodiments comprise longitudinally advancing the wire, thereby bending the frame longitudinally toward the proximal end of the catheter and laterally outward from the catheter, wherein the opening defined by the frame substantially spans the body lumen.

Other embodiments comprise longitudinally advancing the wire to the first position, thereby bending the frame longitudinally towards the distal end of the catheter and laterally outward from the catheter, and expanding the opening of the embolic filter to the first diameter, which substantially spans the body lumen.

Other embodiments comprise longitudinally advancing the wire to the second position distally farther than the first position, thereby extending the frame radially outward from the catheter and expanding the opening of the embolic filter to the second diameter larger than the first diameter, which substantially spans the body lumen.

In other embodiments, the deployment mechanism is a sheath that is circumferentially disposed around at least a portion of the catheter.

In other embodiments, the distal portion of the catheter comprises one or more apertures that communicate with the lumen of the catheter; the method further comprising perfusing a fluid into the body lumen through the one or more apertures.

In other embodiments, the embolic protection device comprises a longitudinal groove along an outer surface of the embolic protection device; the method further comprising inserting a second catheter device alongside the embolic protection device by tracking the second catheter device along the groove.

In other embodiments, the second catheter device is advanced past the embolic filter of the embolic protection device while the embolic filter is in a deployed configuration.

Another aspect of the present invention provides a method of capturing embolic debris during a closed-heart procedure, the method comprising inserting a distal end of a embolic protection device into a body lumen, the embolic protection device comprising a catheter having a proximal end, a distal end, and a lumen extending from the proximal end of the catheter to the distal end of the catheter, wherein the lumen is configured to house a guidewire, and a distal portion of the catheter assumes a generally arcuate shape being at least a semi-circle when the guidewire is at least partially longitudinally retracted; a self-expanding embolic filter that is disposed around the catheter proximal to the distal portion, wherein the embolic filter comprises a frame, and the frame defines an opening of the embolic filter; a deployment mechanism that is disposed around at least a portion of the catheter, wherein the deployment mechanism is longitudinally movable with respect to the catheter, the deployment mechanism is configured to contain the embolic filter in a collapsed configuration, and the embolic filter is configured to self-expand upon longitudinal retraction of the deployment mechanism; a wire coupled to the frame of the self-expanding filter, wherein the wire is longitudinally movable.

The method further includes tracking the lumen of the catheter over the guidewire that is percutaneously inserted into the body lumen and at least partially longitudinally retracting the guidewire from the lumen of the catheter, so that the distal portion of the catheter assumes a generally arcuate shape being at least a semi-circle upon retracting the guidewire from the distal portion of the catheter. The method further includes longitudinally retracting the deployment mechanism and deploying the self-expanding embolic filter. The method further includes longitudinally advancing the wire, in a distal direction, to a first position, thereby bending the frame longitudinally towards the distal end of the catheter and laterally outward from the catheter, and expanding the opening of the embolic filter to a first diameter.

IV. EXAMPLES

Example 1: Cadaver Model

Figure 13A:
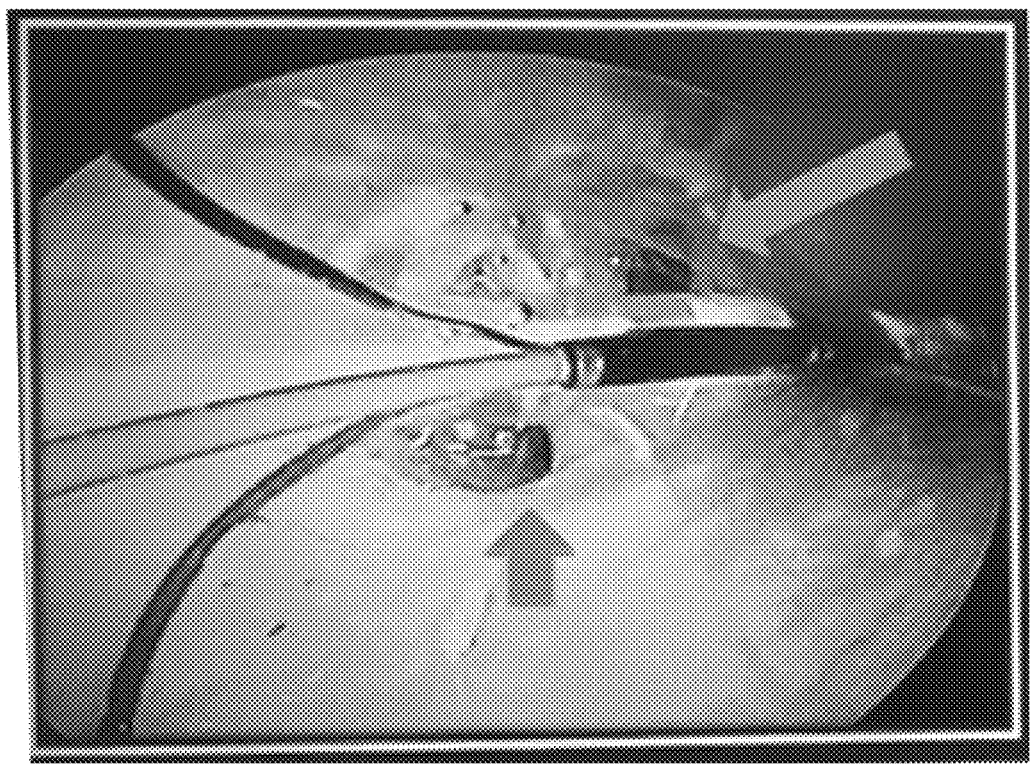
FIGS. 13A and 13B are photographs of distal portions of embolic protection devices of the present invention situated within a cadaver's vasculature according to Example 1.
Figure 13B:
Figure 14:
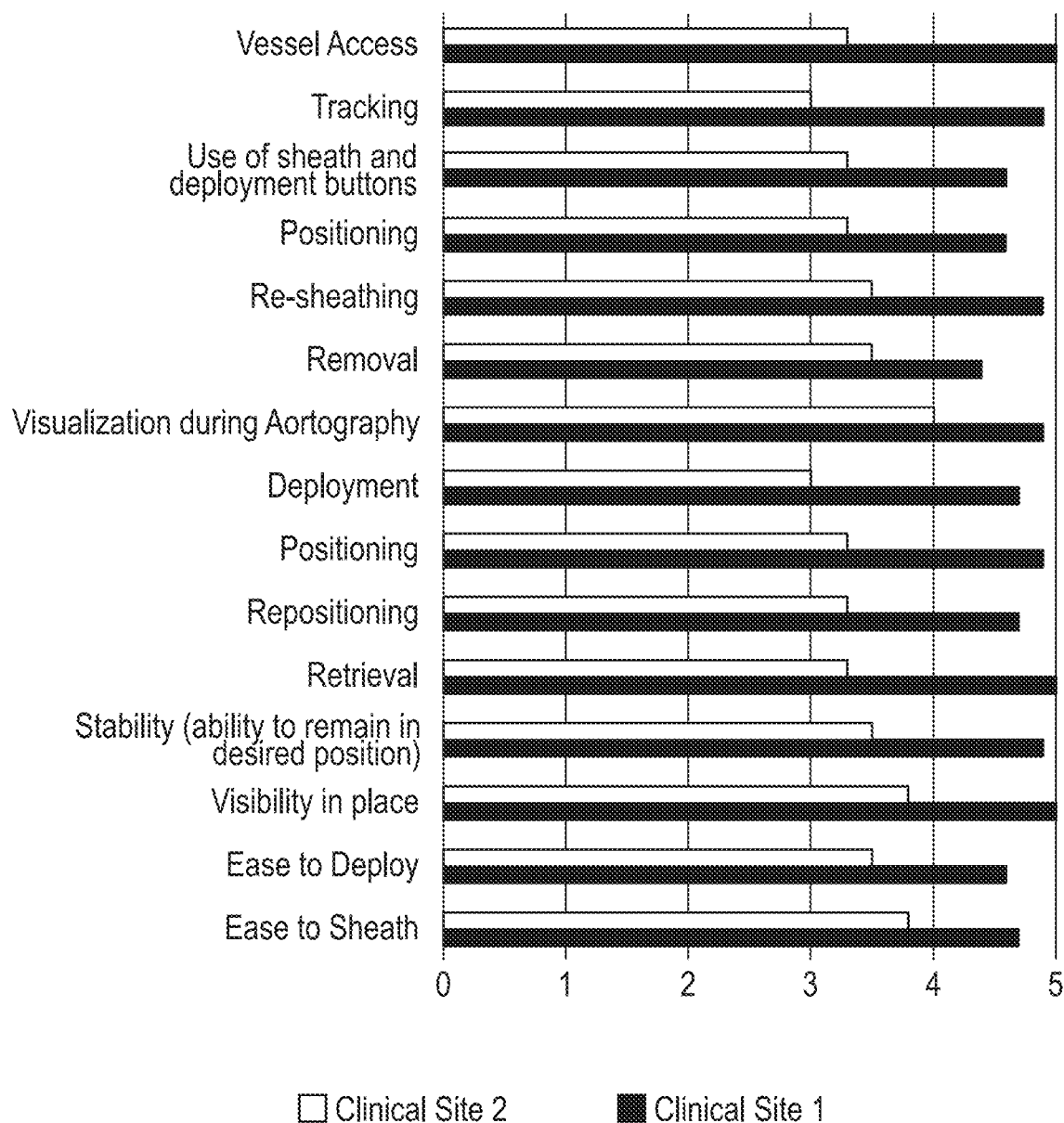
FIG. 14 is a bar graph of performance data of an embolic protection device of the present invention (the EPD-1 device) according to Example 2.
Figure 15D:
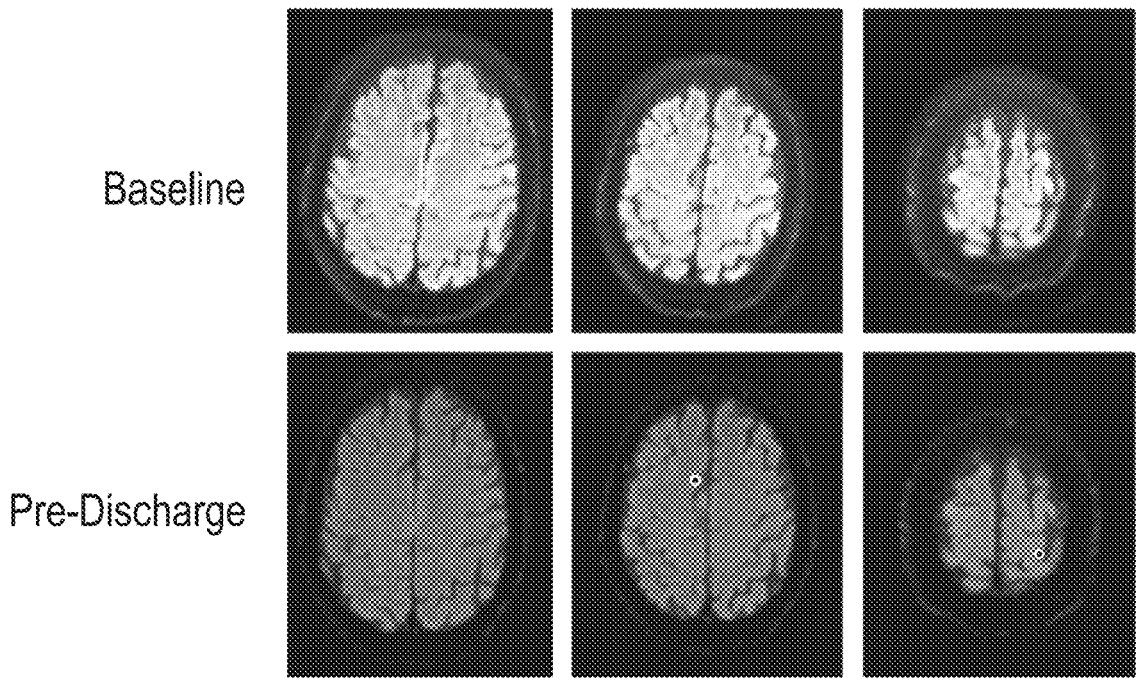
Figure 15E:
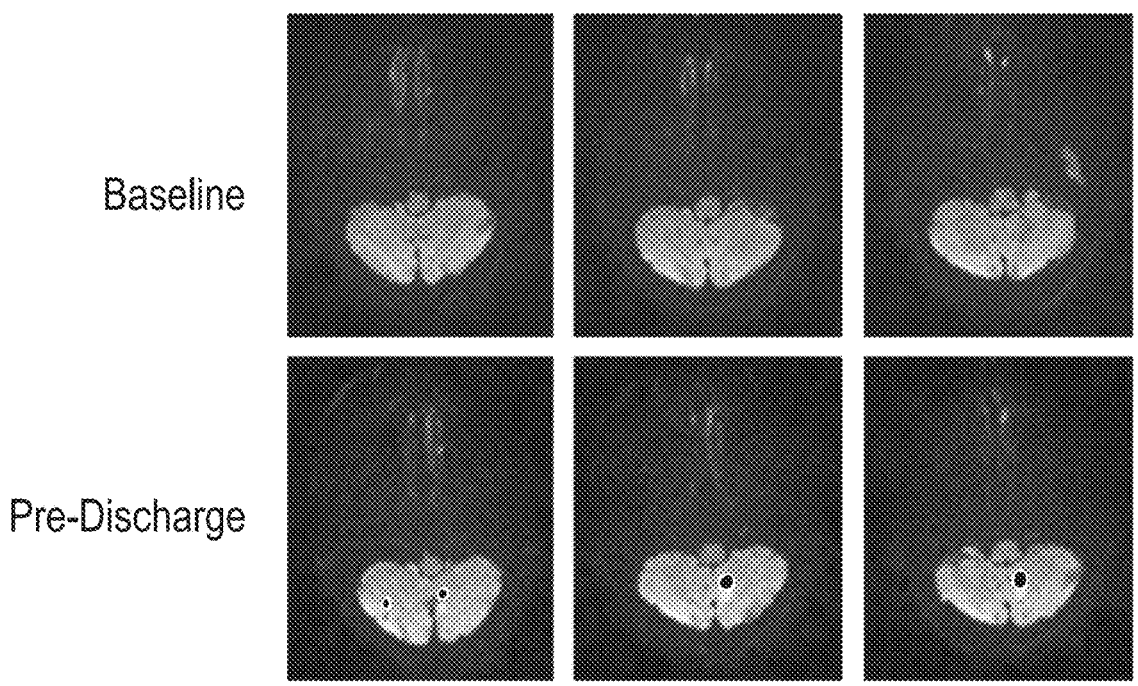
Figure 15F:
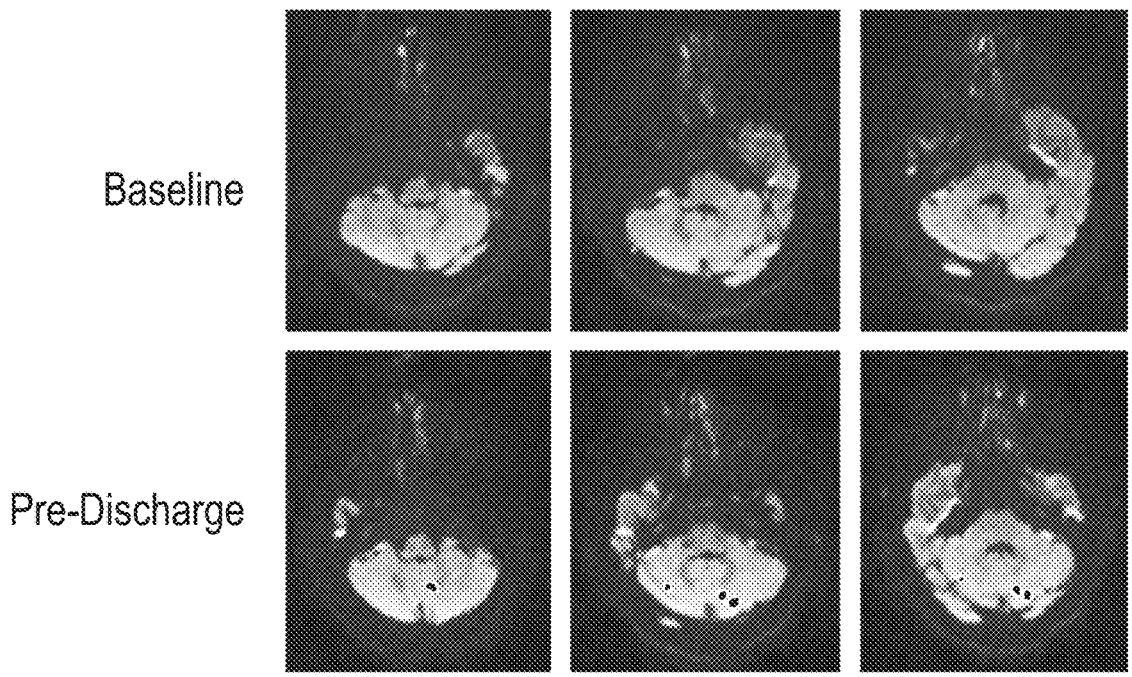
Figure 15G:
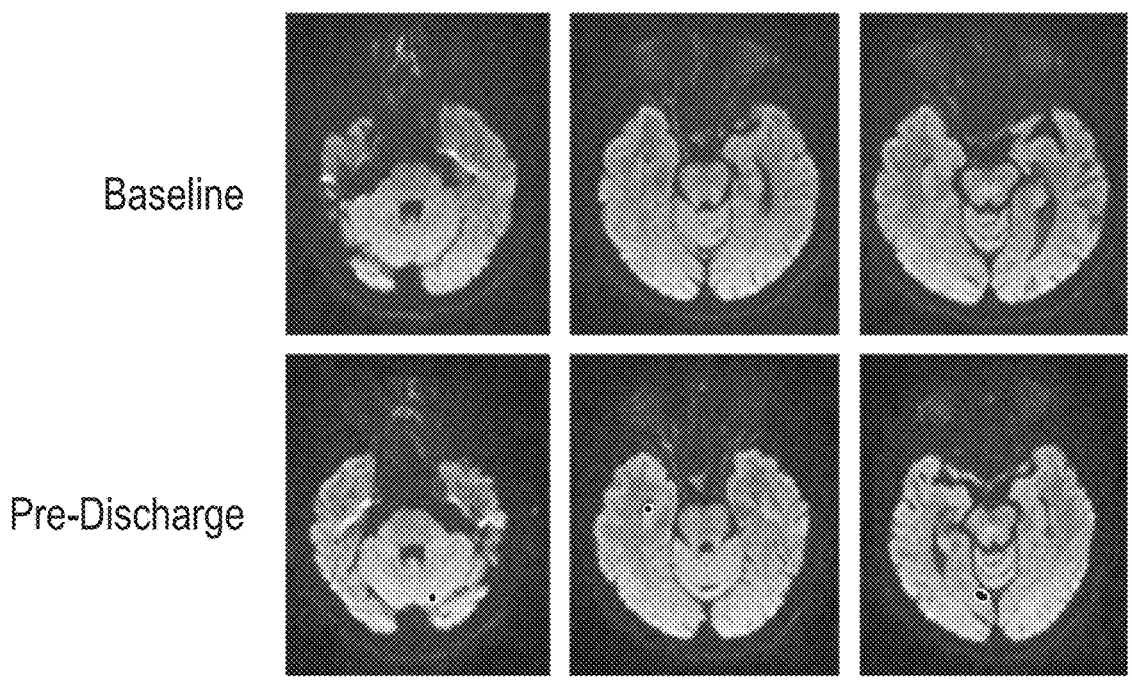
Figure 15H:
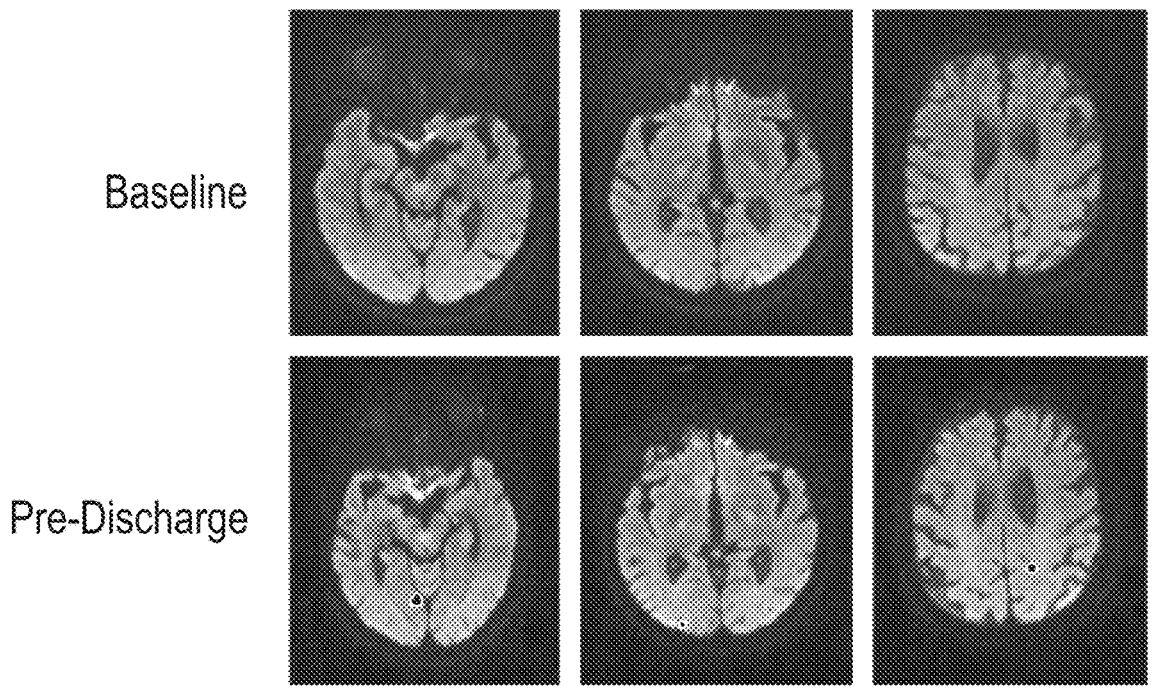
Figure 15I:
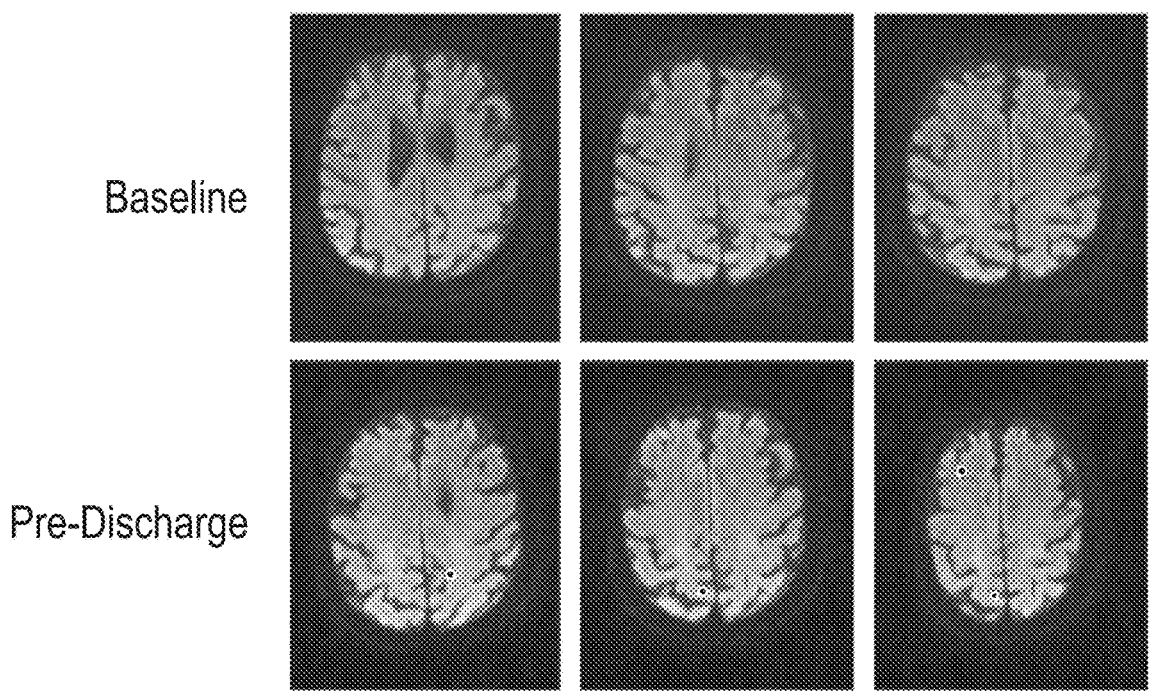

Referring to FIGS. 13A and 13B, an embolic protection device of the present invention (EPD-1) was tested in a human cadaver model to visually assess the device's ability to cover all cerebral vessels with an embolic filter while an endovascular device was passed through the aorta and alongside the EPD-1. In the photographs of FIGS. 13A and 13B, the EPD-1 is deployed and covering the opening of cerebral vessels of the cadaver while at the same time, a TAVR delivery system passes above the filter. In FIG. 13A, the TAVR delivery system is tracked along a longitudinal groove on the outer surface of the EPD-1 catheter. In FIG. 13B, the TAVR delivery system is tracked outside the groove of the EPD-1 catheter.

Example 2: Clinical Study

Referring to FIG. 14 and FIGS. 15A-15J, the safety and performance of an embolic protection device according to the present invention ("EPD-1") was assessed during transcatheter aortic valve replacement (TAVR) procedures on human subjects. The primary objective was to evaluate the performance and the treatment of effect of the use of the EPD-1 during TAVR with respect to procedure-related cerebral embolic burden as determined by diffusion-weighted magnetic resonance imaging (DW-MRI). A secondary objective was to analyze the safety profile and type of captured debris from the EPD-1 filter after TAVR.

The study was designed as a multi-center non-randomized trial including up to 5 clinical sites to evaluate the performance and the treatment effect of the use of the EPD-1 during TAVR with respect to procedure-related silent ischemic damage and cerebral embolic burden, as determined by DW-MRI studies performed before and after the procedure. A secondary objective was to analyze the safety profile and the type of captured debris from the EPD-1 filter after TAVR. The potential risk of neurological compromise and stroke was assessed based on neurological evaluations pre and post procedure. The study population was comprised of up to thirty (30) subjects with severe native aortic valve stenosis who meet the commercially approved indications for TAVR and complied with the inclusion/exclusion criteria.

Primary Endpoints: 1) Device performance: defined as the successful insertion, placement, and removal of the EPD-1. Device performance was evaluated during and after completion of the TAVR index procedure. 2) Acute cerebral embolic burden reduction after TAVR, defined as number and volume of brain lesions detected with DW MRI at Day 2-5 post TAVR procedure compared with baseline.

Secondary Endpoints: 1) Rate of major adverse cardiac and cerebrovascular events at 30-days post TAVR index procedure compared to historical data. Major Adverse Cardiac and Cerebrovascular Events (MACCE) are defined as: All-cause mortality; All stroke (major, minor, TIA); Acute Kidney Injury (Class 3). 2) Clinical assessment of subject's neurological status pre- and post-index procedure using the NIH stroke scale.

Eleven subjects were enrolled in a multi-center, non-randomized, prospective pilot study. The performance characteristics of the EPD-1 were evaluated post-procedurally and scored on a 5-point score (1, unacceptable to 5, excellent). The average performance across all patients of all characteristics for the EPD-1 was 4.8 at clinical site 1 and 3.4 at clinical site 2. Average performance scores (at each of the clinical sites) for each assessed characteristic EPD-1 performance are illustrated in the bar graphs of FIG. 14. The characteristics scored were: vessel access, tracking, use of sheath and deployment buttons, positioning, re-sheathing, removal, visualization during aortography, deployment, positioning, repositioning, retrieval, stability, visibility in place, ease to deploy, and ease to sheath.

Pre-to-post procedure aortic gradient measurements averaged 86.4% reduction in all eleven (11) subjects confirming success of TAVR treatments.

All subjects underwent DW-MRI pre-and-post-procedure, and evaluation of images were consistent with identification of some ischemic lesions. MRI was performed at the Baseline and Pre-Discharge (Day 2-5) visits in the eleven (11) subjects that underwent a Transcatheter Aortic Valve Replacement (TAVR) procedure at each of the two clinical sites. The MRI protocol consisted of the following sequences: Axial DWI, Axial FLAIR and 3D T1-weighted IR-GRE. DWI contrast is sensitive to water molecules and helps locate and quantify fresh lesions. Total lesions were counted, lesion location, size and volume was assessed, and total lesion volume were analyzed. FIGS. 15A-15J show the DW-MRI images of the brains for three (3) representative human subjects (001-05, 001-06 and 002-01).

A median lesion count of 6 and a median lesion volume of 193.9 mm$^3$ were observed among the eleven (11) subjects. A breakdown of lesions by location is detailed in Table 1. These results indicate a lower lesion count and volume when compared to both historical controls and clinical trials involving cleared and investigational embolic protection devices.

TABLE 1

Brain lesions by location for all patients (clinical sites 1 and 2) from the clinical study.

| Vascular Territory | Lesion Count |
|---|---|
| Anterior Choroidal Artery | 2 |
| Anterior Cerebral Artery | 3 |
| Middle Cerebral Artery | 40 |
| Posterior Cerebral Artery | 22 |
| Vertebrobasilar Artery | 1 |
| Anterior Inferior Cerebellar Artery | 0 |
| Posterior Inferior Cerebellar Artery | 12 |
| Total Lesion Count (Entire Brain) | 80 |

Table 2 provides a detailed comparison of lesion count and volume between the clinical study of this Example 2 and clinical studies for comparable devices. These results demonstrate that protection using the EPD-1 could reduce the number of ischemic lesions or their volume, thus supporting the utility of the procedure.

TABLE 2

Comparison of EPD-1 performance to that of cleared and investigational devices.

| Study | Device | # of Subjects | Median Lesion Count | Median Lesion Volume (mm$^3$) | Time Range of Imaging |
|---|---|---|---|---|---|
| CLEAN-TAVI | None (control) | 45 | 16 | 800 | 2 D |
| EXAMPLE 2 | EPD-1 | 11* | 6 | 193.9 | <48 hours |
| SENTINEL | Claret Medical Sentinel | 91 | 3 Protected areas only | 294 | 2-7 D |

TABLE 2-continued

Comparison of EPD-1 performance to that of cleared and investigational devices.

| Study | Device | # of Subjects | Median Lesion Count | Median Lesion Volume (mm³) | Time Range of Imaging |
|---|---|---|---|---|---|
| PROTAVI-C | Edwards Lifesciences Embrella Embolic Deflector System (investigational) | 42 | 8 | 305 | 7 D |
| DEFLECT-III | TriGuard ™ HDH Embolic Deflection Device (investigational) | 46 | N/A | 46% > 150 | 2-6 D |

The time point at which MRI was taken differs between these studies. Whereas DW-MRI was performed within 48 hours post-procedure for all patients in Example 2; for other referenced studies, imaging was performed at a longer time point. Because the appearance of hyper-intensity during DW-MRI imaging is known to evolve over time, these other referenced studies would have likely observed a higher lesion volume, had DW-MRI been taken within 48 hours post-procedure. Nonetheless, the EPD-1 outperformed the referenced, comparable devices with respect to acute cerebral embolic burden reduction. Three patients had elevated lesion counts; however, they were considered outliers as the filter was recaptured and the TAVR device post dilated. During these outlier procedures, the operators were concerned about interaction of the balloon catheter with the filter frame due to the small anatomy of the aorta. This typically results in liberation of debris.

Figure 16A:
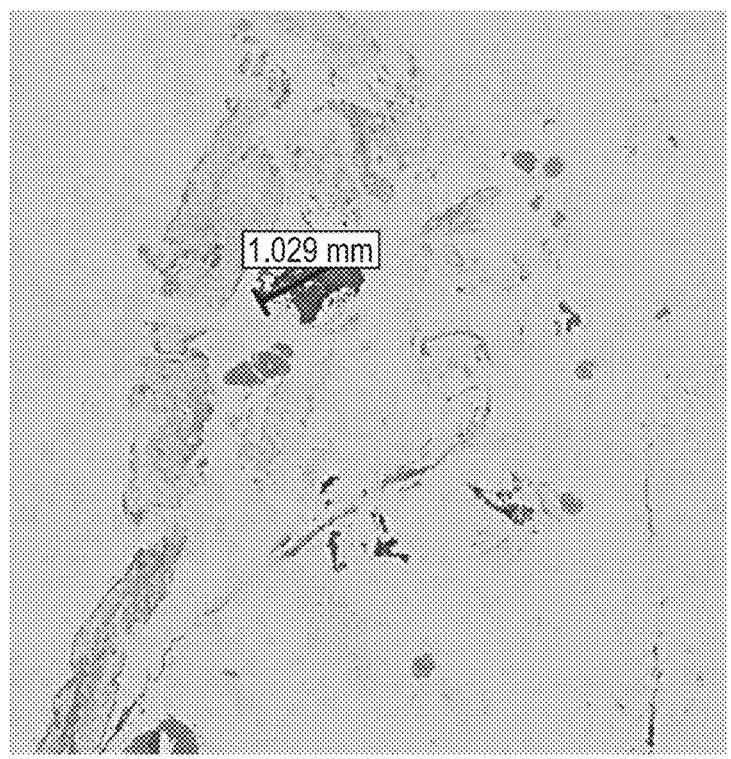
FIG. 16A is a photograph of thrombi captured by an embolic protection device of the present invention (the EPD-1 device) according to Example 2.
Figure 16B:
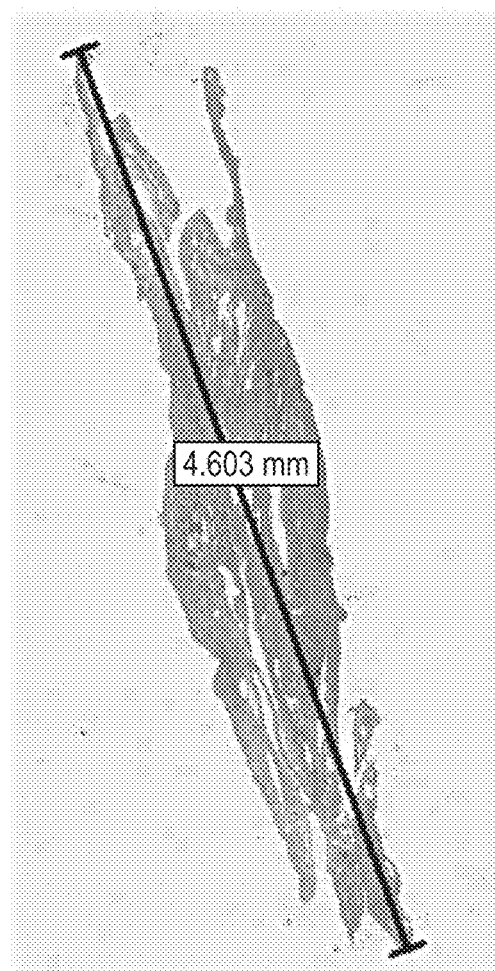
FIG. 16B is a photograph of a collagenous fragment captured within the filter of the embolic protection device (the EPD-1 device) according to Example 2.

The EPD-1 captured thrombi in all procedures. Two examples of captured thrombi are shown in the photographs of FIGS. 16A and 16B. The photograph of FIG. 16A shows a thrombi captured by the EPD-1 of Example 2. The photograph of FIG. 16B shows an actual pathologic finding of a 4.6 mm collagenous fragment captured within the EPD-1 filter during a TAVR procedure. Neurological evaluation of all patients using NUBS at discharge and 30 days post-procedure showed that scores for all patients remained at baseline levels, except for one patient developing limb ataxia. No serious adverse events were recorded. Debris captured by the embolic filter of the EPD-1 included collagen, fibrin, thrombi, and calcium.

A summary of endpoints is shown in Table 3.

TABLE 3

Summary of endpoints from the clinical studies of Example 2.

| Endpoints | Result | |
|---|---|---|
| | Success | Failure |
| Primary Endpoints | | |
| Device performance successful deployment and retrieval | 100% | 0% |
| Acute cerebral embolic burden reduction after TAVR | The EPD-1 device showed reduction in acute cerebral embolic burden when compared to both historical controls and other marketed and investigational devices. | |
| Secondary Endpoints | | |
| MACCE, 30-days post-procedure (No Events) | 100% | 0% |

TABLE 3-continued

Summary of endpoints from the clinical studies of Example 2.

| Endpoints | Result | |
|---|---|---|
| | Success | Failure |
| NIH stroke scale pre- and-post-procedure | 100% (Scores = 0) | 0% |
| Gross histologic evaluation of embolic debris captured | 100% | 0% |

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

It is to be understood by one having ordinary skill in the art that the specific devices and processes illustrated in the attached drawings and described in this specification are simply example embodiments of the inventive concepts defined in the appended claims. Hence, specific dimensions and other physical characteristics relating to the embodiments disclosed herein are not to be considered as limiting, unless the claims expressly state otherwise. It is also to be understood that construction of the described invention and other components is not limited to any specific material. Other example embodiments of the invention disclosed herein may be formed from a wide variety of materials, unless described otherwise herein.

Changes and modifications in the specifically-described embodiments may be carried out without departing from the principles of the present invention, which is intended to be limited only by the scope of the appended claims as interpreted according to the principles of patent law including the doctrine of equivalents.

What is claimed is:

1. An embolic protection device comprising:
   a catheter having a proximal end, a distal end, and a lumen extending from the proximal end to the distal end along a longitudinal axis of the catheter, wherein the lumen is configured to house a guidewire, and a distal portion of the catheter that assumes a generally arcuate shape being at least a semi-circle when the guidewire is at least partially longitudinally retracted;

a self-expanding embolic filter that is disposed around the catheter, proximal to the distal portion, wherein the embolic filter comprises a frame, wherein the frame defines an opening of the embolic filter, and the frame includes
 a fixed portion coupled to the catheter, proximal to the distal portion, wherein the fixed portion does not move in a longitudinal direction,
 a movable portion continuous with the fixed portion of the frame, and
 two sides, each side of the frame extending generally in a first lateral direction away from the catheter and then looping back on an opposite side around the catheter, and extending generally in the opposite lateral direction before converging and meeting to form the opening of the embolic filter having a substantially elliptical, ovular or circular shape;
a deployment mechanism that is disposed around at least a portion of the catheter, wherein the deployment mechanism is longitudinally movable with respect to the catheter, the deployment mechanism is configured to contain the embolic filter in a collapsed configuration, and the embolic filter is configured to self-expand upon longitudinal retraction of the deployment mechanism;
a wire coupled to the movable portion of the frame, wherein the wire is longitudinally movable with respect to the catheter and urges the movable portion of the frame;
when the wire is longitudinally advanced, in a distal direction, to a first position, the wire is configured to urge the movable portion of the frame in a longitudinal direction and bend the frame longitudinally towards the distal end of the catheter and laterally outward from the catheter, such that the opening of the embolic filter generally faces the distal end of the catheter and expands to a first diameter; and
when the wire is longitudinally advanced, in a distal direction, to a second position distally farther than the first position, the wire is configured to urge the movable portion of the frame and extend the frame radially outward from the catheter, such that the opening of the embolic filter expands to a second diameter larger than the first diameter.

2. The embolic protection device of claim 1, wherein the wire, when longitudinally advanced to the first position, is configured to bend the frame so that the opening of the embolic filter defined by the frame is substantially perpendicular to the longitudinal axis of the catheter.

3. The embolic protection device of claim 1, wherein the wire, when longitudinally retracted to a proximal position, is configured to position the frame so that the opening of the embolic filter defined by the frame is substantially parallel or angled less than 45 degrees with respect to the longitudinal axis of the catheter.

4. The embolic protection device of claim 1, further comprising an outer catheter disposed around at least a portion of the catheter and coaxial with the lumen of the catheter, wherein the outer catheter is longitudinally slidable over the catheter; and
 wherein the wire is coupled to a distal portion of the outer catheter such that the wire is moved by the outer catheter sliding over the catheter.

5. The embolic protection device of claim 4, further comprising an inner catheter disposed between the outer catheter and the catheter, wherein the inner catheter is longitudinally slidable over the catheter; and
 a guide attached at one end to a distal portion of the inner catheter so that the guide is moved by the inner catheter sliding over the catheter, wherein the guide slidably receives the movable portion of the frame causing the guide to flex outwardly away from the catheter.

6. The embolic protection device of claim 5, wherein the guide is a top guide and the embolic protection device further comprising a bottom guide attached at one end to the catheter, wherein the bottom guide and the top guide are arranged on opposite sides of the catheter, and wherein the bottom guide receives the fixed portion of the frame causing the bottom guide to flex outwardly away from the catheter.

7. The embolic protection device of claim 5, further comprising:
 a handle coupled to the proximal end of the catheter;
 a top pull coupled to a proximal portion of the outer catheter and is longitudinally movable within the handle;
 a bottom pull coupled to a proximal portion of the inner catheter and is longitudinally movable within the handle, wherein the bottom pull is in temporary engagement with the top pull;
 when the top pull and the bottom pull are engaged, the top pull and the bottom pull are moved in unison by movement of a slider, which, in turn, urges the guide together with the movable portion of the frame in the longitudinal direction and expands the opening of the embolic filter to the first diameter; and
 when the top pull and the bottom pull are disengaged, the top pull is moved without the bottom pull by movement of the slider, which, in turn, urges the movable portion of the frame in the radial direction and expands the opening of the embolic filter to the second diameter.

8. The embolic protection device of claim 1, wherein embolic protection device has a handle, wherein the handle comprises a mechanism configured to advance or retract the wire.

9. The embolic protection device of claim 1, wherein the catheter extends through the opening of the embolic filter.

10. The embolic protection device of claim 1, wherein the distal portion of the catheter comprises a radiopaque marker.

11. The embolic protection device of claim 10, wherein the radiopaque marker comprises one or more circumferential bands.

12. The embolic protection device of claim 1, wherein the frame comprises a shape memory material.

13. The embolic protection device of claim 1, wherein the embolic filter comprises a filter medium, which comprises a semi-permeable polyurethane material having a pore size of from about 100 microns to about 150 microns.

14. The embolic protection device of claim 1, wherein the embolic protection device comprises a longitudinal groove along an outer surface of the catheter, the groove configured to guide a second catheter device inserted alongside the embolic protection device.

15. The embolic protection device of claim 1, wherein the deployment mechanism comprises a sheath that is circumferentially disposed around at least a portion of the catheter, wherein the sheath deploys the self-expanding embolic filter when the sheath is at least partially longitudinally retracted.

16. The embolic protection device of claim 1, wherein the distal portion of the catheter comprises one or more apertures that communicates with the lumen of the catheter.

17. The embolic protection device of claim 1, wherein when the wire is longitudinally advanced, in a distal direction, the embolic filter transitions from self-expanded to partially expanded.

18. The embolic protection device of claim 17, wherein when the wire is further longitudinally advanced, in a distal direction, the embolic filter transitions from partially expanded to fully expanded.

19. The embolic protection device of claim 18, wherein when the embolic filter transitions from partially expanded to fully expanded the embolic filter has a range of diameters between 25 mm and 40 mm.

20. The embolic protection device of claim 1, wherein the embolic filter is configured to self-expand to a first state upon longitudinal retraction of the deployment mechanism, the first state being less than a fully expanded state.

21. The embolic protection device of claim 1, wherein the wire inhibits self-expansion of the embolic filter.

22. The embolic protection device of claim 1, wherein the distal portion of the catheter comprises radiopaque material and further comprises a plurality of radiopaque marker bands.

23. The embolic protection device of claim 22, wherein radiopaque marker bands of the plurality of radiopaque marker bands have different widths.

24. The embolic protection device of claim 1, wherein the embolic filter comprises a semi-permeable polyurethane material.

25. The embolic protection device of claim 1, further comprising:
an inner catheter longitudinally slidable over the catheter; and
a guide coupled to a distal portion of the inner catheter and slidable with the inner catheter, wherein the guide receives the movable portion of the frame.

26. The embolic protection device of claim 25, wherein a proximal portion of the guide is coupled to the distal portion of the inner catheter, and wherein a distal portion of the guide is configured to flex outwardly.

27. The embolic protection device of claim 26, wherein the guide is coupled to a first side of the distal portion of the inner catheter, and further comprising a second guide coupled to a second side of the distal portion of the inner catheter, the second side opposite the first side, wherein the second guide receives the fixed portion of the frame.

* * * * *